United States Patent
Farina et al.

(10) Patent No.: US 6,780,875 B2
(45) Date of Patent: Aug. 24, 2004

(54) QUINOLINE-4-CARBOXAMIDE DERIVATIVES AS NK-3 AND NK-2 RECEPTOR ANTAGONISTS

(75) Inventors: Carlo Farina, Milan (IT); Giuseppe Giardina, Milan (IT); Mario Grugni, Milan (IT); Marcel Morvan, St Grégoire (FR); Guy Marguerite Marie Gérard Nadler, St Grégoire (FR); Luca Francesco Raveglia, Milan (IT)

(73) Assignees: SmithKline Beecham S.p.A., Milan (IT); SmithKline Beecham Laboratories Pharmaceutiques, Nanterrer (FR)

(*) Notice: Subject to any disclaimer, the term of this patent is extended or adjusted under 35 U.S.C. 154(b) by 0 days.

(21) Appl. No.: 10/358,938

(22) Filed: Feb. 5, 2003

(65) Prior Publication Data

US 2003/0212101 A1 Nov. 13, 2003

Related U.S. Application Data

(63) Continuation of application No. 10/159,218, filed on May 31, 2002, which is a continuation of application No. 09/856,085, filed as application No. PCT/EP99/09115 on Nov. 19, 1999, now abandoned.

(30) Foreign Application Priority Data

Nov. 20, 1998 (GB) ............................................. 9825552
Nov. 20, 1998 (GB) ............................................. 9825553

(51) Int. Cl.[7] .................... A61K 31/4709; C07D 401/14
(52) U.S. Cl. ......................... 514/314; 546/169; 546/20; 544/128; 544/333; 544/363; 514/235.2; 514/253; 514/278; 514/311
(58) Field of Search ................................. 514/314, 311, 514/278, 253, 235.2; 546/169, 20; 544/128, 333, 363

(56) References Cited

U.S. PATENT DOCUMENTS 5,811,553 A * 9/1998 Farina et al. ............... 546/153

FOREIGN PATENT DOCUMENTS

| WO | 97/19926 | * | 6/1997 | ................. 514/253 |
| WO | 98/52942 | * | 11/1998 | ................. 514/253 |

* cited by examiner

Primary Examiner—Charanjit S. Aulakh

(74) Attorney, Agent, or Firm—Nora Stein-Fernandez; Theodore R. Furman

(57) ABSTRACT

A compound, or a solvate or a salt thereof, of formula (I):

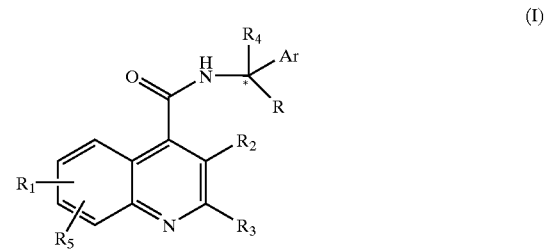

(I)

wherein, Ar is an optionally substituted aryl or a $C_{5-7}$ cycloalkdienyl group, or an optionally substituted $C_{5-7}$ cycloalkyl group, or an optionally substituted single or fused ring aromatic heterocyclic group;

R is hydrogen, linear or branched $C_{1-6}$ alkyl, $C_{3-7}$ cycloalkyl, $C_{3-7}$ cycloalkylalkyl;

$R_1$ represents hydrogen or up to three optional substituents selected from the list consisting of: $C_{1-6}$ alkyl, $C_{1-6}$ alkenyl, aryl, $C_{1-6}$ alkoxy, hydroxy, halogen, nitro, cyano, carboxy, carboxamido, sulphonamido, $C_{1-6}$ alkoxycarbonyl, trifluoromethyl, acyloxy, amino or mono- and di-$C_{1-6}$ alkylamino, $R_2$ represents a moiety —$(CH_2)_n$—$NYY_2$ wherein n is an integer in the range of from 1 to 9, $Y_1$ and $Y_2$ are independently selected from $C_{1-6}$-alkyl; $C_{1-6}$ alkyl substituted with hydroxy, alkoxy, $C_{1-6}$ alkylamino or bis ($C_{1-6}$ alkyl) amino; C3–6 cycloalkyl; C4–6 azacycloalkyl; $C_{1-6}$-alkenyl; aryl or aryl-$C_{1-6}$-alkyl or $Y_1$ and $Y_2$ together with the nitrogen atom to which they are attached represent an optionally substituted N-linked single or fused ring heterocyclic group;

$R_3$ is branched or linear $C_{1-6}$ alkyl, $C_{3-7}$ cycloalkyl, $C_{4-7}$ cycloalkylalkyl, optionally substituted aryl, or an optionally substituted single or fused ring aromatic heterocyclic group; and $R_4$ represents hydrogen or $C_{1-6}$ alkyl, $R_5$ represents hydrogen or halogen; a process for preparing such compounds, a pharmaceutical composition comprising such compounds and the use of such compounds and composition in medicine.

6 Claims, No Drawings

QUINOLINE-4-CARBOXAMIDE DERIVATIVES AS NK-3 AND NK-2 RECEPTOR ANTAGONISTS

This is a continuation of application Ser. No. 10/159,218 filed May 31, 2002, which is a continuation of Ser. No. 09/856,085, filed Sep. 4, 2001, which is a 371 application of International Application No. PCT/EP99/09115, filed Nov. 19, 1999.

The present invention relates to novel compounds, in particular to novel quinoline derivatives, to processes for the preparation of such compounds, to pharmaceutical compositions containing such compounds and to the use of such compounds in medicine.

The mammalian peptide Neurokinin B (NKB) belongs to the Tachykinin (TK) peptide family which also include Substance P (SP) and Neurokinin A (NKA). Pharmacological and molecular biological evidence has shown the existence of three subtypes of TK receptor ($NK_1$, $NK_2$ and $NK_3$) and NKB binds preferentially to the $NK_3$ receptor although it also recognises the other two receptors with lower affinity (Maggi et al, 1993, *J. Auton. Pharmacol.*, 13, 23–93).

Selective peptidic $NK_3$ receptor antagonists are known (Drapeau, 1990 *Regul. Pept.*, 31, 125–135), and findings with peptidic $NK_3$ receptor agonists suggest that NKB, by activating the $NK_3$ receptor, has a key role in the modulation of neural input in airways, skin, spinal cord and nigrostriatal pathways (Mycrs and Undem, 1993 *J. Physiol.*, 470, 665–679; Counture et al., 1993, *Regul. Peptides*, 46, 426–429, Mccarson and Krause, 1994, *J. Neurosci.*, 14 (2), 712–720; Arenas et al. 1991, *J. Neurosci* 18, 2332–8). However, the peptide-like nature of the known antagonists makes them likely to be too labile from a metabolic point of view to serve as practical therapeutic agents.

Copending International Patent Application number PCT/EP98/03014 discloses certain compounds stated to be non-peptide NK-3 antagonists and also to have NK-2 antagonist activity. These compounds are therefore considered to be of potential use in the prevention and treatment of a wide variety of clinical conditions which are characterized by overstimulation of the tachykinin receptors, in particular NK-3 and NK-2.

We have now discovered a further novel class of non-peptide NK-3 antagonists which are far more stable from a metabolic point of view than the known peptidic NK-3 receptor antagonists and are of potential therapeutic utility. These compounds also have NK-2 antagonist activity and are therefore considered to be of potential use in the prevention and treatment of a wide variety of clinical conditions which are characterized by overstimulation of the tachykinin receptors, in particular NK-3 and NK-2.

These conditions include respiratory diseases, such as chronic obstructive pulmonary disease (COPD), asthma, airway hyperreactivity, cough; inflammatory diseases such as inflammatory bowel disease, psoriasis, fibrositis, osteoarthritis, rheumatoid arthritis and inflammatory pain; neurogenic inflammation or peripheral neuropathy, allergies such as eczema and rhinitis; ophthalmic diseases such as ocular inflammation, conjunctivitis, vernal conjuctivitis and the like; cutaneous diseases, skin disorders and itch, such as cutaneous wheal and flare, contact dermatitis, atopic dermatitis, urticaria and other eczematoid dermatitis; adverse immunological reactions such as rejection of transplanted tissues and disorders related to immune enhancement or suppression such as systhemic lupus erythematosis; gastrointestinal (GI) disorders and diseases of the GI tract such as disorders associated with the neuronal control of viscera such as ulcerative colitis, Crohn's disease, irritable bowel syndrome (IBS), gastro-exophageous reflex disease (GERD); urinary incontinence and disorders of the bladder function; renal disorders (hereinafter referred to as the 'Primary Conditions').

Certain of these compounds also show CNS activity and hence are considered to be of particular use in the treatment of disorders of the central nervous system such as anxiety, depression, psychosis and schizophrenia; neurodegenerative disorders such as AIDS related dementia, senile dementia of the Alzheimer type, Alzheimer's disease, Down's syndrome, Huntington's disease, Parkinson's disease, movement disorders and convulsive disorders (for example epilepsy); demyelinating diseases such as multiple sclerosis and amyotrophic lateral sclerosis and other neuropathological disorders such as diabetic neuropathy, AIDS related neuropathy, chemotherapy-induced neuropathy and neuralgia; addiction disorders such as alcoholism; stress related somatic disorders; reflex sympathetic dystrophy such as shoulder/hand syndrome; dysthymic disorders; eating disorders (such as food intake disease); fibrosing and collagen diseases such as scleroderma and eosinophilic fascioliasis; disorders of the blood flow caused by vasodilation and vasospastic diseases such as angina, migraine and Reynaud's disease and pain or nociception, for example, that is attributable to or associated with any of the foregoing conditions especially the transmission of pain in migraine, (hereinafter referred to as the 'Secondary Conditions').

The compounds of formula (I) are also considered to be useful as diagnostic tools for assessing the degree to which neurokinin-3 and neurokinin-2 receptor activity (normal, overactivity or underactivity) is implicated in a patient's symptoms.

According to the present invention there is provided a compound, or a solvate or a salt thereof, of formula (I):

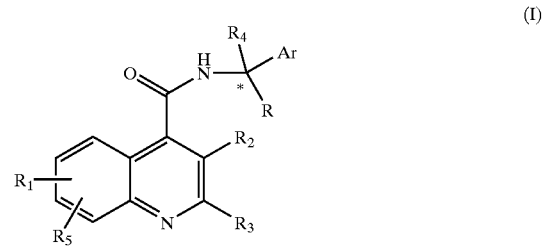

(I)

wherein, Ar is an optionally substituted aryl or a $C_{5-7}$ cycloalkdienyl group, or an optionally substituted $C_{5-7}$ cycloalkyl group, or an optionally substituted single or fused ring aromatic heterocyclic group;

R is hydrogen, linear or branched $C_{1-6}$ alkyl, $C_{3-7}$ cycloalkyl, $C_{3-7}$ cycloalkylalkyl;

$R_1$ represents hydrogen or up to three optional substituents selected from the list consisting of: $C_{1-6}$ alkyl, $C_{1-6}$ alkenyl, aryl, $C_{1-6}$ alkoxy, hydroxy, halogen, nitro, cyano, carboxy, carboxamido, sulphonamido, $C_{1-6}$ alkoxycarbonyl, trifluoromethyl, acyloxy, amino or mono- and di-$C_{1-6}$ alkylamino;

$R_2$ represents a moiety —$(CH_2)_n$—$NY_1Y_2$ wherein n is an integer in the range of from 1 to 9, $Y_1$ and $Y_2$ are independently selected from $C_{1-6}$-alkyl; $C_{1-6}$ alkyl substituted with hydroxy, alkoxy, $C_{1-6}$ alkylamino or bis ($C_{1-6}$ alkyl) amino; C3–6 cycloalkyl; C4–6 azacycloalkyl; $C_{1-6}$-alkenyl; aryl or aryl-$C_{1-6}$-alkyl or $Y_1$ and $Y_2$ together with the nitrogen atom to which they are attached represent an optionally substituted N-linked single or fused ring heterocyclic group;

$R_3$ is branched or linear $C_{1-6}$ alkyl, $C_{3-7}$ cycloalkyl, $C_{4-7}$ cycloalkylalkyl, optionally substituted aryl, or an optionally substituted single or fused ring aromatic heterocyclic group; and $R_4$ represents hydrogen or $C_{1-6}$ alkyl.

$R_5$ represents hydrogen or halogen.

Preferably $R_5$ represents hydrogen. In another preferred aspect R5 is chloro or bromo.

Suitably, Ar represents optionally substituted phenyl, unsubstituted phenyl or cyclohexyl.

Suitably, Ar represents cyclohexyl.

Preferably Ar is phenyl or cyclohexyl.

Suitably, R represents $C_{1-6}$ alkyl, for example methyl or ethyl or iso-propyl.

In one preferred aspect, R is ethyl. In another preferred aspect, R is methyl or isopropyl.

Suitably $R_1$ represents hydrogen, $C_{1-6}$ alkoxy, for example methoxy, or hydroxy.

Preferably, $R_1$ represents hydrogen. In another preferred aspect, R1 is methoxy or hydroxy.

Suitably, $NY_1Y_2$ represents an optionally substituted N-linked single or fused ring heterocyclic group.

Suitable N-linked single or fused heterocyclic groups, include groups in which any single or fused ring is saturated or unsaturated and consists of 5- or 6-ring atoms, said ring atoms optionally comprising 1 or 2 additional heteroatoms selected from O or N and wherein one or two ring atoms are optionally substituted with one or two oxo groups or one or two of hydroxy, carboxy, carboxy C1–6 alkyl, $C_{1-6}$ alkoxycarbonyl, aminocarbonyl, C1–6 alkylcarbonyl optionally substituted with an aromatic heterocyclic group, arylcarbonyl, aryl C1–6 alkylcarbonyl, carboxy C1–6 alklycarbonyl, carboxyarylcarbonyl, amino, C1–6 alkylcarbonylamino, $C_{1-6}$ alkyl, $C_{1-6}$ hydroxyalkyl, aryl, aryl, C1–6 alkyl, $C_{3-7}$ cycloalkyl, optionally substituted C4–7 cycloalkenyl, optionally substituted C4–7 azacycloalkyl, optionally substituted C4–7 diazacycloalkyl, optionally substituted C4–7 oxaazacycloalkyl, optionally substituted C4–7 thiazacycloalkyl, optionally substituted C4–7 thiazacycloalkenyl, $C_{3-7}$ cycloalkylalkyl, hydroxy C1–6 alkoxy C1–6 alkyl, C1–6 alkoxy C1–6 alkyl, di C1–6 alkylaminocarbonyl, di C1–6 alkylamino C1–6 alkylcarbonyl, optionally substituted C4–7 azacycloalkyl C1–6 alkylcarbonyl, optionally substituted C4–7 diazacycloaklyl C1–6 alkylcarbonyl, optionally substituted C4–7oxaazacycloalkyl C1–6 alkylcarbonyl, optionally susbtituted carboxamidine, C1–6 alkylaminothiocarbonyl, optionally substituted nitrovinyl, aminosulphonyl, di C1–6 alklyaminosulphonyl, or an optionally substituted spiroheterocyclic ring or a single or fused ring aromatic heterocyclic group, or the substituents on adjacent ring atoms form a carbocyclic ring; said aryl or aromatic heterocyclic groups being optionally substituted with one or two $C_{1-6}$ alkyl, alkoxy, hydroxy, halogen or halogenalkyl groups; wherein, unless otherwise defined optionally substituted means substituted with up to three substituents selected from the list consisting of: amino, alkylamino, alkyl, aryl, heterocyclyl, alkylaryl, aralkyl, oxo, hydroxy and nitrile.

Preferably, the additional heteroatom is N.

Favoured optional substituents for the N-linked single or fused heterocyclic groups are selected from carboxy C1–6 alkyl, aminocarbonyl, C1–6 alkylcarbonyl optionally substituted with an aromatic heterocyclic group, arylcarbonyl, aryl C1–6 alkylcarbonyl, carboxy C1–6 alklycarbonyl, carboxyarylcarbonyl, amino, C1–6 alkylcarbonylamino, $C_{1-6}$ alkyl, $C_{1-6}$ hydroxyalkyl, aryl, aryl C1–6 alkyl, $C_{3-7}$ cycloalkyl, optionally substituted C4–7 cycloalkenyl, optionally substituted C4–7 azacycloalkyl, optionally substituted C4–7 diazacycloalkyl, optionally substituted C4–7 oxaazacycloalkyl, optionally substituted C4–7 thiazacycloalkyl, optionally substituted C4–7 thiazacycloalkenyl, $C_{3-7}$ cycloalkylalkyl, hydroxy C1–6 alkoxy C1–6 alkyl, C1–6 alkoxy C1–6 alkyl, di C1–6 alkylaminocarbonyl, di C1–6 alkylamino C1–6 alkylcarbonyl, optionally substituted C4–7 azacycloalkyl C1–6 alkylcarbonyl, optionally substituted C4–7 diazacycloaklyl C1–6 alkylcarbonyl, optionally substituted C4–7oxaazacycloalkyl C1–6 alkylcarbonyl, optionally susbtituted carboxamidine, C1–6 alkylaminothiocarbonyl, optionally substituted nitrovinyl, aminosulphonyl, di C1–6 alklyaminosulphonyl, or an optionally substituted spiroheterocyclic ring; wherein, unless otherwise defined optionally substituted means substituted with up to three substituents selected from the list consisting of: amino, alkylamino, alkyl, aryl, heterocyclyl, alkylaryl, aralkyl, oxo, hydroxy, nitrile. Preferred optional substituents for the N-linked single or fused heterocyclic groups include isopropylcarbonyl, hydroxyethyl, cyclohexyl, phenyl, benzyl, isopropyl, phenethyl, 1-piperidinyl, hydroxyethoxyethyl, (4-hydroxy)-1-piperidinyl, 4-piperidinyl, (1-methyl)-4-piperidinyl, dimethylaminomethylcarbonyl, diethylaminoethylcarbonyl, (4-methyl)-1-piperazinylmethylcarbonyl, 4-morpholinylethylcarbonyl, amino, (4-methyl)-1-piperazinyl, 1-piperazinyl, N-methyl-N'-cyanocarboxamidine, 2-thiazolinyl, pyrrolidinyl-N-cyanomethyleneimine, pyrrolidinyl-N-methylmethyleneimine, 1-pyrrolidinyl-2-nitrovinyl, carboxamidine, carboxyethylcarbonyl, pyrrolidinyl-N-methylsulphonylmethyleneimine, (2-carboxy)-phenylcarbonyl, aminosulphonyl, dimethylaminosulphonyl, carboxymethyl.

When present oxo substituents are preferably alpha to the point of linkage of the N-linked single or fused heterocyclic group.

When a hetero atom of the N-linked single or fused heterocyclic group is substituted, preferred substituents are selected from $C_{1-6}$ alkyl, hydroxy C1–6 alkyl for example hydroxyethyl, $C_{3-7}$ cycloalkyl, $C_{3-7}$ cycloalkylalkyl, aryl and arylalkyl, for example methyl, ethyl, isopropyl, phenyl, phenethyl, or benzyl, optionally substituted C4–7 azacycloalkyl for example 4-piperidinyl or (1-methyl)-4-piperidinyl, dialkylaminoalkylcarbonyl for example dimethylaminomethylcarbonyl or diethylaminoethylcarbonyl, hydroxy C1–6 alkoxy C1–6 alkyl for example hydroxyethoxyethyl, optionally substituted C4–7 diazacycloalkyl C1–6 alkylcarbonyl or C4–7 oxaazacycloalkyl C1–6 alkylcarbonyl for example, (4-methyl)-1-piperazinylmethylcarbonyl, 4-morpholinylethylcarbonyl, optionally substituted carboxamidine for example carboxamidine or N-methyl-N'-cyanocarboxamidine, or pyrrolidinyl-N-cyanomethyleneimine or pyrrolidinyl-N-methylmethyleneimine or pyrrolidinyl-N-methylsulphonylmethyleneimine, optionally substituted nitrovinyl for example 1-pyrrolidinyl-2-nitrovinyl, optionally substituted C4–7 thiazacycloalkenyl for example 2-thiazolinyl, carboxy C1–6 alklycarbonyl for example carboxyethylcarbonyl, carboxyarylcarbonyl for example (2-carboxy)-phenylcarbonyl, aminosulphonyl, di C1–6 alklyaminosulphonyl for example dimethylaminosulphonyl, carboxy C1–6 alkyl for example carboxymethyl.

Fused heterocyclic groups include groups having one or more rings which share one or more atoms, such as spiro fused rings, or one or more bonds.

A suitable N-linked single ring heterocyclic group comprising a 5-membered saturated heterocyclic ring is a pyrrolidin-1-yl group.

A suitable N-linked single ring heterocyclic group comprising a 6-membered saturated heterocyclic ring is an optionally substituted piperidin-1-yl group, for example a 4-(piperidin-1-yl)piperidin-1-yl group or 4-aminopiperidin-1-yl group.

A suitable N-linked single ring 6-membered saturated heterocyclic group comprising an additional heteroatom is an optionally substituted piperazin-1yl group, for example an optionally substituted 4-alkylpiperazin-1-yl group.

A suitable N-linked fused ring heterocyclic group includes a 5-or 6-membered saturated or unsaturated heterocyclic ring fused to a benzene ring.

A suitable N-linked fused ring heterocyclic group comprising a 6-membered saturated heterocyclic ring fused to a benzene ring is a 2-(1,2,3,4-tetrahydro)isoquinolinyl group.

Suitable, N-linked fused heterocyclic groups include spiro fused groups, for example 1,4-dioxa-8-azaspiro[4.5]dec-8-yl group or 3-oxo-2,8-diazaspiro[4.5]dec-8-yl or 2,4-dioxo-1,3,8-triazaspiro[4.5]dec-8-yl or 2,7-diazaspiro[4.4]non-2-yl or 2,3-dioxa-1,8-diazaspiro[4.5]dec-8-yl.

One preferred value of —NY$_1$Y$_2$ is a piperazin-1-yl group, especially a 4-hydroxyalkylpiperazin-1-yl, or 4-(dialkylaminoalkylcarbonyl)piperazin-1-yl, or 4-(azacycloalkyl)piperazin-1-yl, which piperazinyl group may be substituted or unsubstituted A particularly preferred value of —NY$_1$Y$_2$ is a group of formula (a), (b) (c) or (d):

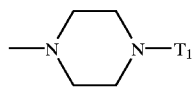

(a)

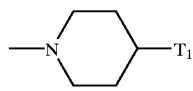

(b)

wherein T$_1$ represents isopropylcarbonyl, hydroxyethyl, cyclohexyl, phenyl, benzyl, isopropyl, phenethyl, 1-piperidinyl, hydroxyethoxyethyl, (4-hydroxy)-1-piperidinyl, 4-piperidinyl, (1-methyl)-4-piperidinyl, dimethylaminomethylcarbonyl, diethylaminoethylcarbonyl, (4-methyl)-1-piperazinylmethylcarbonyl, 4-morpholinylethylcarbonyl, amino, (4-methyl)-1-piperazinyl, 1-piperazinyl, N-methyl-N'-cyanocarboxamidine, 2-thiazolinyl, pyrrolidinyl-N-cyanomethyleneimine, pyrrolidinyl-N-methylmethyleneimine, 1-pyrrolidinyl-2-nitrovinyl, carboxamidine, carboxyethylcarbonyl, pyrrolidinyl-N-methylsulphonylmethyleneimine, (2-carboxy)-phenylcarbonyl, aminosulphonyl, dimethylaminosulphonyl, carboxymethyl.

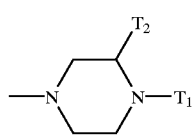

(c)

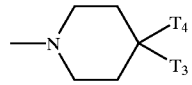

(d)

wherein T$_1$ together with T$_2$ and the atoms to which each is attached form an optionally substituted single or fused ring heterocyclic group and either T$_3$ together with T$_4$ form an optionally substituted single or fused ring heterocyclic group;

Suitably T$_1$ represents one of the following groups:

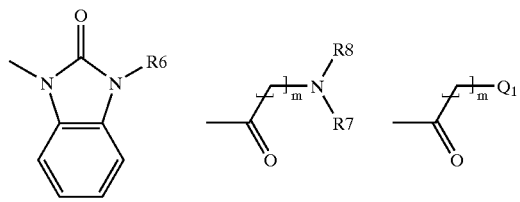

wherein R$_6$ represents H or a lower alkyl, preferably H or methyl, m is an integer from 1 to 5 and R$_7$ and R$_8$ represent a lower alkyl, preferably methyl or ethyl or together form an heterocycle, for example a piperidine, morpholine or optionally substituted piperazine.

Q$_1$ represents 2-phthalic acid, a saturated or unsaturated C1–6 carboxylic acid or an heterocycle for example 2-imidazolyl or thiazolyl.

In a group of formula (a), suitably T$_1$ represents also an heterocycle for example imidazolyl, thiazolyl, pyridyl, pyrimidyl, tetrazolyl or T$_1$ represents an optionally substituted carboxamidine or a corresponding quaternary carboxamidine derivative.

In a group of formula (a) suitable T$_1$ represents also one of the chemical entities below:

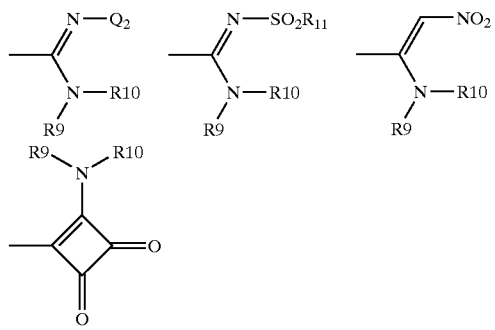

wherein R$_9$ and R$_{10}$ represent hydrogen, alkyl or together form a 5 to 7 membered ring with the N atom to which they are attached, preferably a pyrrolidin or piperidin ring and R$_{11}$ represents C$_{1-6}$ linear or branched alkyl or optionally substituted aryl wherein Q$_2$ is hydrogen, alkyl, aralkyl, aryl, cyano.

In a group of formula (a) suitable T1 represents also a sulphonamide of formula:

SO$_2$NR$_{12}$R$_{13}$ wherein R$_{12}$ and R$_{13}$ are independently selected from hydrogen; C$_{1-6}$ alkyl; optionally substituted aryl or R$_{12}$ and R$_{13}$ together with the nitrogen atom to which they are attached represent an optionally substituted N-linked single or fused ring heterocyclic group.

In one particular aspect —NY$_1$Y$_2$ is a moiety of formula (a).

In one particular aspect —NY$_1$Y$_2$ is a moiety of formula (b).

In one particular aspect —NY$_1$Y$_2$ is a moiety of formula (c).

In one particular aspect —NY$_1$Y$_2$ is a moiety of formula (d).

Suitably, R$_3$ is optionally substituted aryl, preferably an unsubstituted aryl group such as a phenyl group.

Suitably, R$_4$ is hydrogen.

Suitably, n is an integer from 1 to 6, favourably 1 to 4 and most preferably 1, 2 or 3.

Favourably, n' represents 1.

Favourably, n' represents 2.

Favourably, n' represents 3.

Preferred compounds of formula (I) are those wherein: Ar is phenyl or cyclohexyl, R is methyl, ethyl, or isopropyl, R$_1$ is hydrogen or methoxy or hydroxy, R$_2$ is a moiety (CH$_2$)$_n$ wherein n is 1, 2, 3 or 4, R$_3$ is phenyl and R$_4$ is hydrogen and NY$_1$Y$_2$ is:

(i) an optionally substituted piperazinyl group, especially a moiety of the above defined formula (a);

(ii) a moiety of the above defined formula (b); or (iii) a moiety of the above defined formula (c); or (iv) a moiety of the above defined formula (d). Further preferred compounds of formula (I) are those wherein: Ar is phenyl or cyclohexyl, R is methyl, ethyl or isopropyl, R$_1$ is hydrogen, methoxy or hydroxy R$_2$ is a moiety —(CH$_2$)$_n$— NY$_1$Y$_2$ wherein n is 1, R$_3$ is phenyl and R$_4$ is hydrogen and NY$_1$Y$_2$ is:

(i) an optionally substituted piperazinyl group, especially a moiety of the above defined formula (a); or (ii) a moiety of the above defined formula (b).

In particular should be mentioned the compounds of examples 20, 29, 32, 33, 34, 46, 47, 48, 53, 55, 62, 67, 78, 79, 80, 81 and 95.

The compounds of formula (I) may have at least one asymmetric centre—for example the carbon atom labelled with an asterisk (*) in the compound of formula (I)—and therefore may exist in more than one stereoisomeric form. The invention extends to all such stereoisomeric forms and to mixtures thereof, including racemates. In particular, the invention includes compounds wherein the asterisked carbon atom in formula (I) has the stereochemistry shown in formula (Ia):

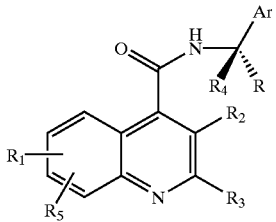

(Ia)

wherein Ar, R, R$_1$, R$_2$, R$_3$, R$_4$ and R$_5$ are as defined in relation to formula (I).

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), prefer-ably 75%, more preferably 90% and still more preferably 95% of the compound of formula (I) or its salt or solvate.

One preferred pharmaceutically acceptable form is the crystalline form, including such form in pharmaceutical composition. In the case of salts and solvates the additional ionic and solvent moieties must also be non-toxic.

Suitable salts are pharmaceutically acceptable salts.

Suitable pharmaceutically acceptable salts include the acid addition salts with the conventional pharmaceutical acids, for example maleic, hydrochloric, hydrobromic, phosphoric, acetic, fumaric, salicylic, citric, lactic, mandelic, tartaric, succinic, benzoic, ascorbic and methane-sulphonic.

Suitable pharmaceutically acceptable salts include salts of acidic moieties of the compounds of formula (I) when they are present, for example salts of carboxy groups or phenolic hydroxy groups.

Suitable salts of acidic moieties include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable solvates are pharmaceutically acceptable solvates.

Suitable pharmaceutically acceptable solvates include hydrates.

The term 'alkyl' (unless specified to the contrary) when used alone or when forming part of other groups (such as the 'alkoxy' group) includes straight- or branched-chain alkyl groups containing 1 to 12 carbon atoms, suitably 1 to 6 carbon atoms, examples include methyl, ethyl, n-propyl, isopropyl, n-butyl, isobutyl or tert-butyl group.

The term 'carbocylic' refers to cycloalkyl and aryl rings.

The term 'cycloalkyl' includes groups having 3 to 12, suitably 4 to 6 ring carbon atoms.

The term 'aryl' includes phenyl and naphthyl, preferably phenyl which unless specified to the contrary optionally comprise up to five, preferably up to three substituents selected from halogen, alkyl, phenyl, alkoxy, haloalkyl, hydroxyalkyl, hydroxy, amino, nitro, cyano, carboxy, alkoxycarbonyl, alkoxycarbonylalkyl, alkylcarbonyloxy, or alkylcarbonyl groups.

The term 'aromatic heterocyclic group' includes groups comprising aromatic heterocyclic rings containing from 5 to 12 ring atoms, suitably 5 or 6, and comprising up to four hetero-atoms in the or each ring selected from S, O or N.

Unless specified to the contrary, suitable substituents for any heterocyclic group includes up to 4 substituents selected from the group consisting of: alkyl, alkoxy, aryl and halogen or any two substituents on adjacent carbon atoms, together with the carbon atoms to which they are attached, may form an aryl group, preferably a benzene ring, and wherein the carbon atoms of the aryl group represented by the said two substituents may themselves be substituted or unsubstituted.

When used herein the term "halogen" refers to fluorine, chlorine, bromine and iodine, preferably fluorine, chlorine or bromine.

When used herein the term "acyl" includes residues of acids, in particular a residue of a carboxylic acid such as an alkyl- or aryl-carbonyl group.

The invention also provides a process for the preparation of a compound of formula (I), or a salt thereof and/or a solvate thereof, which process comprises reacting a compound of formula (II) or an active derivative thereof:

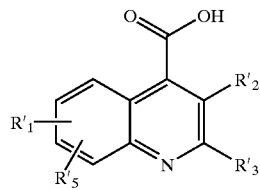

(II)

wherein $R'_1$, $R'_2$, $R'_3$ and $R'_5$ are $R_1$, $R_2$, $R_3$ and $R_5$ respectively as defined in relation to formula (I) or a group convertible to $R_1$, $R_2$, $R_3$ and $R_5$ respectively; with a compound of formula (III):

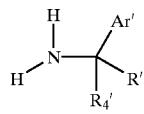

(III)

wherein R', $R_4'$ and Ar' are R, $R_4$ and Ar as defined for formula (I) or a group or atom convertible to R, $R_4$ and Ar respectively; to form a compound of formula (Ib):

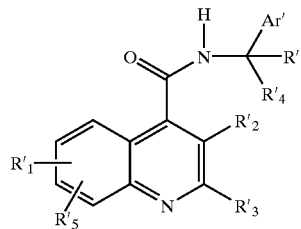

(Ib)

wherein Ar', R', $R'_1$, $R'_2$, $R'_3$, $R'_4$ and $R'_5$ are as defined above, and thereafter carrying out one or more of the following optional steps:
(i) converting any one of Ar', R', $R'_1$, $R'_2$, $R'_3$, $R'_4$ and $R'_5$ to Ar, R, $R_1$, $R_2$, $R_3$, $R_4$ or $R_5$ respectively as required, to obtain a compound of formula (I);
(ii) converting a compound of formula (I) into another compound of formula (I); and
(iii) preparing a salt of the compound of formula (I) and/or a solvate thereof.

Suitable groups convertible into other groups include protected forms of said groups.

Suitably Ar', R', $R'_1$, $R'_2$, $R'_3$, $R'_4$ or $R'_5$ each represents Ar, R, $R_1$, $R_2$, $R_3$, $R_4$ or $R_5$ respectively or a protected form thereof.

It is favoured if the compound of formula (II) is present as an active derivative.

A suitable active derivative of a compound of formula (II) is a transient activated form of the compound of formula (II) or a derivative wherein the carboxy group of the compound of formula (II) has been replaced by a different group or atom, for example by an acyl halide, preferably a chloride, or an acylazide or a carboxylic acid anhydride.

Other suitable active derivatives include: a mixed anhydride formed between the carboxyl moiety of the compound of formula (II) and an alkyl chloroformate; an activated ester, such as a cyanomethyl ester, thiophenyl ester, p-nitrophenyl ester, p-nitrothiophenyl ester, 2,4,6-trichlorophenyl ester, pentachlorophenyl ester, pentafluorophenyl ester, N-hydroxy-phtalimido ester, N-hydroxypiperidine ester, N-hydroxysuccinimide ester, N-hydroxy benzotriazole ester; alternatively, the carboxy group of the compound of formula (II) may be activated using a carbodiimide or N,N'-carbonyldiimidazole.

The reaction between the compound of formula (II) or the active derivative thereof and the compound of formula (III) is carried out under the appropriate conventional conditions for the particular compounds chosen. Generally, when the compound of formula (II) is present as an active derivative the reaction is carried out using the same solvent and conditions as used to prepare the active derivative, preferably the active derivative is prepared in situ prior to forming the compound of formula (Ib) and thereafter the compound of formula (I) or a salt thereof and/or a solvate thereof is prepared.

For example, the reaction between an active derivative of the compound of formula (II) and the compound of formula (III) may be carried out:

(a) by first preparing an acid chloride and then coupling said chloride with the compound of formula (III) in the presence of an inorganic or organic base in a suitable aprotic solvent such as dimethylformamide (DMF) at a temperature in a range from −70 to 50° C. (preferably in a range from −10 to 20° C.); or (b) by treating the compound of formula (II) with a compound of formula (III) in the presence of a suitable condensing agent, such as for example N,N'-carbonyl diimidazole (CDI) or a carbodiimide such as dicyclohexylcarbodiimide (DCC) or N-dimethylaminopropyl-N'-ethylcarbodiimide, preferably in the presence of N-hydroxybenzotriazole (HOBT) to maximise yields and avoid racemization processes (see *Synthesis*, 453, 1972), or O-benzotriazol-1-yl-N,N,N',N'-tetramethyluroniumhexafluorophosphate (HBTU), in an aprotic solvent, such as a mixture of acetonitrile (MeCN) and tetrahydrofuran (THF), for example a mixture in a volume ratio of from 1:9 to 7:3 (MeCN:THF), at any temperature providing a suitable rate of formation of the required product, such as a temperature in the range of from −70 to 50° C., preferably in a range of from −10 to 25° C., for example at 0° C.

A preferred reaction is set out in Scheme 1 shown below:

Scheme 1

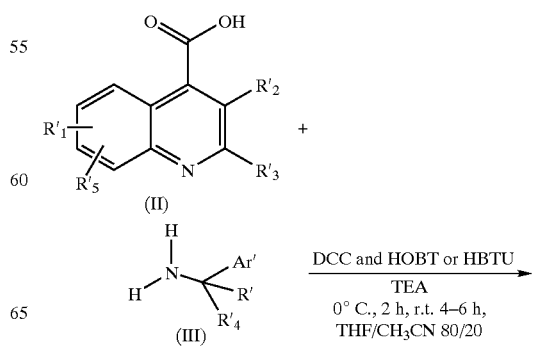

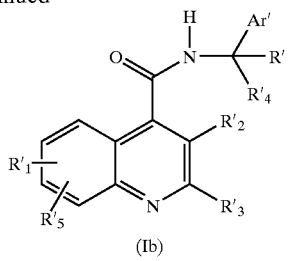

(Ib)

wherein Ar', R', R'$_1$, R'$_2$, R'$_3$, R'$_4$ and R'$_5$ are as defined above.

It will be appreciated that a compound of formula (Ib) may be converted to a compound of formula (I), or one compound of formula (I) may be converted to another compound of formula (I) by interconversion of suitable substituents. Thus, certain compounds of formula (I) and (Ib) are useful intermediates in forming other compounds of the present invention.

Accordingly, in a further aspect the invention provides a process for preparing a compound of formula (I), or a salt thereof and/or a solvate thereof, which process comprises converting a compound of the above defined formula (Ib) wherein at least one of Ar', R', R'$_1$, R'$_2$, R'$_3$, R'$_4$ or R'$_5$ is not Ar, R, R$_1$, R$_2$, R$_3$, R$_4$ or R$_5$ respectively, thereby to provide a compound of formula (I); and thereafter, as required, carrying out one or more of the following optional steps:
(i) converting a compound of formula (I) into another compound of formula (I); and
(ii) preparing a salt of the compound of formula (I) and/or a solvate thereof.

Suitably, in the compound of formula (Ib) the variables Ar', R', R'$_1$, R'$_2$, R'$_3$, R'$_4$ and R'$_5$ are Ar, R, R$_1$, R$_2$, R$_3$, R$_4$ or R$_5$ respectively or they are protected forms thereof.

The above mentioned conversions, protections and deprotections are carried out using the appropriate conventional reagents and conditions and are further discussed below.

A compound of formula (II) or the corresponding alkyl (such as methyl or ethyl) ester wherein n is an integer 1, is prepared by reacting a compound of formula (IV) or the corresponding alkyl (such as methyl or ethyl) ester:

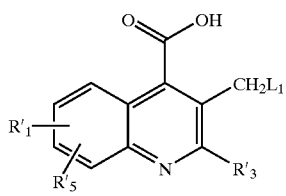

(IV)

wherein R'$_1$, R'$_3$ and R'$_5$ are as defined above and L$_1$ represents a halogen atom such as a bromine atom, with a compound of formula (V):

 (V)

wherein Y'$_1$ and Y'$_2$ are respectively Y$_1$ and Y$_2$ as defined in relation to formula (I) or protected forms thereof.

Suitably, Y'$_1$ and Y'$_2$ are Y$_1$ and Y$_2$.

Suitably, reaction between the compounds of formulae (IV) or the corresponding alkyl (such as methyl or ethyl) ester and (V) is carried out under conventional amination conditions, for example when L$_1$ is a bromine atom then the reaction is conveniently carried out in an aprotic solvent, such as tetrahydrofuran or dimethylformamide at any temperature providing a suitable rate of formation of the required product, usually at ambient temperature; preferably the reaction is carried out in the presence of triethylamine (TEA) or K$_2$CO$_3$.

A compound of formula (IV) or the corresponding alkyl (such as methyl or ethyl) ester is prepared by appropriate halogenation of a compound of formula (VI) or the corresponding alkyl (such as methyl or ethyl) ester:

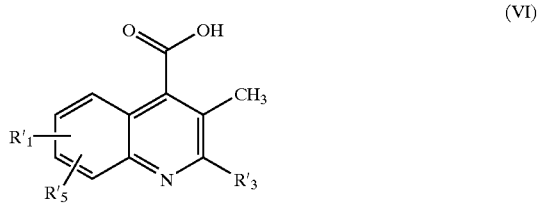

(VI)

wherein R'$_1$, R'$_3$ and R'5 are as defined above in relation to formula (II).

Suitable halogenation reagents are conventional reagents depending upon the nature of the halogen atom required, for example when L$_1$ is bromine a preferred halogenation reagent is N-bromosuccinimide (NBS).

The halogenation of the compound of formula (VI) or the corresponding alkyl (such as methyl or ethyl) ester is carried out under conventional conditions, for example bromination is carried out by treatment with NBS in an inert solvent, such as 1,2-dichloroethane or CH$_3$CN, at any temperature providing a suitable rate of formation of the required product, suitably at an elevated temperature such as a temperature in the range of 60° C. to 100° C., for example 80° C.; preferably the reaction is carried out in the presence of a catalytic amount on benzoyl peroxide.

In the case in which the corresponding alkyl (such as methyl or ethyl) ester of compounds (VI), (IV) and (II) are utilised, an hydrolysis to compound (II) is required before conversion to compound (Ib) in Scheme 1. Such hydrolysis can be carried out under acidic conditions, such 10–36% hydrochloric acid at a temperature in the range between 30 and 100° C. A compound of formula (II) wherein R'$_2$ represents —(CH$_2$)$_{2-9}$—NY$_1$Y$_2$, is conveniently prepared by reacting a compound of formula (VII):

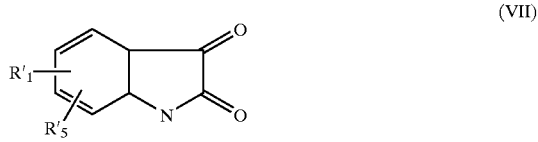

(VII)

wherein R'$_1$ and R'5 are as defined in relation to formula (II), with a compound of formula (VIII):

 (VIII)

wherein R'$_3$ is as defined in relation to formula (II), and T$_5$ is a group —NY$_1$Y$_2$ as defined in relation to formula (I) or a protected form thereof or a group convertible thereto, and p is an integer in the range of 2 to 9; and thereafter as required removing any protecting group and/or converting any group T$_5$ to NY$_1$Y$_2$.

The reaction between the compounds of formula (VII) and (VIII) is conveniently carried out using Pfitzinger reaction conditions (see for example J. Prakt. Chem. 33, 100 (1886), J. Prakt. Chem. 38, 582 (1888), J. Chem. Soc. 106 (1948) and Chem. Rev. 35, 152 (1944)), for example in an alkanolic solvent such as ethanol, at any temperature providing a suitable rate of formation of the required product, but generally at an elevated temperature, such as the reflux temperature of the solvent, and preferably in the presence of a base such as potassium hydroxide or potassium tert-butoxide.

Protected forms of —$NY_1Y_2$ will vary according to the particular nature of the group being protected but will be chosen in accordance with normal chemical practice.

Groups convertible to —$NY_1Y_2$ include groups dictated by conventional chemical practice to be required and to be appropriate, depending upon the specific nature of the —$NY_1Y_2$ consideration.

Suitable deprotection methods for deprotecting protected forms of $NY_1Y_2$ and conversion methods for converting $T_5$ to $NY_1Y_2$ will be those used conventionally in the art depending upon the particular groups under consideration with reference to standard texts such as Greene, T. W. and Wuts, P. G. M. Protective Groups in Organic Synthesis, John Wiley & Sons Inc. New York, 1991 (Second Edt.) or in Kocienski, P. J. Protecting groups. George Thieme Verlag, New York, 1994 and Chemistry of the Amino Group, Patais (Ed.), Interscience, New York 1968; or Advanced Organic Chemistry, March J, John Wiley & Sons, New York, 1992.

A compound of formula (VIII) is prepared from a compound of formula (IX):

$$R_3'—CO—CH_2—(CH_2)_p—OH \qquad (IX)$$

wherein $R'_3$ is as defined in relation to formula (II) and p is as defined in relation to formula (VIII), by first halogenating, preferably brominating, or mesylating the compound of formula (IX) and thereafter reacting the halogenation or mesylation product so formed with a compound capable of forming a group $T_5$ so as to provide the required comound of formula (VII).

When $T_5$ is a group —$NY_1Y_2$, a compound capable of forming a group $T_5$, is a compound of the above defined formula (V).

The halogenation of the compound of formula (IX) is suitably carried out using a conventional halogenation reagent. Mesylation is conveniently carried out using mesyl chloride in an inert solvent such as methylene dichloride, at a temperature below room temperature, such as 0° C., preferably in the presence of triethylamine. The reaction conditions between the compound of formula (IX) and the compound capable of forming a group $T_5$ will be those conventional conditions dictated by the specific nature of the reactants, for example when the $T_5$ required is a group $NY_1Y_2$ and the required compound capable of forming a group $T_5$ is a compound of the above defined formula (V), then the reaction between the halogenation or mesylation product of the compound of formula (IX) and the compound of formula (V) is carried out under analogous conditions to those described for the reaction between the compounds of formulae (IV) and (V).

Other compounds capable of forming a group $T_5$ will depend upon the particular nature of $T_5$, but will be those appropriate compounds dictated by conventional chemical practice with reference to standard texts such as Chemistry of the Amino Group, Patais (Ed.), Interscience, New York 1968; and Advanced Organic Chemistry, March J, John Wiley & Sons, New York, 1992.

A compound of formula (IX) may be prepared by reacting a compound of formula (X):

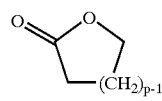

(X)

wherein p is as defined in relation to formula (VIII), with a lithium salt of formula (XI):

$$R'_3Li \qquad (XI)$$

wherein $R'_3$ is as defined in relation to formula (II).

The reaction between the compounds of formulae (X) and (XI) can be carried out in an aprotic solvent, such as diethyl-ether at any temperature providing a suitable rate of formation of the required product, usually at a low temperature such as in the range of –10° C. to –30° C., for example –20° C.

The compounds of formula (III) are known commercially available compounds or they can be prepared from known compounds by known methods, or methods analogous to those used to prepare known compounds, for example the methods described in Liebigs Ann. der Chemie, (1936), 523, 199.

Chiral compound of formula (III) wherein Ar is a $C_5$ or $C_7$ cycloalkyl group, R is methyl and $R_4$ is H are described in J. Org. Chem. (1996), 61 (12), 4130–4135. A chiral compound of formula (III) wherein Ar is phenyl, R is isopropyl and $R_4$ is H is a known compound described in for example Tetrahedron Lett. (1994), 35(22), 3745–6.

The compounds of formula (V) are known, commercially available compounds or they can be prepared using methods analogous to those used to prepare known compounds; for example the methods described in the Chemistry of the Amino Group, Patais (Ed.), Interscience, New York 1968; Advanced Organic Chemistry, March J, John Wiley & Sons, New York, 1992 ; J. Heterocyclic Chem. (1990), 27, 1559; Synthesis (1975), 135, Bioorg. Med. Chem. Lett. (1997), 7, 555, or Protective Groups in Organic Synthesis (second edition), Wiley Interscience, (1991) or other methods mentioned herein.

4-amino substituted piperidines are generally prepared by reductive amination of 4oxo-piperidine, or a 4-oxo-piperidine N-substituted with an appropriated protecting group, with an appropriate amine. Typical examples can be found in J. Org. Chem. (1990), 55 (8), 2552–4 or ibid. (1995), 60 (15), 4928–9.

Certain diazaspirononane intermediates used herein are known compounds, for example that used to prepare example 68 is described in J. Med. Chem. (1990), 33 (8), 2270–2275.

The condensation of succinic and phthalic anhydrides used to generate examples 83 and 85–87 is described in J. Indian Chem. Soc. (1979), 56 (2), 171–2. 4-Heterocyclic substituted piperidine as used for the preparation of example 77 are described in U.S. Pat. Nos. 4,329,348A1 9,820,511.

The compounds of formula (VII) are known compounds or they are prepared according to methods used to prepare known compounds for example those disclosed in J. Org. Chem. 21, 171 (1955); J. Org. Chem. 21, 169 (1955).

The compounds of formula (X) and (XI) are known compounds or they are prepared according to methods used to prepare known compounds for example those disclosed by Krow G. R. in Organic Reactions, Vol 43, page 251, John Wiley & Sons Inc. 1994 (for the compounds of formula (X)) and Organometallics in Synthesis, Schlosser M.(Ed), John Wiley & Sons Inc. 1994 (for the compounds of formula (XI)).

Compounds of formula (I) wherein $R_2$ represents a moiety $-(CH_2)_n-NY_1Y_2$ and $-NY_1Y_2$ is a piperazinyl group of formula (a) can suitably be prepared by reacting a compound of formula XII

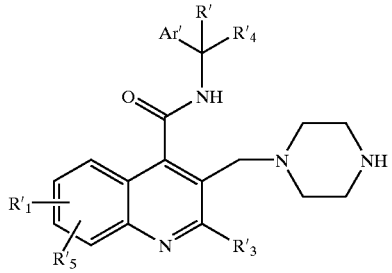

(XII)

wherein Ar', R', $R'_1$, $R'_2$, $R'_3$, $R'_4$ and $R'_5$ are as defined above, with reactive species of formula (XIII), for example:

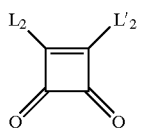

XIIIa

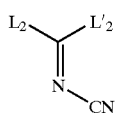

XIIIb

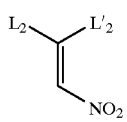

XIIIc

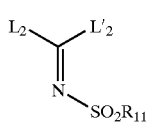

XIIId wherein $L_2$ and $L'_2$ represent leaving groups such as —SAlkyl or —OAlkyl, preferably —SCH$_3$ and —OButyl and $R_{11}$ is as defined above.

Mono substitution of compounds of formula (XIII) by a compound of formula (XII) generates news structures bearing still one leaving group, $L'_2$, which can then be reacted with compounds of formula:

$HNR_9R_{10}$ wherein $R_9$ and $R_{10}$ are as defined above to give the final compounds of formula (I).

Substituted carboxamidinopiperazines are best prepared by reacting compounds of formula (XII) with substituted isothiocyanates following scheme 2

Scheme 2

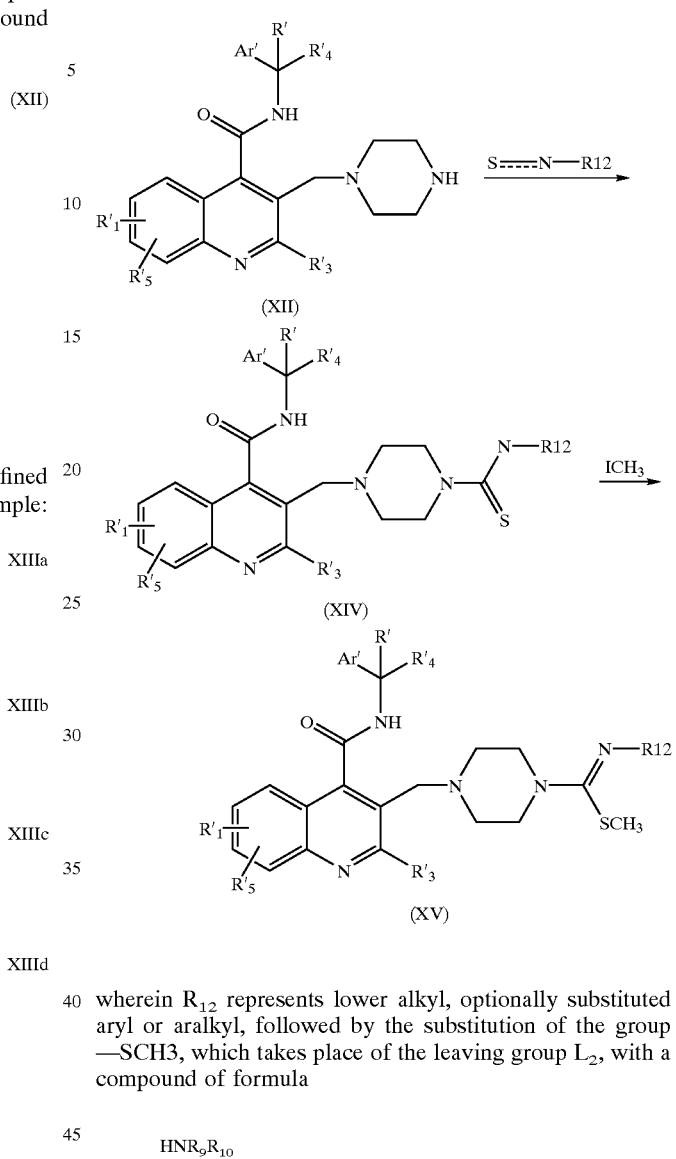

wherein $R_{12}$ represents lower alkyl, optionally substituted aryl or aralkyl, followed by the substitution of the group —SCH3, which takes place of the leaving group $L_2$, with a compound of formula $HNR_9R_{10}$ as mentioned above.

Unsubstituted carboxamidinopiperazines of formula (XVI)

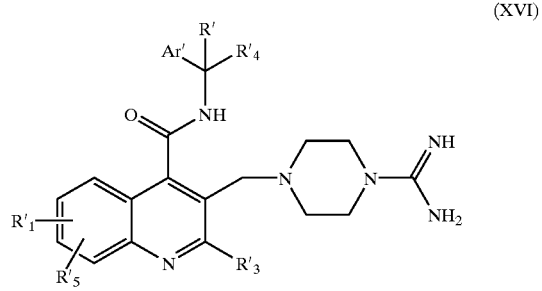

(XVI)

are prepared by reacting a compound of formula (XII) with the benzotriazole derivative of formula (XVII).

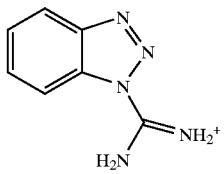 (XVII)

(Dimethylaminolethylene)dimethylammonium piperazines of formula (XVIII)

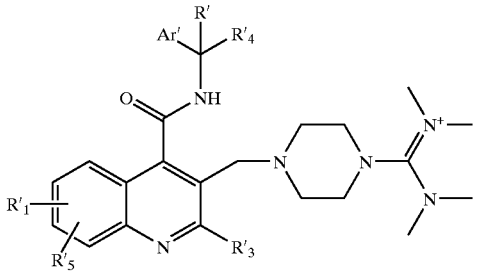 (XVIII)

are prepared by heating a compound of formula (XII) with HBTU in the presence of a base, for example TEA, in an appropriate solvent, usually one, or a mixture, of those used in peptide coupling reactions. Compounds of formula (I) wherein $R_2$ represents a moiety —$(CH_2)_n$—$NY_1Y_2$ and —$NY_1Y_2$ is a piperazinyl group of formula (a) wherein T1 represents carboxy, alkoxycarbonyl, optionally substituted alkyl, optionally substituted aryl, aralkyl, cycloalkyl, can suitably be prepared by reacting a compound of formula XII with a compound of formula $T_1L_3$ Wherein $T_1$ represents one of the radicals defined as above and L3 a leaving group for example halogen or sulfonate, preferably chlorine, bromine or mesylate. Compounds of formula (XII) are prepared by removing the protective group of a compound of formula (XIX)

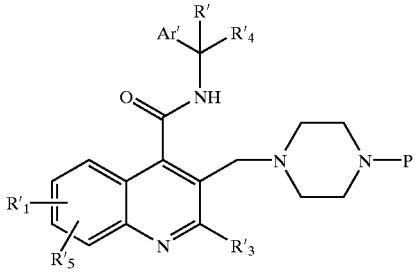 (XIX)

wherein Ar', R', $R'_1$, $R'_2$, $R'_3$, $R'_4$ and $R'_5$ are as defined above and P is an amine protective group, for example fmoc or benzyl, preferably fmoc. The protective group is removed by standard methods described in the literature, for example the fmoc residue is splitted by action of piperidine at room temperature in a solvent like acetonitrile. As hereinbefore mentioned, the compounds of formula (I) may exist in more than one stereoisomeric form—and the process of the invention may produce racemates as well as enantiomerically pure forms. Accordingly, a pure enantiomer of a compound of formula (I) is obtained by reacting a compound of the above defined formula (II) with an appropriate enantiomerically pure primary amine of formula (IIIa) or (IIIc):

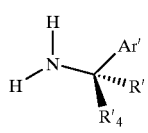 (IIIa)

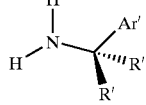 (IIIc)

wherein R', $R'_4$ and Ar' are as defined above, to obtain a compound of formula (I'a) or (I'c):

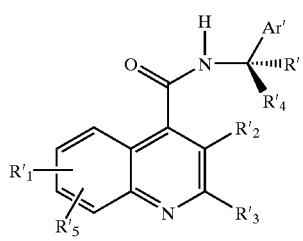 (I'a)

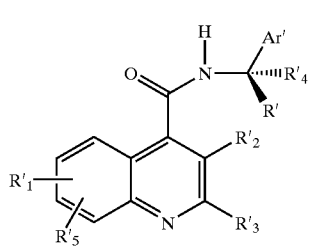 (I'c)

wherein Ar', R', $R'_1$, $R'_2$, $R'_3$, $R'_4$ and $R'_5$ are as defined above.

Compounds of formula (I'a) or (I'c) may subsequently be converted to compounds of formula (Ia) or (Ic) by the methods of conversion mentioned before:

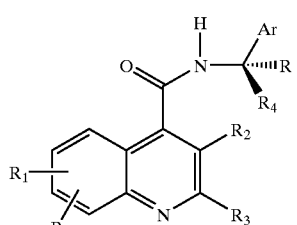 (Ia)

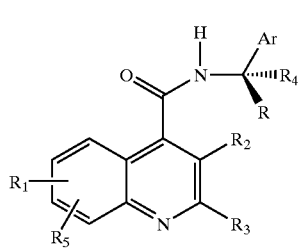 (Ic)

wherein Ar, R, $R_1$ $R_2$, $R_3$, $R_4$ and $R_5$ are as defined above.

Suitably, in the above mentioned compounds of formulae (Ia), (Ic), (I'a), (I'c), (IIIa) and (IIIc) $R_4$ represents hydrogen.

An alternative method for separating optical isomers is to use conventional, fractional separation methods in particular fractional crystallization methods. Thus, a pure enantiomer of a compound of formula (I) is obtained by fractional crystallisation of a diastereomeric salt formed by reaction of the racemic compound of formula (I) with an optically active strong acid resolving agent, such as camphosulphonic acid, in an appropriate alcoholic solvent, such as ethanol or methanol, or in a ketonic solvent, such as acetone. The salt formation process should be conducted at a temperature between 20° C. and 80° C., preferably at 50° C.

In the case in which other basic functionalities, such as primary, secondary or tertiary amine, are present in the molecule, a wider range of optically active acid resolving agents become available, including tartaric acid, O,O'-di-p-toluoyltartaric acid and mandelic acid.

A suitable conversion of one compound of formula (I) into a further compound of formula (I) involves converting one group $R_2$ into another group $R_2$ by for example:
(i) converting a ketal into a ketone, by such as mild acidic hydrolysis, using for example dilute hydrochloric acid;
(ii) reducing a ketone to a hydroxyl group by use of a borohydride reducing agent;
(iii) converting a carboxylic ester group into a carboxyl group using basic hydrolysis; and/or
(iv) reducing a carboxylic ester group to a hydroxymethyl group, by use of a borohydride reducing agent.

As indicated above, where necessary, the conversion of any group Ar', R', $R'_1$ $R'_2$, $R'_3$, $R'_4$ and $R'_5$ into Ar, R, $R_1$, $R_2$, $R_3$, $R_4$ or $R_5$ which as stated above are usually protected forms of Ar, R, $R_1$, $R_2$, $R_3$, $R_4$ or $R_5$ may be carried out using appropriate conventional conditions such as the appropriate deprotection procedure.

It will be appreciated that in any of the above mentioned reactions any reactive group in the substrate molecule may be protected and deprotected according to conventional chemical practice, for example as described by Greene, T. W. and Wuts, P.G.M. Protective Groups in Organic Synthesis, John Wiley & Sons Inc. New York, 1991 (Second Edt.) or in Kocienski, P. J. Protecting groups. George Thieme Verlag, New York, 1994.

Suitable protecting groups in any of the above mentioned reactions are those used conventionally in the art. Thus, for example suitable hydroxyl protecting groups include benzyl or trialkylsilyl groups.

The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter, if required, the benzyl group may be conveniently removed using catalytic hydrogenation or a mild ether cleavage reagent such as trimethylsilyl iodide or boron tribromide.

As indicated above, the compounds of formula (I) have useful pharmaceutical properties.

Accordingly the present invention also provides a compound of formula (I), or a pharmaceutically acceptable salt or solvate thereof, for use as an active therapeutic substance.

In particular, the present invention also provides a compound of formula (I), or a pharmaceutically acceptable salt or solvate thereof, for the treatment or prophylaxis of the Primary and Secondary Conditions.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of the Primary and Secondary Conditions.

As mentioned above the Primary conditions include respiratory diseases, such as chronic obstructive pulmonary disease (COPD), asthma, airway hyperreactivity, cough; inflammatory diseases such as inflammatory bowel disease, psoriasis, fibrositis, osteoarthritis, rheumatoid arthritis and inflammatory pain; neurogenic inflammation or peripheral neuropathy, allergies such as eczema and rhinitis; ophthalmic diseases such as ocular inflammation, conjunctivitis, vernal conjuctivitis and the like; cutaneous diseases, skin disorders and itch, such as cutaneous wheal and flare, contact dermatitis, atopic dermatitis, urticaria and other eczematoid dermatitis; adverse immunological reactions such as rejection of transplanted tissues and disorders related to immune enhancement or suppression such as systhemic lupus erythematosis; gastrointestinal (GI) disorders and diseases of the GI tract such as disorders associated with the neuronal control of viscera such as ulcerative colitis, Crohn's disease, irritable bowel syndrome (IBS), gastroexophageous reflex disease (GERD); urinary incontinence and disorders of the bladder function; renal disorders.

As mentioned above, the Secondary conditions include disorders of the central nervous system such as anxiety, depression, psychosis and schizophrenia; neurodegenerative disorders such as AIDS related dementia, senile dementia of the Alzheimer type, Alzheimer's disease, Down's syndrome, Huntington's disease, Parkinson's disease, movement disorders and convulsive disorders (for example epilepsy); demyelinating diseases such as multiple sclerosis and amyotrophic lateral sclerosis and other neuropathological disorders such as diabetic neuropathy, AIDS related neuropathy, chemotherapy-induced neuropathy and neuralgia; addiction disorders such as alcoholism; stress related somatic disorders; reflex sympathetic dystrophy such as shoulder/hand syndrome; dysthymic disorders; eating disorders (such as food intake disease); fibrosing and collagen diseases such as scleroderma and eosinophilic fascioliasis; disorders of the blood flow caused by vasodilation and vasospastic diseases such as angina, migraine and Reynaud's disease and pain or nociception, for example, that is attributable to or associated with any of the foregoing conditions especially the transmission of pain in migraine.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of the Primary and Secondary Conditions in mammals, particularly humans, which comprises administering to the mammal in need of such treatment and/or prophylaxis an effective, non-toxic pharmaceutically acceptable amount of a compound of formula (I) or a pharmaceutically acceptable salt or solvate thereof.

The activity of the compounds of the present invention, as $NK_3$ ligands, is determined by their ability to inhibit the binding of the radiolabelled $NK_3$ ligands, $[^{125}I]$-$[Me$-$Phe^7]$-NKB or $[^3H]$-Senktide, to guinea-pig and human $NK_3$ receptors (Renzetti et al, 1991, *Neuropeptide,* 18, 104–114; Buell et al, 1992, *FEBS,* 299(1), 90–95; Chung et al, 1994, *Biochem. Biophys. Res. Commun.,* 198(3), 967–972).

The binding assays utilized allow the determination of the concentration of the individual compound required to reduce by 50% the $[^{125}I]$-$[Me$-$Phe^7]$-NKB and $[^3H]$-Senktide specific binding to $NK_3$ receptor in equilibrium conditions (IC50).

Binding assays provide for each compound tested a mean $IC_{50}$ value of 2–5 separate experiments performed in duplicate or triplicate. The most potent compounds of the present invention show $IC_{50}$ values in the range 0.1–1000 nM. The $NK_3$-antagonist activity of the compounds of the present invention is determined by their ability to inhibit senktide-induced contraction of the guinea-pig ileum (Maggi et al, 1990, *Br. J. Pharmacol.,* 101, 996–1000) and rabbit isolated iris sphincter muscle (Hall et al., 1991, *Eur. J. Pharmacol.,* 199, 9–14) and human $NK_3$ receptors-mediated $Ca^{++}$ mobilization (Mochizuki et al, 1994, *J. Biol. Chem.,* 269, 9651–9658). Guinea-pig and rabbit in-vitro functional assays provide for each compound tested a mean $K_B$ value of 3–8 separate experiments, where $K_B$ is the concentration of the individual compound required to produce a 2-fold rightward shift in the concentration-response curve of senktide. Human receptor functional assay allows the determination of the concentration of the individual compound required to reduce by 50% ($IC_{50}$ values) the $Ca^{++}$ mobilization induced by the agonist NKB. In this assay, the compounds of the present invention behave as antagonists.

The activity of the compounds of the present invention, as NK-2 ligands, is determined by their ability to inhibit the binding of the radiolabelled NK-2 ligands, [$^{125}$I]-NKA or [$^3$H]-NKA, to human NK-2 receptors (Aharony et al, 1992, *Neuropeptide*, 23, 121–130).

The binding assays utilized allow the determination of the concentration of the individual compound required to reduce by 50% the [$^{125}$I]-NKA and [$^3$H]-NKA specific binding to NK2 receptor in equilibrium conditions ($IC_{50}$).

Binding assays provide for each compound tested a mean $IC_{50}$ value of 2–5 separate experiments performed in duplicate or triplicate. The most potent compounds of the present invention show $IC_{50}$ values in the range 0.5–1000 nM, such as 1–1000 nM. The NK-2-antagonist activity of the compounds of the present invention is determined by their ability to inhibit human NK-2 receptor-mediated $Ca^{++}$ mobilization (Mochizuki et al, 1994, *J. Biol. Chem.*, 269, 9651–9658). Human receptor functional assay allows the determination of the concentration of the individual compound required to reduce by 50% ($IC_{50}$ values) the $Ca^{++}$ mobilization induced by the agonist NKA. In this assay, the compounds of the present invention behave as antagonists.

The therapeutic potential of the compounds of the present invention in treating the conditions can be assessed using rodent disease models.

As stated above, the compounds of formula (I) are also considered to be useful as diagnostic tool. Accordingly, the invention includes a compound of formula (I) for use as diagnostic tools for assessing the degree to which neurokinin-3 and neurokinin-2 receptor activity (normal, overactivity or underactivity) is implicated in a patient's symptoms. Such use comprises the use of a compound of formula (I) as an antagonist of said activity, for example including but not restricted to tachykinin agonist-induced inositol phosphate turnover or electrophysiological activation, of a cell sample obtained from a patient. Comparison of such activity in the presence or absence of a compound of formula (I), will disclose the degree of NK-3 and NK-2 receptor involvement in the mediation of agonist effects in that tissue.

The following Descriptions illustrate the preparation of the intermediates, whereas the following Examples illustrate the preparation of the compounds of the invention.

DESCRIPTIONS AND EXAMPLES

DESCRIPTION A: 3-Methyl-2-phenyl-quinoline-4-carboxylic acid methyl ester 30 g (114 mmol) of 3-methyl-2-phenyl-quinoline-4-carboxylic acid (CAS [43071-45-0]) were suspended in 250 ml of dry $CH_2Cl_2$; 20 ml (230 mmol) of oxalyl chloride dissolved in 120 ml of $CH_2Cl_2$ were added dropwise and the reaction mixture was stirred at room temperature for 30 min. Two drops of N,N-dimethylformamide (DMIF) were added and the reaction was stirred for additional 30 min. The solvent was evaporated in vacuo to dryness, the residue was taken up with 100 ml of $CH_2Cl_2$ and 100 ml of MeOH, dissolved in 400 ml of $CH_2Cl_2$, were added dropwise. After stirring for 18 h, the solvent was evaporated in vacuo to dryness, the residue was taken up with $CH_2Cl_2$ and washed with 1% $NaHCO_3$; the organic layer was dried over $Na_2SO_4$, filtered and evaporated in vacuo to dryness to yield 31.6 g of the title compound as a solid, which was used in the following reaction without further purification.

$C_{18}H_{15}NO_2$ MW 277.31 MP=73–75° C. IR (KBr) 3441, 3051, 2954, 1731, 1582, 1556 $cm^{-1}$.

DESCRIPTION B: 3-Bromomethyl-2-phenyl-quinoline-4-carboxylic acid methyl ester 10 g (36 mmol) of 3-methyl-2-phenylquinoline-4-carboxylic acid methyl ester (compound of Description A) were dissolved in 500 ml of $CH_3CN$; 13 g (72 mmol) of N-bromosuccinimide were added and the reaction mixture was heated to reflux. After adding 1 g (4.1 mmol) of dibenzoylperoxide, the reaction was refluxed for 24 h; then additional 4 g (22.5 mmol) of N-bromosuccinimide and 0.5 g (2.0 mmol) of dibenzoylperoxide were added and the reaction was refluxed for 4 h. The solvent was evaporated in vacuo to dryness to yield 26.1 g of crude methyl 3-bromomethyl-2-phenylquinoline-4-carboxylate (theorical amount, 12.8 g) which was used in the following reaction without further purification.

$C_{18}H_{14}BrNO_2$ MW=356.23

DESCRIPTION 1: 3-[1,4']Bipiperidinyl-1'-ylmethyl-2-phenyl-quinoline-4-carboxylic acid methyl ester 5 g (14 mmol) of 3-bromomethyl-2-phenyl-quinoline-4-carboxylic acid methyl ester (compound of Description B), 2.9 g, (15.4 mmol) of 90% 4-piperidinopiperidine (Aldrich), 2.7 ml (15.4 mmol) diisopropylethyl amine were dissolved in 100 ml of dry THF and the mixture was stirred for one night at 50° C. The solvent was concentrated, the residue was dissolved in methylene chloride, washed with water, and the organic phase was dried over $MgSO_4$. After concentration of the solvent the residue was purified by flash chromatography over 160 g of silicagel (eluent $CH_2Cl_2$/MeOH/$NH_4OH$: 95/5/0.5) affording 3.5 g (yield 56%) of the title compound as a white solid.

$C_{28}H_{33}N_3O_2$ MW=443.59 δ ($CDCl_3$): 1.29–2.02(12H); 2.25(1H); 2.47(4H); 2.78(2H); 3.66(2H); 4.05(3H); 7.38–7.55(5Har); 7.58(1Har); 7.72(1Har); 7.88(1Har); 8.17 (1Har)ppm.

DESCRIPTION 2: 3-[1,4']Bipiperidinyl-1'-ylmethyl-2-phenyl-quinoline-4-carboxylic acid dihydrochloride 3.5 g (7.9 mmol) of 3-[1,4']bipiperidinyl-1'-ylmethyl-2-phenyl-quinoline-4-carboxylic acid methyl ester (compound of Description 1) and 50 ml 6N HCl are refluxed for 1.5 h. then concentrated to dryness. The residue is triturated in acetone. This process is re-applied twice to the solid thus obtained affording, after drying in vacuo 4.5 g of the title compound as a crude dihydrochloride used without further purification in the next step.

$C_{27}H_3N_3O_2$·2HCl MW=502.56 δ ($DMSOd_6$): 1.16–2.29 (10H); 2.62–3.38(8H); 4.46(2H); 5.77(1Hexch with $D_2O$); 7.45–8.30(9Har); 11.12 (1Hexch with $D_2O$)ppm.

DESCRIPTION 3: 2-Phenyl-3-(4-phenyl-piperidin-1-ylmethyl)quinoline-4-carboxylic acid methyl ester 5.4 g of crude 3-bromomethyl-2-phenyl-quinoline-4-carboxylic acid methyl ester (compound of Description B) were dissolved, under nitrogen atmosphere, in 30 ml of dry THF. The solution was cooled to 10° C. and 4.0 g (24.8 mmol) of 4-phenylpiperidine, dissolved in 5 ml of THF, were added dropwise. The reaction mixture was allowed to warm to room temperature and stirred overnight. Salts were filtered off and the filtrate was evaporated in vacuo to dryness, taken up with 2 N HCl and washed with EtOAc; the aqueous layer was basified with 10% NaOH and extracted with $CH_2Cl_2$. The organic layer was dried over $Na_2SO_4$, filtered and evaporated in vacuo to dryness to obtain a crude material which was purified by gradient flash column chromatography on 230–400 mesh silica gel, utilising a mixture of EtOAc/hexane 10:90 containing 0.5% $NH_4OH$ (28%) as starting eluent and a mixture of EtOAc/hexane 15:85 containing 0.5% $NH_4OH$ (28%) as final eluent. 3.0 g of the title compound were recovered as an off-white solid.

$C_{29}H_{28}N_2O_2$ MW=436.56 IR: (KBr) 3440, 3062, 2945, 1731, 1577, 1555 $cm^{-1}$.

DESCRIPTION 4: 2-Phenyl-3-(4-phenyl-piperidin-1-ylmethyl)-quinoline-4-carboxylic acid hydrochloride 3.0 g (6.87 mmol) of 2-phenyl-3-(4-phenyl-piperidin-1-ylmethyl)-quinoline-4-carboxylic acid methyl ester (compound of Description 3) were dissolved in 100 ml of 6 N HCl and refluxed for 1 h. Evaporation to dryness afforded 3.5 g of crude title compound, which was used in the following reaction without further purification.

$C_{28}H_{26}N_2O_2 \cdot HCl$ MW=459.00 MP=175–178° C. IR: (KBr) 3385, 3062, 2495, 1973, 1718, 1630 $cm^{-1}$.

DESCRIPTION 5: 3-(4-Isopropyl-piperazin-1-ylmethyl)-2-phenylquinoline-4-carboxylic acid methyl ester 7.8 g of crude 3-bromomethyl-2-phenyl-quinoline-4-carboxylic acid methyl ester (compound of Description B) were dissolved, under nitrogen atmosphere, in 130 ml of dry THF. The solution was cooled to 10° C. and 2.8 g (21.6 mmol) of 1-isopropylpiperazine, dissolved in 20 ml of THF, were added dropwise. The reaction mixture was allowed to warm to room temperature and stirred overnight. Salts were filtered off and the filtrate was evaporated in vacuo to dryness, taken up with 2 N HCl and washed with EtOAc; the aqueous layer was basified with 10% NaOH and extracted with $CH_2Cl_2$. The organic layer was dried over $Na_2SO_4$, filtered and evaporated in vacuo to dryness to obtain a crude material which was purified by flash column chromatography on 230–400 mesh silica gel, utilising a mixture of $Et_2O/iPr_2O$ 70:30 containing 0.3% $NH_4OH$ (28%). 3.8 g of the title compound were recovered as a yellow solid.

$C_{25}H_{29}N_3O_2$ MW=403.54 IR: (KBr) 3441, 3065, 2946, 1731, 1580, 1555 $cm^{-1}$.

DESCRIPTION 6: 3-(4-Isopropyl-piperazin-1-ylmethyl)-2-phenyl-quinoline-4-carboxylic acid dihydrochloride 3.8 g (9.42 mmol) of 3-(4-isopropyl-piperazin-1-ylmethyl)-2-phenyl-quinoline-4-carboxylic acid methyl ester (compound of Description 5) were dissolved in 100 ml of 6 N HCl and refluxed for 4 h. Evaporation to dryness afforded 4.0 g of crude title compound, which was used in the following reaction without further purification.

$C_{24}H_{27}N_3O_2 \cdot 2HCl$ MW=389.50 MP=177–180° C. IR: (KBr) 3408, 2928, 2666, 1716, 1632 $cm^{-1}$.

DESCRIPTION 7: (S)-1-Cyclohexyl-propylamine hydrochloride 2.0 g (14.8 mmol) of (S)-1-phenyl-propylamine were dissolved in 250 ml of a 4% solution of citric acid in $H_2O$. 0.6 g of 20% $Pd(OH)_2/C$ were added and the reaction mixture was hydrogenated in a steel autoclave at 50 bar and 60° C. for 24 h. The catalyst was filtered off, the filtrate was evaporated and the residue was taken up with 40% NaOH and extracted several times with $H_2O$. The combined organic layers were dried over $Na_2SO_4$ and acidified with $HCl/Et_2O$. Evaporation to dryness afforded 0.3 g of the title compound as a solid.

$C_9H_{19}N \cdot HCl$ MW=389.50

DESCRIPTION 8: 3-(4-Fmoc-piperazin-1-ylmethyl)-2-phenyl-quinoline-4-carboxylic acid methyl ester 6.6 g (18.5 mmol) of 3-bromomethyl-2-phenyl-quinoline-4-carboxylic acid methyl ester (compound of Description B) were reacted with 6.8 g (20 mmol) of Fmoc piperazine in 150 ml of THF following the procedure used in Description 3 and afforded 7.5 g (yield: 69%) of the title compound.

$C_{37}H_{33}N_3O_4$ MW=583.68 $^1H$ NMR δ ($DMSOd_6$): 1.99 (4H); 3.10(4H); 3.62(2H); 3.97(3H); 4.20(1H); 4.42(2H); 7.18–7.40(4Har); 7.45–7.92(12Har); 8.09(1Har)ppm.

DESCRIPTION 9: 3-(4-Fmoc-piperazin-1-ylmethyl)-2-phenyl-quinoline-4-carboxylic acid hydrochloride 7.5 g (13 mmol) of the ester of Description 8 are hydrolysed with 6 N aqueous hydrochloric acid following the procedure used in Description 4 affording 9.5 g of crude title compound which was used without purification in the next step.

$C_{36}H_{31}N_3O_4 \cdot HCl$ MW=606.12 $^1H$ NMR δ ($DMSOd_6$): 2.50(4H); 3.32(4H); 4.22(2H); 4.23(1H); 4.35(2H); 6.50 (1Hexch with $D_2O$); 7.22–7.88(14Har); 7.98(1Har); 8.17 (2Har)ppm.

DESCRIPTION 10: 3-(4-Fmoc-piperazin-1-ylmethyl)2-phenyl-quinoline-4-carboxylic acid ((S)-1-phenyl-propyl)-amide 5.35 g (8.3 mmol) of crude acid of Description 9 were condensed on 1.7 ml (12.5 mmol) of (S)-1-phenyl-propylamine following the procedure of Example 2 affording, after flash chromatography on silica gel, 3.2 g (56%) of the title compound.

$C_{45}H_{42}N_4O_3$ MW=686.86 $^1H$ NMR δ($DMSOd_6$): 0.94 (3H); 1.40–2.18(6H); 2.57–3.13(4H); 3.50(2H); 4.21(1H); 4.34(2H); 5.08(1H); 7.09–7.98(21Har); 8.03(1Har): 9.12 (1Hexch with $D_2O$)ppm.

DESCRIPTION 11: 3-(4-Fmoc-piperazin-1-ylmethyl)-2-phenyl-quinoline-4-carboxylic acid ((S)-1-cyclohexyl-ethyl)-amide 4.75 g (8.3 mmol) of crude acid of Description 9 were condensed on 1.65 ml (11 mmol) of (S)-1-cyclohexyl-ethylamine following the procedure of Example 2 affording, after flash chromatography on silica gel, 2.2 g (yield 43.9%) of the title compound.

$C_{44}H_{46}N_4O_3$ MW=678.87 $^1H$ NMR δ($DMSOd_6$): 0.95 (3H); 1.68–4.00(21H); 2.60(3H); 5.08(1H); 7.22–8.24 (13Har); 8.11(1Har); 9.32(1Hexch with D2O); 10.82 (2Hexch with $D_2O$)ppm.

DESCRIPTION 12: 3-(4-Fmoc-piperazin-1-ylmethyl)-2-phenyl-quinoline-4-carboxylic acid ((S)-2-methyl-1-phenyl-propyl)-amide 6.95 g (10.8 mmol) of crude acid of Description 9 were condensed on 2 g (13.5 mmol) of (S)-2-methyl-1-phenyl propylamine following the procedure of Example 2 affording, after flash chromatography on silica gel, 5.4 g (yield 71%) of the title compound.

$C_{46}H_{44}N_4O_3$ MW=700.86 $^1H$ NMR δ($CDCl_3$): 0.96(3H); 1.18(3H); 1.56–2.98(4H); 2.28(1H); 3.04(4H); 3.53(2H); 4.20(1H); 4.35(2H); 5.17(1H); 7.18–7.63(18Har); 7.74 (3Har); 7.97(1Hexch with $D_2O$); 8.14(1Har)ppm.

DESCRIPTION 13: 2-Phenyl-3-piperazin-1-ylmethyl-quinoline-4-carboxylic acid ((S)-2-methyl-1-phenyl-propyl)-amide 5.4 g (7.7 mmol) of the Fmoc derivative of Description 12 was reacted with 1.25 ml of piperidine in 200 ml acetonitrile, at room temperature for one night. The reaction mixture is concentrated to dryness and the residue was purified by flash chromatography on silicagel (eluant: $CH_2Cl_2/CH_3OH/NH_4OH$; 90/10/2), affording 2.55 g (yield 69.3%) of the title compound.

$C_{31}H_{34}N_4O$ MW=478.64 $^1H$ NMR δ($DMSOd_6$): 0.79 (3H); 1.06(3H); 1.49–2.55(9H); 3.45(2H and 1Hexch with D2O); 4.88(1H); 7.12–8.10(14Har); 9.16(1Hexch with $D_2O$)ppm.

DESCRIPTION 14: 2-Phenyl-3-piperazin-1-ylmethyl-quinoline-4-carboxylic acid ((S)-1-phenyl-propyl)-amide 2.75 g (41 mmol) of the Fmoc protected derivative of Description 12 afforded by applying the procedure of Description 13, 1.14 g (yield 60%) of the title compound.

$C_{30}H_{32}N_4O$ MW=464.61 $^1$H NMR δ (DMSOd$_6$): 0.94 (3H); 1.57–2.08(6H); 2.31(4H); 3.36(2H and 1Hexch with D$_2$O); 5.07(1H); 7.13–7.94(13Har); 8.01(1Har); 9.17 (1Hexch with D$_2$O)ppm.

DESCRIPTION 15: 3-[4-(1-Cyanoimino-1-methylsulfanyl-methyl)-piperazin-1-ylmethyl]-2-phenyl-quinoline-4carboxylic acid ((S)-1-cyclohexyl-ethyl)-amide 0.5 g (1.1 mmol) of 2-phenyl-3-piperazin-1-ylmethyl-quinoline-4-carboxylic acid ((S)-1-cyclohexyl-ethyl)-amide (compound of Example 34) and 0.16 g (1.1 mmol) of dimethyl N-cyanodithioiminocarbonate (Aldrich) were heated at reflux for 6 h in a mixture of 2.2 ml of DMF and 8.8 ml of EtOH. The solvent was concentrated and the residue purified by flash chromatography on silicagel (CH$_2$Cl$_2$/MeOH: 98/2) affording 0.56g (yield 91.8%) of the title compound which was used without purification in the following step.

$C_{33}H_{34}N_6OS$ MW=562.74 $^1$HNMR δ(CDCl$_3$): 1.00–1.39 (5H); 1.24(3H); 1.48(1H); 1.63–1.96(5H); 2.25(4H); 2.69 (3H); 3.57(4H); 3.72(2H); 4.25(1H); 6.42(1Hexch with D$_2$O; 7.38–7.55(5Har); 7.60(1Har); 7.75(1Har); 7.95(1Har); 8.14(1Har)ppm.

DESCRIPTION 16: 3-[4-(1-Methanesulfonylimino-1-methylsulfanyl-methyl)-piperazin-1-ylmethyl]-2-phenyl-quinoline-4-carboxylic acid ((S)-1-cyclohexyl-ethyl)-amide 0.48 g (1.05 mmol) of 2-phenyl-3-piperazin-1-ylmethyl-quinoline-4-carboxylic acid ((S)-1-cyclohexyl-ethyl)-amide (compound of Example 34) and 0.21 g (1.05 mmol) of carbonimidodithioic acid, (methylsulfonyl)-dimethyl ester (RN 13068-10-5) were heated at reflux for 5 h in a mixture of 2 ml of DMF and 8 ml of EtOH. The solvent was concentrated and the residue purified by flash chromatography on silicagel (CH$_2$Cl$_2$/MeOH: 97/3) affording 0.52 g of crude title compound which was used without purification in the following step.

$C_{33}H_{37}N_4O_3S_2$ MW=615.82 $^1$H NMR δ(CDC$_3$): 0.95–1.38(5H); 1.28(3H); 1.48(1H); 1.62–1.94(5H); 2.28 (4H); 2.47(3H); 3.01(3H); 3.54(4H); 3.59(2H); 4.25(1H); 6.52(1Hexch with D$_2$O); 7.36–7.53(5Har); 7.59(1Har); 7.75 (1Har); 7.95(1Har); 8.14(1Har)ppm.

DESCRIPTION 17: 4-[4((S)-1-Cyclohexyl-ethylcarbamoyl)-2-phenyl-quinolin-3-ylmethyl]-N-methyl-piperazine-1-carboximidothioic acid methyl ester 0.05 g (0.95 mmol) of 3-(4-methylthiocarbamoyl-piperazin-1-ylmethyl)-2-phenyl-quinoline-4-carboxylic acid ((S)-1-cyclohexyl-ethyl)-amide (compound of Example 75) was suspended in 5 ml acetone and 0.41 g (2.85 mmol) methyl iodide was added. After 4 h stirring at room temperature the mixture became clear. The solvent was concentrated and the residue triturated with di-ethyl ether affording, after filtration and drying, 0.63 g of the hydroiodide salt of the title compound. This compound was used without further purification in the next step.

$C_{33}H_{37}N_5OS$ MW=551.76 $^1$H NMR δ(DMSOd$_6$): 0.92–1.36(5H); 1.75(3H); 1.47(1H); 1.58–1.92(5H); 2.24 (4H); 2.46(3H); 3.05(3H); 3.36(4H); 3.63(2H); 4.02(1H); 7.36–7.91(8Har); 8.04(1Har); 8.55(1Hexch with D$_2$O)ppm.

DESCRIPTION 18: 3-(4-Oxo-piperidin-1-ylmethyl)-2-phenyl-quinoline-4-carboxylic acid ((S)-1-phenyl-propyl)-amide Starting from 3-bromomethyl-2-phenylquinoline-4-carboxylic acid methyl ester (compound of Description B) and 4-oxopiperidine, following the procedure of description 1, then applying procedures analogous to those described in description 2 and example 2 afforded the title compound after purification on silicagel (EtOAc/Heptane: 1/1).

$C_{31}H_{31}N_3O_2$ MW=477.60 $^1$H NMR δ(DMSOd$_6$): 0.83 (3H); 1.57–2.30(8H); 2.45(2H); 3.34–3.98(2H); 5.08(1H); 7.12–8.18(14Har); 9.21(1Hexch with D$_2$O)ppm.

DESCRIPTION 19: 4-tert-Butylsulfamoyl-piperazine-1-carboxylic acid tert-butyl ester 6.1 g (32.62 mmol) of piperazine-1-carboxylic acid tert-butyl ester (RN 76535-74-5) were dissolved in 150 ml of CH$_2$Cl$_2$ and 4.5 g (32.6 mmol) of K$_2$CO$_3$ were added. The mixture was cooled to 0° C. and 5.6 g (32.62 mmol) of tert-butyl-sulfamoylchloride (prepared according to Catt, J. D. JOC, 1974, 39, 566–8) dissolved in 50 ml of CH$_2$Cl$_2$ were added dropwise and the reaction mixture was stirred at room temperature for 2 h. 50 ml of water were added, the two phase separated in a separatory funnel and the aqueous phase extracted with CH$_2$Cl$_2$. The organic phases were collected, dried over Na$_2$SO$_4$ and evaporated in vacuo to dryness to yield 4.6 g of the title compound as a yellow solid $C_{13}H_{27}N_3O_4S$ MW=321.43 IR: (KBr) 3273, 2971, 1701, 1364, 1137, 1023, 934, 768 cm$^{-1}$.

DESCRIPTION 20: 4-Dimethylsulfamoyl-piperazine-1-carboxylic acid tert-butyl ester Prepared as described in Description 19 from 10.38 g (55.7 mmol) of piperazine-1-carboxylic acid tert-butyl ester (RN 76535-74-5), 7.7 g (55.7 mmol) of K$_2$CO$_3$ and 8 g (55.7 mmol) of dimethyl-sulfamoylchloride 15.2 g of the title compound were obtained as a yellow solid $C_{11}H_{23}N_3O_4S$ MW=293.39 IR: (KBr) 2979, 2866, 1687, 1142, 952, 752 cm$^{-1}$.

DESCRIPTION 21: Piperazine-1-sulfonic acid tert-butylamide 4.6 g (14.3 mmol) of 4-tert-butylsulfamoyl-piperazine-1-carboxylic acid tert-butyl ester (compound of Description 19) were dissolved in 10 ml of CH$_2$Cl$_2$ and 50 ml of 30% ethereal HCl were added. The solution was stirred at room temperature for 2 h. The solvent was evaporated in vacuo to dryness yielding 1.5 g of the title compound as a white solid $C_8H_{19}N_3O_2S$ MW=221.32 IR: (KBr) 3207, 2730, 1591, 1326, 1143, 1001, 917, 720, 631 cm$^{-1}$.

DESCRIPTION 22: Piperazine-1-sulfonic acid dimethylamide 13 g (44.31 mmol) of 4-dimethylsulfamoyl-piperazine-1-carboxylic acid tert-butyl ester (compound of Description 20) were dissolved in 100 ml of CH$_2$Cl$_2$ and 20 ml of 30% ethereal HCl were added. The solution was stirred at room temperature for 2 h. The solvent was evaporated in vacuo to dryness yielding 9.2 g of the title compound as a white solid $C_6H_{15}N_3O_2S$ MW=193.27 IR: (KBr) 2786, 1688, 1356, 1152, 1037, 942, 867, 737,677 cm$^{-1}$.

DESCRIPTION 23: 3-(4-tert-Butylsulfamoyl-piperazin-1-ylmethyl)-2-phenyl-quinoline-4-carboxylic acid methyl ester 1.5 g (6.78 mmol) of piperazine-1-sulfonic acid tert-butylamide (compound of Description 21) and 0.94 g (6.78 mmol) of K$_2$CO$_3$ were suspended in 70 ml of CH$_3$CN. 2.42 g (6.78 mmol) of 3-bromomethyl-2-phenylquinoline-4-carboxylic acid methyl ester (compound of Description B) were dissolved in 30 ml of CH$_3$CN and the solution was added to the previous suspension. The resulting mixture was stirred at room temperature for 4 h. The solvent was evaporated in vacuo to dryness, the residue was taken up with 6N HCl and washed with EtOAc. The aqueous phase was basified with 1 N NaOH and extracted with EtOAc. The organic phase was dried over Na$_2$SO$_4$ and evaporated to dryness to yield a 3.0 of crude title compound used without further purification $C_{26}H_{32}N_4O_4S$ MW=496.63 IR: (KBr) 3280, 2974, 1734, 1575, 1555, 1444, 1220, 1146, 940 764 cm$^{-1}$.

DESCRIPTION 24: 3-(4-Dimethylsulfamoyl-piperazin-1-ylmethyl)-2-phenyl-quinoline-4-carboxylic acid methyl ester 1.6 g (8.24 mmol) of piperazine-1-sulfonic acid dimethylamide (compound of Description 22) and 1.16 g (8.42 mmol) of $K_2CO_3$ were suspended in 70 ml of $CH_3CN$. 3.0 g (8.42 mmol) of 3-bromomethyl-2-phenylquinoline-4-carboxylic acid methyl ester (compound of Description B) were dissolved in 30 ml of $CH_3CN$ and the solution was added to the previous suspension. The resulting mixture was stirred at room temperature for 4 h. The solvent was evaporated in vacuo to dryness, the residue was taken up with 6N HCl and washed with EtOAc. The aqueous phase was basified with 1 N NaOH and extracted with EtOAc. The organic phase was dried over $Na_2SO_4$ and evaporated to dryness to yield a crude material which was purified by flash column chromatography on 230–400 mesh silica gel, utilising a mixture of EtOAc/hexane 3:7 as eluent. After evaporation of the solvent, 3.0 g of the title compound as a yellow solid were obtained.

$C_{24}H_{28}N_4O_4S$ MW=468.58 IR: (KBr) 2938, 1736, 1574, 1552, 1452, 1244, 1156, 942 748 $cm^{-1}$.

DESCRIPTION 25: 2-Phenyl-3-(4-sulfamoyl-piperazin-1-ylmethyl)-quinoline-4-carboxylic acid 3.0 g (6.04 mmol) of 3-(4-tert-butylsulfamoyl-piperazin-1-ylmethyl)-2-phenyl-quinoline-4-carboxylic acid methyl ester (compound of Description 23) were suspended in 50 ml of 6N HCl and the mixture was refluxed for 4 h. The solvent was evaporated in vacuo to dryness. For three times the residue was treated with $Et_2O$ and the solvent was evaporated to dryness to yield 3.0 of crude title compound used without further purification $C_{21}H_{22}N_4O_4S$ MW=426.44 IR: (KBr) 3281,2974, 1734, 1556, 1221, 1146, 1056,941, 765 $cm^{-1}$.

DESCRIPTION 26: 3-(4-Dimethylsulfamoyl-piperazin-1-ylmethyl)-2-phenyl-quinoline-4-carboxylic acid 3.0 g (6.40 mmol) of 3-(4dimethylsulfamoyl-piperazin-1-ylmethyl)-2-phenyl-quinoline-4-carboxylic acid methyl ester (compound of Description 24) were suspended in 50 ml of 6N HCl and the mixture was refluxed for 4 h. The solvent was evaporated in vacuo to dryness. After trituration of the residue with $Me_2CO$, 1.4 g of the title compound were recovered as a pale yellow solid used without further purification.

$C_{23}H_{26}N_4O_4S$ MW=454.55 R: (KBr) 3427, 2658, 1726, 1632, 1581, 1452, 1344, 1151, 932 745 $cm^{-1}$.

DESCRIPTION 27: 7-Methoxy-3-methyl-2-phenyl-quinoline-4-carboxylic acid methyl ester 16 g (54.5 mmol) of 7-methoxy-3-methyl-2-phenyl-quinoline-4-carboxylic acid (prepared analogously to starting material of Description A) were suspended in 400 ml of dry $CH_2Cl_2$ and 9.52 ml (126.93 mmol) of oxalyl chloride were added dropwise. Two drops of N,N-dimethylformamide (DMF) were added and the reaction mixture was stirred for 3 h at room temperature. The solvent was evaporated in vacuo to dryness, the residue was taken up with 150 ml of $CH_2Cl_2$ and quickly dropped in a solution of 200 ml of MeOH and 200 ml of $CH_2Cl_2$. After stirring for 1 h, the solvent was evaporated in vacuo to dryness, the residue was taken up with EtOAc and washed with 1% $NaHCO_3$; the organic layer was dried over $Na_2SO_4$, filtered and evaporated in vacuo to dryness. After trituration of the residue with $Et_2O$, 19 g of the title compound were recovered as a dark powder used without further purification.

$C_{19}H_{17}NO_3$ MW=307.35 IR (KBr) 3067,2947, 1918, 1729,1634, 1581, 1246, 846 $cm^{-1}$.

DESCRIPTION 28: 3-[1,4']Bipiperidinyl-1'-ylmethyl-8-bromo-7-methoxy-2-phenyl-quinoline-4-carboxylic acid methyl ester Prepared as described in Description B and Description 1 from 4.7 g (15.3 mmol) of 7-methoxy-3-methyl-2-phenyl-quinoline-4-carboxylic acid methyl ester (compound of Description 27), 5.5 g (30.6 mmol) of N-bromosuccinimide, 0.5 g (2.05 mmol) of dibenzoylperoxide, 3.85 g (23 mmol) of 4-piperidinopiperidine and 3.18 g ( 23.0 mmol) of $K_2CO_3$, by stirring in $CH_3CN$ at room temperature for 4 h. 6.2 g of the title compound were obtained.

$C_{29}H_{34}BrN_3O_3$ MW=552.51 IR (KBr) 3370,2938, 1712, 1612, 1352, 1268, 1174,704$cm^{-1}$.

DESCRIPTION 29: 3-[1,4']Bipiperidinyl-1'-ylmethyl-8-bromo-7-methoxy-2-phenyl-quinoline-4-carboxylic acid hydrochloride Prepared as described in Description 4 from 6.0 g (10.9 mmol) of 3-[1,4']bipiperidinyl-1'-ylmethyl-8-bromo-7-methoxy-2-phenylquinoline-4-carboxylic acid methyl ester (compound of Description 28) and 50 ml of 6 N HCl yielding 4.7 g of a slightly brown powder.

$C_{28}H_{32}BrN_3O_3$·HCl MW=574.94 IR: (KBr) 3453,2939, 2532, 1714, 1607, 1598, 1271, 1072,960, 779, 705, $cm^{-1}$.

DESCRIPTION 30: 3-[1,4']Bipiperidinyl-1'-ylmethyl-8-chloro-7-methoxy-2-phenyl-quinoline-4-carboxylic acid methyl ester Prepared as described in Description B and Description 1 from 9.0 g (29.3 mmol) of 7-methoxy-3-methyl-2-phenyl-quinoline-4-carboxylic acid methyl ester hydrochloride (compound of Description 27 HCl), 10.4 g (58.6 mmol) of N-bromosuccinimide, 1.0 g (4.10 mmol) of dibenzoylperoxide 9.9 g (58.6 mmol) of 4-piperidinopiperidine and 3.18 g ( 23.0 mmol) of $K_2CO_3$. Purified by flash column chromatography on 230–400 mesh silica gel, utilising a mixture of EtOAc/MeOH 9:1 containing 0.1% $NH_4OH$ (28%) affording 1.7 g of the title compound.

$C_{29}H_{34}ClN_3O_3$ MW=508.06 IR (KBr) 2934, 1730, 1610, 1501, 1238, 1079, 774, 706 $cm^{-1}$.

DESCRIPTION 31: 3-[1,4']Bipiperidinyl-1'-ylmethyl-8-chloro-7-hydroxy-2-phenyl-quinoline-4-carboxylic acid dihydrobromide 1.5 g (3.0 mmol) of 3-[1,4']bipiperidinyl-1'-ylmethyl-8-chloro-7-methoxy-2-phenyl-quinoline-4-carboxylic acid methyl ester (compound of Description 30) were dissolved in 50 ml of 48% HBr and the solution was refluxed for 8 h. The solvent was evaporated in vacuo to dryness yielding 2.2 g of the crude title compound as a dark powder used without further purification.

$C_{27}H_{31}ClN_3O_3$·2HBr MW=736.76 IR: (KBr) 2948, 1725, 1624, 1226, 959, 705 $cm^{-1}$.

The following Examples illustrate the invention; Table 1 summarizes all the compounds of the Examples 1–95 and their analytical data; Table 2 describes NMR spectroscopic data of Examples 1–95 and Table 3 illustrates chemical names of compounds of Examples 1–95.

EXAMPLE 2

2-Phenyl-3-(4-phenyl-piperidin-1-ylmethyl)-quinoline-4-carboxylic acid ((S)-1-phenyl-propyl)-amide 2.5 g (5.0 mmol) of crude 2-phenyl-3-(4-phenyl-piperidin-1-ylmethyl)-quinoline-4-carboxylic acid hydrochloride (compound of Description 4) were dissolved in 50 ml of dry THF; 1.1 ml (7.8 mmol) of triethylamine (TEA) and 2.4 g (6.5 mmol) of O-benzotriazol-1-yl-N,N,N',N'-tetramethyluroniumhexafluoro-phosphate (HBTU) were added and the reaction mixture was cooled at 0° C. 0.72 ml (5 mmol) of (S)-1-phenyl-propylamine, dissolved in 20 ml of dry $CH_2Cl_2$, were added dropwise and the reaction mixture was stirred at room temperature for 24 h and at 50° C. for 2 h. The solvent was evaporated in vacuo to dryness and the residue was taken up with EtOAc and washed with H$_2$O, 1 N NaOH and brine, dried over Na$_2$SO$_4$ and evaporated to dryness to yield a crude material which was purified by gradient flash column chromatography on 230–400 mesh silica gel, utilising a mixture of EtOAc/hexane 3:7 as starting eluent, and a mixture of EtOAc/hexane 4:6 as final eluent. After trituration with iPr$_2$O, 1.0 g of the title compound were recovered as a pale yellow solid used without further purification.

C$_{37}$H$_{37}$N$_3$O MW=539.72 IR: (KBr) 3279, 3060, 3028, 2931, 1633, 1536, 1494, 757, 699 cm$^{-1}$.

EXAMPLE 4

3-(4-Isopropyl-piperazin-1-ylmethyl)-2-phenyl-quinoline-4-carboxylic acid ((S)-1-cyclohexyl-ethyl)-amide dihydrochloride 2.3 g (5.0 mmol) of crude 3-(4-isopropyl-piperazin-1-ylmethyl)-2-phenyl-quinoline-4-carboxylic acid dihydrochloride (compound of Description 6) were dissolved in 200 ml of a 1:1 mixture of CH$_2$Cl$_2$/CH$_3$CN; 2.0 ml (15 mmol) of triethylamine (TEA) and 2.5 g (6.5 mmol) of O-benzotriazol-1-yl-N,N,N',N'-tetramethyluroniumhexafluorophosphate (HBTU) were added and the reaction mixture was cooled at 0° C. 0.74 ml (5 mmol) of (S)-1-cyclohexyl-ethylamine, dissolved in 10 ml of dry CH$_2$Cl$_2$, were added dropwise and the reaction mixture was stirred at room temperature for 24 h. The solvent was evaporated in vacuo to dryness and the residue was taken up with EtOAc and washed with H$_2$O, 1 N NaOH and brine, dried over Na$_2$SO$_4$ and evaporated to dryness to yield a crude material which was purified by flash column chromatography on 230–400 mesh silica gel, utilising a mixture of CH$_2$Cl$_2$/MeOH 95:5 containing 0.5% NH$_4$OH (28%). The residue was dissolved in acetone and acidified with HCl/Et$_2$O; the precipitate so formed was recovered by suction filtration to yield 0.9 g of the title compound as a yellow solid.

C$_{32}$H$_{42}$N$_4$O.2HCl MW=571.64 IR: (KBr) 341 1; 2927; 2851; 2667; 1650; 1546 cm$^{-1}$.

EXAMPLE 13

3-[1,4']Bipiperidinyl-1'-ylmethyl-2-phenyl-quinoline-4-carboxylic acid ((S)-1-cyclohexyl-ethyl)-amide dihydrochloride 4.0 g (8.0 mmol) of crude 3-[1,4']bipiperidinyl-1'-ylmethyl-2-phenyl-quinoline-4-carboxylic acid dihydrochloride (compound of Description 2) were dissolved in 300 ml of a 1:1 mixture of CH$_2$Cl$_2$/CH$_3$CN; 3.4 ml (24.6 mmol) of triethylamine (TEA) and 4.0 g (10.7 mmol) of O-benzotriazol-1-yl-N,N,N',N'-tetramethyluroniumhexafluorophosphate (HBTU) were added and the reaction mixture was cooled at 0° C. 1.22 ml (8.2 mmol) of (S) 1-cyclohexylethylamine, dissolved in 10 ml of dry CH$_2$Cl$_2$, were added dropwise and the reaction mixture was stirred at room temperature for 24 h. Additional 2.0 g (5.3 mmol) of HBTU and 2.0 ml (13.4 mmol) of (S)-1-cyclohexyl-ethylamine were added and the reaction mixture was heated to 40° C. for 8 h. The solvent was evaporated in vacuo to dryness and the residue was taken up with EtOAc and washed with H$_2$O, 1 N NaOH and brine, dried over Na$_2$SO$_4$ and evaporated to dryness to yield a crude material which was purified by flash column cromatography on 230–400 mesh silica gel, utilising a mixture of EtOAc/MeOH 95:5 containing 0.5% NH$_4$OH (28%). The residue was dissolved in acetone and acidified with HCl/Et$_2$O; the precipitate so formed was recovered by suction filtration to yield 3.2 g of title compound as a pale yellow solid.

C$_{35}$H$_{46}$N$_4$O.2HCl MW=611.70 IR: (KBr) 3422, 2928, 2852, 2659, 1647, 1546 cm$^{-1}$.

EXAMPLE 34

2-Phenyl-3-piperazin-1-ylmethyl-quinoline-4carboxylic acid ((S)-1-cyclohexyl-ethyl)-amide Synthesised starting from the compound of Description 11 and following the procedure of Description 13.

C$_{29}$H$_{36}$N$_4$O MW=456.63

EXAMPLE 47

3-[4-3-Diethylamino-propanoyl)-piperazin-1-ylmethyl]-2-phenyl-quinoline-4-carboxylic acid ((S)-1-cyclohexyl-ethyl)-amide 0.4 g (0.88 mmol) of 2-phenyl-3-piperazin-1-ylmethyl-quinoline-4-carboxylic acid ((S)-1-cyclohexyl-ethyl)-amide (compound of Example 34), 0.5 g (1.3 mmol) of HBTU, 360 microliters (2.5 mmol) of triethyl amine and 240 mg of 3-diethylaminopropionic acid were dissolved in 10 ml of anhydrous THF and were stirred 16 hours at room temperature. The solvent was concentrated to dryness and the residue was dissolved in 20 ml of EtOAc and washed with water then with 0.5 N aqueous NaOH and again with water. The organic phase was dried over MgSO$_4$, concentrated to dryness. The residue was purified by flash chromatography on silicagel (CH$_2$Cl$_2$/MeOH: 90/10). The fractions containing the desired compound were concentrated and the residue was crystallised from di-isopropyl ether affording 250 mg (yield 48.7%) of the title compound as white crystals.

C$_{36}$H$_{49}$N$_5$O$_2$ MW=583.82

EXAMPLE 53

({4-[4-((S)-1-Cyclohexyl-ethylcarbamoyl)-2-phenyl-quinolin-3-ylmethyl]-piperazin-1-yl}-dimethylamino-methylene)-dimethyl-ammonium hexafluorophosphate 50 mg (0.11 mmol) of the piperazine of Example 34 were reacted with 62 mg (0.16 mmol) of HBTU and 18 mg (0.17 mmol) of triethylamine in a mixture of 1.2 ml of anhydrous THF and 1 ml of CH$_2$Cl$_2$. This mixture was stirred 48 h at room temperature, then concentrated to dryness. The residue was dissolved in 1 ml of water and 1 ml of ethyl acetate. The aqueous phase was extracted twice with EtOAc, washed twice with water, dried over MgSO$_4$, concentrated to dryness. The residue was purified by flash chromatography on silicagel (CH$_2$Cl$_2$/MeOH: 95/5) to afford 43 mg of the title compound as a white solid (yield 55.8%).

C$_{34}$H$_{47}$N$_6$O.PF$_6$ MW=700.75

EXAMPLE 55

3-(4-Amino-piperidin-1-ylmethyl)-2-phenyl-quinoline-4-carboxylic acid ((S)-1-phenyl-propyl)-amide 0.477 g (1 mmol) of 3-(4-oxo-piperidin-1-ylmethyl)-2-phenyl-quinoline-4-carboxylic acid ((S)-1-phenyl-propyl)-amide (compound of Description 18), 0.462 g (6 mmol) of ammonium acetate were dissolved in 10 ml of methanol and stirred at room temperature for 1 h. Then 0.08 g of sodium cyanoborohydride were added and the mixture was stirred one night at room temperature. The reaction mixture was poured in 50 ml of water and the formed precipitate was filtered off. The aqueous phase was extracted with methylene chloride. The collected solid was dissolved in methylene chloride, both organic phases merged, washed with water, dried over $MgSO_4$, concentrated to dryness. The residue was purified by micro flash chromatography on silicagel ($CH_2Cl_2$/MeOH/$NH_4OH$: 90/10/1) to afford 47 mg of the title compound as a white solid (yield ca 10%).

$C_{31}H_{34}N_4O$ MW=478.64

EXAMPLE 66

3-[1,4']Bipiperidinyl-1'-ylmethyl-8-bromo-7-methoxy-2-phenyl-quinoline-4-carboxylic acid ((S)-1-phenyl-propyl)-amide Prepared as described in Example 2 from 2 g (3.7 mmol) of 3-[1,4']bipiperidinyl-1'-ylmethyl-8-bromo-7-methoxy-2-phenyl-quinoline-4-carboxylic acid (compound of Description 29), 1.55 ml (11.1 mmol) of triethylamine (TEA) 1.82 g (4.8 mmol) of O-benzotriazol-1-yl-N,N,N',N'-tetramethyluroniumhexa-fluorophosphate (HBTU) and 0.75 g (5.5 mmol) of (S)-1-phenyl-propylamine The crude material was purified by flash column chromatography on 230–400 mesh silica gel, utilising a mixture of EtOAc/MeOH 95:5 containing 0.05% $NH_4OH$ (28%) affording 0.4 g of title compound. After trituration with $iPr_2O$, 0.3 g of the title compound were recovered as a pale yellow solid.

$C_{37}H_{43}BrN_4O_2$ MW=655,68 IR: (KBr) 3278, 2936, 1641, 1276, 1073, 845, 702cm$^{-1}$.

EXAMPLE 67

3-[1,4']Bipiperidinyl-1'-ylmethyl-7-methoxy-2-phenyl-quinoline-4-carboxylic acid ((S)-1-phenyl-propyl)-amide hydrochloride 0.2 g (0.31 mmol) of 3-[1,4']Bipiperidinyl-1'-ylmethyl-8-bromo-7-methoxy-2-phenyl-quinoline-4-carboxylic acid ((S)-1-phenyl-propyl)-amide (compound of Example 66) and 0.43 ml (0.31 mmol) of TEA were dissolved in 100 ml of EtOH. 20 mg of 10% Palladium on charcoal were added under nitrogen atmosphere and the mixture was hydrogenated at 1 psi for 3 h. The catalyst was filtered off, the solvent was evaporated in vacuo to dryness and the residue was purified by gradient flash column chromatography on 230–400 mesh silica gel, utilising EtOAc containing 0.05% $NH_4OH$ (28%) as starting eluent, and a mixture of EtOAc/MeOH 95:5 containing 0.05% $NH_4OH$ (28%) as final eluent. The residue was dissolved in acetone and acidified with HCl/$Et_2O$; the precipitate so formed was recovered by suction filtration to yield 0.1 g of the title compound as a pale yellow solid.

$C_{37}H_{44}N_4O_2$ MW=576.78 IR: (KBr) 3239, 2943, 2530, 1619, 1534, 1222, 1027, 844, 703 cm$^{-1}$.

EXAMPLE 72

3-[4-(3,4-Dioxo-2-pyrrolidin-1-yl-cyclobut-1-enyl)-piperazin-1-ylmethyl]-2-phenyl-quinoline-4-carboxylic acid ((S)-1-cyclohexyl-ethyl)-amide 0.25 g (0.55 mmol) of 2-phenyl-3-piperazin-1-ylmethyl-quinoline-4-carboxylic acid ((S)-1-cyclohexyl-ethyl)-amide (compound of Example 34) and 0.124 g (0.55 mmol) of 3,4-di-N-butoxy-3-cyclobuten-1,2-dione (Aldrich) were stirred in 3 ml of ethanol at room temperature for 7 h. Then, 0.15 g (2.2 mmol) of pyrrolidine was added and stirring was continued for one night. The mixture was concentrated in vacuo and the residue was purified by flash chromatography on silicagel ($CH_2Cl_2$/MeOH: 98/2). After concentration of the desired fractions, the residue was crystallised from di-isopropyl ether. The solid obtained was purified again by chromatography on silicagel (EtOAc as eluent). After concentration of the desired fractions the residue was re-crystallised from di-isopropyl ether to afford 0.180 g (yield 54%) of the title compound as white crystals.

$C_{37}H_{43}N_5O_3$ MW=605.78

EXAMPLE 75

3-(4-Methylthiocarbamoyl-piperazin-1-ylmethyl)-2-phenyl-quinoline-4-carboxylic acid ((S)-1-cyclohexyl-ethyl)-amide 0.4 g (0.87 mmol) of 2-phenyl-3-piperazin-1-ylmethyl-quinoline-4carboxylic acid ((S)-1-cyclohexyl-ethyl)-amide (compound of Example 34) were dissolved in 10 ml of methylene chloride and 0.09 g methylisothiocyanate were added. The mixture was stirred for 5 h at room temperature and the solvent was concentrated in vacuo and the residue was purified by flash chromatography on silicagel (EtOAc/heptane: 95/5) to afford 0.43 g (yield 92%) of the title compound as white crystals.

$C_{31}H_{39}N_5OS$ MW=529.75

EXAMPLE 76

3-[4-(1-Cyanoimino-1-pyrrolidin-1-yl-methyl)-piperazin-1-ylmethyl]-2-phenyl-quinoline-4-carboxylic acid ((S)-1-cyclohexyl-ethyl)-amide 0.25 g (0.45 mmol) of 3-[4-1-cyanoimino-1-methylsulfanyl-methyl)-piperazin-1-ylmethyl]-2-phenyl-quinoline-4-carboxylic acid ((S)-1-cyclohexyl-ethyl)-amide (compound of Description 15) and 1.5 ml of pyrrolidine were heated to reflux for 2 h. The excess of pyrrolidine was removed in vacuo and the residue was purified by flash chromatography on silicagel (EtOAc/$CH_2Cl_2$: 80/20). After concentration of the desired fractions the residue was crystallised from di-isopropyl ether to afford 0.195 g (yield 75%) of the title compound as white crystals.

$C_{35}H_{43}N_7O$ MW=577.77

EXAMPLE 78

3-[4-(1-Methylimino-1-pyrrolidin-1-yl-methyl)-piperazin-1-ylmethyl]-2-phenyl-quinoline-4-carboxylic acid ((S)-1-cyclohexyl-ethyl)-amide 0.2 g (ca 0.3 mmol) of the crude salt of Description 17 was dissolved in 10 ml of acetonitrile and 1 g of pyrrolidine and 1.5 g of KF were added. The mixture was refluxed for one night. After prolonged concentration under vacuum, the residue was dissolved in methylene chloride and the solid filtered off and discarded. The solution was concentrated and the residue purified by flash chromatography on silicagel (EtOAc/MeOH/$NH_4OH$: 90/10/1). After concentration of the desired fractions, the residue was crystallised from diethyl ether to afford 0.120 g (yield 71%) of the title compound as a white amorphous solid.

$C_{35}H_{46}N_6O$ MW=566.79

EXAMPLE 82

3-(4-Carbamimidoyl-piperazin-1-ylmethyl)-2-phenyl-quinoline-4-carboxylic acid ((S)-1-cyclohexyl-ethyl)-amide sesqui-p-toluenesulphonate 0.3 g (0.66 mmol) of 2-phenyl-3-piperazin-1-ylmethyl-quinoline-4-carboxylic acid ((S)-1-cyclohexyl-ethyl)amide (compound of Example 34), 0.313 g (0.94 mmol) of benzotriazole-1-carboxamidinium p-toluenesulphonate (reagent described in Synthetic Communications, 1995, 25 (8), 1173–1186), 0.167 ml (0.94 mmol) of diisopropylethylamine were stirred for 3 days. Addition of diethyl ether led to the formation of a precipitate which was further triturated with ethyl ether. The white solid was purified by two successive flash chromatographies on silicagel, eluting first with $CH_2Cl_2$/MeOH: 90/10, then with $CH_2Cl_2$/MeOH/ $NH_4OH$: 90/10/1. Concentration of the desired fractions gave a solid which was triturated with diethyl ether to afford 0.225 g of the title compound as a salt of p-toluenesulfonic acid. Analysis of the NMR spectra suggested the occurrence of 1.6 equivalent of acid for one molecule of parent compound (in Table 2, the NMR refers to the parent compound).

$C_{30}H_{38}N_6O.1.5C_7H_8O_3S$ MW=757.00

EXAMPLE 84

3-[4-(1-Methanesulfonylimino-1-pyrrolidin-1-yl-methyl)-piperazin-1-ylmethyl]-2-phenyl-quinoline-4-carboxylic acid ((S)-1-cyclohexyl-ethyl)-amide 0.46 g (0.76 mmol) of crude 3-[4-(1-methanesulfonylimino-1-methylsulfanyl-methyl)-piperazin-1-ylmethyl]-2-phenyl-quinoline-4-carboxylic acid ((S)-1-cyclohexyl-ethyl)-amide (compound of Description 16) and 5 ml of pyrrolidine were heated to reflux for 5 h. The excess of pyrrolidine was removed in vacuo and the residue was purified by flash chromatography on silicagel ($CH_2Cl_2$/ MeOH: 97/3). After concentration of the desired fractions, the residue was crystallised in di-isopropyl ether to afford 0.310 g (yield 65%) of the title compound as white crystals.

$C_{35}H_{46}N_6O_3S$ MW=630.85

EXAMPLE 85

4-(4-{4-[4-((S)-2-Methyl-1-phenyl-propylcarbamoyl)-2-phenyl-quinolin-3-ylmethyl]-piperazin-1-yl}-4-oxo-butyric acid 200 mg (0.42 mmol) of 2-phenyl-3-piperazin-1-ylmethylquinoline-4-carboxylic acid ((S)-1-phenyl-propyl)-amide (compound of Description 13) were dissolved in 5 ml acetone and 42 mg of succinic anhydride were added. The mixture was then refluxed for 10 hours. After cooling the mixture was diluted with 50 ml of $CH_2Cl_2$, washed three times with 30 ml water, dried over $MgSO_4$, concentrated to dryness. The residue was purified by flash chromatography on silicagel ($CH_2Cl_2$/MeOH: 90/10) to afford 130 mg of the title compound as white crystals (yield 54%).

$C_{35}H_{38}N_4O_4$ MW=578.71

EXAMPLE 90

2-Phenyl-3-(4-sulfamoyl-piperazin-1-ylmethyl)-quinoline-4-carboxylic acid ((S)-1-phenyl-propyl)-amide 3.0 g (5.78 mmol) of crude 2-phenyl-3-(4-sulfamoyl-piperazin-1-ylmethyl)-quinoline-4-carboxylic acid (compound of Description 25) were dissolved in 150 ml of 1:1 mixture of $CH_2Cl_2$ and dry THF; 2.41 ml (17.34 mmol) of triethylamnine (TEA) and 4.38 g (11.56 mmol) of O-benzotriazol-1-yl-N,N,N',N'-tetramethyl-uroniumhexafluorophosphate (HBTU) were added and the reaction mixture was cooled at 0° C. 1.56 g (11.56 mmol) of (S)-1-phenyl-propylamine, dissolved in 20 ml of dry $CH_2Cl_2$, were added dropwise and the reaction mixture was stirred at room temperature for 24 h and at 50° C. for 4 h. The solvent was evaporated in vacuo to dryness and the residue was taken up with EtOAc, washed with $H_2O$ and 1 N NaOH, dried over $Na_2SO_4$ and evaporated to dryness. The crude material was purified by flash column chromatography on 230–400 mesh silica gel, utilising a mixture of EtOAc/ hexane 8:2. After trituration with $iPr_2O$, 1.05 g of the title compound were recovered as a pale yellow solid.

$C_{30}H_{33}N_5O_3S$ MW=543.69 IR: (KBr) 3270, 3060, 2967, 1959, 1644, 1537, 1492, 1455, 1354, 1163, 949, 764, 702 $cm^{-1}$.

EXAMPLE 91

3-(4Dimethylsulfamoyl-piperazin-1-ylmethyl)-2-phenyl-quinoline 4-carboxylic acid ((S)-1-phenyl-propyl)-amide 1.4 g (2.85 mmol) of crude 3-(4-Dimethylsulfamoyl-piperazin-1-ylmethyl)-2-phenyl-quinoline-4-carboxylic acid (compound of Description 26) were dissolved in 100 ml of 1:1 mixture of $CH_2Cl_2$ and dry THF; 1.19 ml (8.55 mmol) of triethylamine (TEA) and 2.16 g (5.70 mmol) of O-benzotriazol-1-yl-N,N,N',N'-tetramethyluroniumhexafluorophosphate (HBTU) were added and the reaction mixture was cooled at 0° C. 0.77 g (5.70 mmol) of (S)-1-phenyl-propylamine, dissolved in 15 ml of dry $CH_2Cl_2$, were added dropwise and the reaction mixture was stirred at room temperature for 24 h and at 50° C. for 4 h. The solvent was evaporated in vacuo to dryness and the residue was taken up with EtOAc and washed with $H_2O$ and 1 N NaOH, dried over $Na_2SO_4$ and evaporated to dryness to yield a crude material which was purified by flash column chromatography on 230–400 mesh silica gel, utilising a mixture of EtOAc/hexane 8:2. After trituration with $iPr_2O$, 0.3 g of title compound were recovered as a white powder.

$C_{32}H_{37}N_5O_3S$ MW=571.74 IR: (KBr) 3315, 3059, 2965, 2813, 1955, 1661, 1638, 1533, 1491, 1455, 1349, 1152, 947, 748, 702 $cm^{-1}$.

TABLE I

[Structure: quinoline-4-carboxamide with R-NH-C(O)- at 4-position, R2 at 3-position, R3 at 2-position, R1 at 6/7-position; R3 = Ph]

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 1 | (S)-1-phenylpropyl | H | 4-cyclohexylpiperazin-1-yl, N-ethyl | C₃₆H₄₂N₄O.2HCl | 619.76 | 261–263 | −49.0 (c = 0.48) |
| 2 | (S)-1-phenylpropyl | H | 4-phenylpiperidin-1-yl, N-ethyl | C₃₇H₃₇N₃O | 539.73 | 90–95 | −47.1 |
| 3 | (S)-1-cyclohexylpropyl | H | 4-benzylpiperazin-1-yl, N-ethyl | C₃₆H₄₂N₄O.2HCl | 619.68 | 176–179 | +16.7 (c = 0.6) |
| 4 | (S)-1-cyclohexylpropyl | H | 4-isopropylpiperazin-1-yl, N-ethyl | C₃₂H₄₂N₄O.2HCl | 571.64 | 180–183 | +19.5 (c = 0.57) |

TABLE I-continued

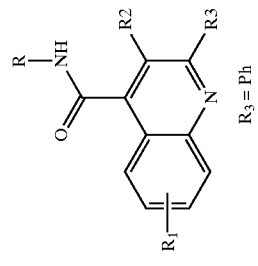

R3 = Ph

| Ex. | R | R1 | R2 | Molecular Formula | Molecular Weight | Melting Point (° C.) | $[\alpha]_D^{20}$ (c = 0.5, MeOH) |
|---|---|---|---|---|---|---|---|
| 5 | (S)-cyclohexyl-ethyl | H | 1-(2-phenylethyl)-4-ethylpiperazine | $C_{37}H_{44}N_4O \cdot 2HCl$ | 633.71 | 168–171 | +16.1 (c = 0.57) |
| 6 | (S)-phenyl-ethyl | H | 1-isopentyl-4-ethylpiperazine | $C_{35}H_{42}N_4O$ | 534.75 | amorphous solid | −46.5 |
| 7 | (S)-phenyl-ethyl | H | 1-neohexyl-4-ethylpiperazine | $C_{36}H_{44}N_4O$ | 548.78 | amorphous solid | −42.5 |
| 8 | (S)-phenyl-ethyl | H | 1-isobutyl-4-ethylpiperazine | $C_{34}H_{40}N_4O$ | 520.72 | amorphous solid | −45.7 |

TABLE I-continued

![Structure: quinoline with R1 on benzene ring, R2 at position 3, R3=Ph at position 2, and C(=O)NH-R at position 4]

R3 = Ph

| Ex. | R | R1 | R2 | Molecular Formula | Molecular Weight | Melting Point (° C.) | [a]$_D^{20}$ (c = 0.5, MeOH) |
|---|---|---|---|---|---|---|---|
| 9 | (S)-1-phenylpropyl | H | 4-ethylpiperazin-1-yl-methyl-cyclohexyl | C$_{37}$H$_{44}$N$_4$O | 560.79 | amorphous solid | −38.9 |
| 10 | (S)-1-phenylpropyl | H | 4-ethylpiperazin-1-yl-methyl-(2-ethylbutyl) | C$_{36}$H$_{44}$N$_4$O | 548.78 | amorphous solid | −45.8 |
| 11 | (S)-1-phenylpropyl | H | 1-ethyl-4-phenyl-4-(N-methylacetamido)piperidine | C$_{40}$H$_{42}$N$_4$O$_2$ | 610.81 | 100 (dec) | — |

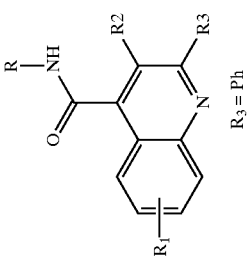

TABLE I-continued $R_3 = Ph$

| Ex. | R | $R_1$ | $R_2$ | Molecular Formula | Molecular Weight | Melting Point (° C.) | $[\alpha]_D^{20}$ (c = 0.5, MeOH) |
|---|---|---|---|---|---|---|---|
| 16 | (S)-1-phenylpropyl | H | 4-(2-methoxyethyl)piperazin-1-ylmethyl | $C_{33}H_{38}N_4O_2$ | 522.69 | 138–140 | — |
| 17 | (S)-1-cyclohexylpropyl | H | 4-(2-methoxyethyl)piperazin-1-ylmethyl | $C_{32}H_{42}N_4O_2$ | 514.71 | 113–115 | |
| 18 | (S)-1-phenylpropyl | H | 4-(4-hydroxypiperidin-1-yl)piperidin-1-ylmethyl | $C_{36}H_{42}N_4O_2$ | 562.75 | 166–168 | |
| 19 | (S)-1-phenylpropyl | H | 4-morpholinopiperidin-1-ylmethyl | $C_{35}H_{40}N_4O_2$ | 548.73 | 157–165 | |

TABLE I-continued

Structure: R-NH-C(=O)- attached to quinoline at 4-position, with R2 at 3-position, R3 at 2-position (R3 = Ph), and R1 on benzo ring.

| Ex. | R | R$_1$ | R$_2$ | Molecular Formula | Molecular Weight | Melting Point (° C.) | $[\alpha]_D^{20}$ (c = 0.5, MeOH) |
|---|---|---|---|---|---|---|---|
| 20 | (S)-1-cyclohexylpropyl | H | piperazinyl-CH$_2$CH$_2$-O-CH$_2$CH$_2$OH | C$_{33}$H$_{44}$N$_4$O$_3$ | 544.74 | 126–128 | |
| 21 | (S)-1-phenylpropyl | H | 4-(1-benzylpiperidin-4-yl)-N-methylamino-CH$_2$- | C$_{39}$H$_{42}$N$_4$O | 582.79 | amorphous solid | |
| 22 | (S)-1-cyclohexylpropyl | H | 4-(1-benzylpiperidin-4-yl)-N-methylamino-CH$_2$- | C$_{38}$H$_{46}$N$_4$O | 574.81 | amorphous solid | |
| 23 | (S)-1-phenylpropyl | H | 4-acetylpiperazin-1-yl-CH$_2$- | C$_{32}$H$_{34}$N$_4$O$_2$ | 506.65 | 117–119 | |

TABLE I-continued

[Structure: quinoline with R-NH-C(O)- at 4-position, R2 at 3-position, R3 at 2-position (R3 = Ph), R1 on benzo ring]

| Ex. | R | R1 | R2 | Molecular Formula | Molecular Weight | Melting Point (° C.) | $[\alpha]_D^{20}$ (c = 0.5, MeOH) |
|---|---|---|---|---|---|---|---|
| 24 | (S)-cyclohexyl(methyl) | H | 4-benzoylpiperazin-1-ylmethyl (gem-dimethyl linker) | $C_{35}H_{40}N_4O_2$ | 560.74 | 150–152 | |
| 25 | (S)-cyclohexyl(methyl) | H | 4-isobutyrylpiperazin-1-ylmethyl | $C_{33}H_{42}N_4O_2$ | 526.72 | 149–151 | |
| 26 | (S)-cyclohexyl(methyl) | H | 4-(pyrimidin-2-yl)piperazin-1-ylmethyl | $C_{33}H_{38}N_6O_5$ | 534.70 | 197–199 | |
| 27 | (S)-phenyl(ethyl) | H | 4-(pyrimidin-2-yl)piperazin-1-ylmethyl | $C_{34}H_{34}N_6O_5$ | 542.68 | 157–159 | |

TABLE I-continued

Structure: quinoline core with R-NH-C(=O)- at position 4, R2 at position 3, R3 at position 2 (R3 = Ph), and R1 on the benzene ring.

| Ex. | R | R1 | R2 | Molecular Formula | Molecular Weight | Melting Point (° C.) | $[\alpha]_D^{20}$ (c = 0.5, MeOH) |
|---|---|---|---|---|---|---|---|
| 28 | (S)-1-phenylpropyl | H | 4-(2-hydroxyethyl)piperazin-1-ylmethyl | $C_{32}H_{36}N_4O_2$ | 508.66 | 142–144 | |
| 29 | (S)-1-cyclohexylpropyl | H | 4-(2-hydroxyethyl)piperazin-1-ylmethyl | $C_{31}H_{40}N_4O_2$ | 500.68 | 95–105 | |
| 30 | (S)-1-phenylpropyl | H | 4-piperidin-1-ylpiperidin-1-ylmethyl | $C_{35}H_{40}N_4O \cdot 2HCl$ | 605.66 | 208–210 | |
| 31 | (S)-1-phenylpropyl | H | 4-benzoylpiperazin-1-ylmethyl | $C_{37}H_{36}N_4O_2$ | 623.47 | 180–182 | −1.37 (c = 0.55) |

TABLE I-continued

| Ex. | R | R₁ | R₂ | Molecular Formula | Molecular Weight | Melting Point (° C.) | [a]ᴅ²⁰ (c = 0.5, MeOH) |
|---|---|---|---|---|---|---|---|
| 32 | (S)-1-phenylpropyl | H | 4-(4-methylpiperazin-1-yl)piperidin-1-ylmethyl | C₃₆H₄₃N₅O | 561.77 | amorphous solid | |
| 33 | (S)-1-cyclohexylethyl | H | 4-(4-methylpiperazin-1-yl)piperidin-1-ylmethyl | C₃₅H₄₇N₅O | 553.79 | amorphous solid | |
| 34 | (S)-1-cyclohexylethyl | H | piperazin-1-ylmethyl | C₂₉H₃₆N₄O | 456.63 | amorphous solid | |

TABLE I-continued

R₃ = Ph

| Ex. | R | R₁ | R₂ | Molecular Formula | Molecular Weight | Melting Point (° C.) | [α]_D^{20} (c = 0.5, MeOH) |
|---|---|---|---|---|---|---|---|
| 35 | (S)-CH(Et)(Ph) | H | -CH₂C(CH₃)₂-N(CH₂CH₂NEt₂)₂ | $C_{38}H_{51}N_5O$ | 593.85 | amorphous solid | |
| 36 | (S)-CH(cyclohexyl) | H | -CH₂C(CH₃)₂-(1-piperidinyl-4-C(O)NH₂) | $C_{31}H_{38}N_4O_2$ | 498.67 | 219–221 | |
| 37 | (S)-CH(cyclohexyl) | H | -CH₂CH₂-(4-ethylpiperazin-1-yl) | $C_{31}H_{40}N_4O·2HCl$ | 557.61 | 188–190 | +16.0 (c = 0.2) |

TABLE I-continued

| Ex. | R | R1 | R2 | R3 = Ph | Molecular Formula | Molecular Weight | Melting Point (° C.) | [α]D20 (c = 0.5, MeOH) |
|---|---|---|---|---|---|---|---|---|
| 38 | (S)-CH(Et)(Ph) | H | 1-(benzimidazol-2-one-3-yl)piperidin-4-ylmethyl | | C38H37N5O2 | 595.74 | 195–197 | |
| 39 | (S)-CH(Et)(cyclohexyl) | H | 1-(benzimidazol-2-one-3-yl)piperidin-4-ylmethyl | | C37H41N5O2 | 587.76 | 204–206 | |
| 40 | (S)-CH(Et)(Ph) | H | 1-methyl-4-(N-methylamino)piperidinylmethyl | | C33H38N4O | 506.69 | amorphous solid | |

TABLE I-continued

[Structure: quinoline-4-carboxamide core with R-NH-C(=O)- at position 4, R2 at position 3, R3 = Ph at position 2, R1 substituent on benzene ring]

R3 = Ph

| Ex. | R | R1 | R2 | Molecular Formula | Molecular Weight | Melting Point (° C.) | $[\alpha]_D^{20}$ (c = 0.5, MeOH) |
|---|---|---|---|---|---|---|---|
| 41 | (S)-cyclohexyl-CH- | H | -CH2-N(CH2CH2N(Et)2)2 | $C_{37}H_{55}N_5O$ | 585.87 | amorphous solid | |
| 42 | (S)-cyclohexyl-CH- | H | -CH2-(1-(4-morpholino)piperidinyl) | $C_{34}H_{44}N_4O_2$ | 540.75 | 135–137 | |
| 43 | (S)-cyclohexyl-CH- | H | -CH2-(1-(4-hydroxy)piperidinyl-piperidine) | $C_{35}H_{46}N_4O_2$ | 554.77 | 150–160 | |

TABLE I-continued

[Structure: R-NH-C(=O)- attached to position 4 of quinoline; R2 at position 3, R3 at position 2 (R3 = Ph), R1 at position 6/7]

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 44 | (S)-1-cyclohexylethyl | H | N,N-diethyl carboxamide-piperidin-3-yl (N-CH₂-) | $C_{35}H_{46}N_4O_2$ | 554.77 | amorphous solid | |
| 45 | (S)-1-phenylethyl | H | N,N-diethyl carboxamide-piperidin-3-yl (N-CH₂-) | $C_{36}H_{42}N_4O_2$ | 562.74 | amorphous solid | |
| 46 | (S)-1-cyclohexylethyl | H | 4-(N,N-dimethylaminoacetyl)piperazin-1-yl (N-CH₂-) | $C_{33}H_{43}N_5O_2$ | 541.74 | 173–175 | |
| 47 | (S)-1-cyclohexylethyl | H | 4-(3-(N,N-diethylamino)propanoyl)piperazin-1-yl (N-CH₂-) | $C_{36}H_{49}N_5O_2$ | 583.82 | 104–106 | |

TABLE I-continued
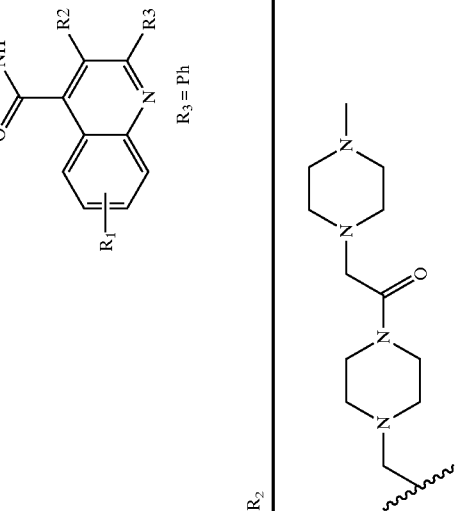
R3 = Ph
| Ex. | R | R1 | R2 | Molecular Formula | Molecular Weight | Melting Point (° C.) | $[\alpha]_D^{20}$ (c = 0.5, MeOH) |
|---|---|---|---|---|---|---|---|
| 48 | 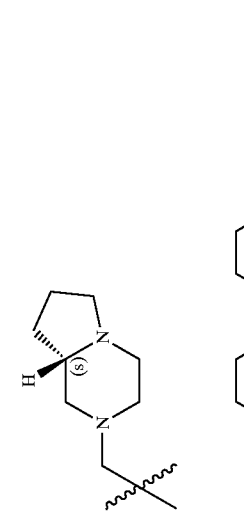 | H | 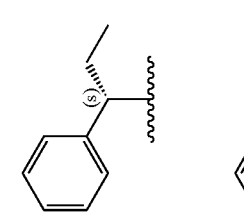 | $C_{36}H_{48}N_6O_2$ | 596.81 | 162–163 | |
| 49 | | H | | $C_{33}H_{36}N_4O \cdot 2HCl$ | 577.60 | 196–198 | −54.4 (c = 0.21) |
| 50 | | H | | $C_{36}H_{48}N_4O \cdot 2HCl$ | 625.73 | 203–205 | −5.2 (c = 0.35) |
| 51 | | H | 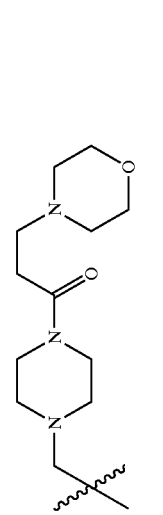 | $C_{36}H_{47}N_5O_3$ | 597.80 | amorphous solid | |

TABLE I-continued

[Structure: quinoline core with R-NH-C(=O)- at position 4, R2 at position 3, R3 at position 2 (R3 = Ph), R1 on benzene ring]

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 52 | (S)-cyclohexyl(methyl) | H | imidazolyl-CH₂-C(=O)-piperazinyl-CH₂-C(CH₃)- | C₃₄H₄₀N₆O₂ | 564.73 | 178–210 | |
| 53 | (S)-cyclohexyl(methyl) | H | (Me₂N)₂C⁺-piperazinyl-CH₂-C(CH₃)- | C₃₄H₄₇N₆O | 700.75 | amorphous solid | |
| 54 | (S)-cyclohexyl(methyl) | H | morpholinyl-CH₂-C(CH₃)- | C₂₉H₃₅N₃O₂ | 457.61 | 178–180 | |
| 55 | (S)-phenyl(ethyl) | H | 4-aminopiperidinyl-CH₂-C(CH₃)- | C₃₁H₃₄N₄O | 478.64 | 98–102 | |

TABLE I-continued

R3 = Ph

| Ex. | R | R1 | R2 | Molecular Formula | Molecular Weight | Melting Point (° C.) | $[a]_D^{20}$ (c = 0.5, MeOH) |
|---|---|---|---|---|---|---|---|
| 56 | (S)-1-phenylpropyl | H | 4-(pyridin-2-yl)piperazin-1-ylmethyl | $C_{35}H_{35}N_5O$ | 541.69 | 125–126 | |
| 57 | (S)-1-phenylpropyl | H | bis(2-methoxyethyl)aminomethyl | $C_{32}H_{37}N_3O_3$ | 511.66 | amorphous solid | |
| 58 | (S)-1-cyclohexylpropyl | H | bis(2-methoxyethyl)aminomethyl | $C_{31}H_{41}N_3O_3$ | 503.68 | 114–115 | |
| 59 | (S)-1-cyclohexylpropyl | H | 4-(pyridin-2-yl)piperazin-1-ylmethyl | $C_{34}H_{39}N_5O$ | 533.72 | 152–154 | |

TABLE I-continued

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 60 | (S)-1-phenylpropyl | H | cis-2,6-dimethylpiperazinyl | C₃₂H₃₆N₄O | 492.66 | 114-120 | |
| 61 | (S)-1-cyclohexylpropyl | H | 1,4-dioxa-8-azaspiro[4.5]decyl | C₃₂H₃₉N₃O₃ | 513.68 | 184-185 | |
| 62 | (S)-1-phenylpropyl | H | 4-(4-methylpiperazinyl)piperidinyl | C₃₆H₄₃N₅O | 561.77 | 85-100 | |
| 63 | (S)-1-phenylpropyl | H | 2-oxo-1,8-diazaspiro[4.5]decyl | C₃₄H₃₆N₄O₂ | 532.68 | 129-131 | |

TABLE I-continued

R₃ = Ph

| Ex. | R | R₁ | R₂ | Molecular Formula | Molecular Weight | Melting Point (° C.) | [α]_D^{20} (c = 0.5, MeOH) |
|---|---|---|---|---|---|---|---|
| 64 | (S)-CH(Et)(Ph) | H | spiro-hydantoin-piperidinyl-CH₂-C(Me)₂- | $C_{33}H_{33}N_5O_3$ | 547.66 | amorphous solid | |
| 65 | (S)-CH(Et)(Ph) | H | 4-(4-methylpiperazin-1-yl)piperidinyl-CH₂-C(Me)₂- | $C_{34}H_{39}N_5O$ | 533.71 | amorphous solid | |
| 66 | (S)-CH(Et)(Ph) | 7-OMe, 8-Br | 4-piperidin-1-yl-piperidinyl-CH₂-C(Me)₂- | $C_{37}H_{43}BrN_4O_2$ | 655.68 | 156–160 | −30.3 (c = 0.53) |
| 67 | (S)-CH(Et)(Ph) | 7-OMe | 4-piperidin-1-yl-piperidinyl-CH₂-C(Me)₂- | $C_{37}H_{44}N_4O_2$ | 576.78 | 208–210 | −0.31 (c = 0.2) |

TABLE I-continued

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 68 | (S)-1-phenylpropyl | H | 2-methyl-2,7-diazaspiro[4.4]nonane | C₃₄H₃₈N₄O | 518.70 | amorphous solid | |
| 69 | (S)-1-cyclohexylpropyl | H | 4-piperidinylpiperidine | C₃₄H₄₄N₄O | 524.75 | amorphous solid | |
| 70 | (S)-1-phenylpropyl | H | 4-(2-oxotetrahydropyrimidin-1-yl)piperidine | C₃₅H₃₉N₅O₂ | 561.73 | amorphous solid | |
| 71 | (S)-1-phenylpropyl | H | 1-oxa-4,9-diazaspiro[5.5]... | C₃₃H₃₄N₄O₃ | 534.66 | amorphous solid | |

TABLE I-continued

![structure: R-NH-C(=O)- attached to quinoline bearing R2, R3, R1; R3 = Ph]

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 72 | (S)-cyclohexyl-CH- | H | pyrrolidinyl-squarate-piperazinyl-CH₂-C(CH₃)- | $C_{37}H_{43}N_5O_3$ | 605.78 | 170–180 | |
| 73 | (S)-cyclohexyl-CH- | H | N-cyano-N'-methylguanidino-piperazinyl-CH₂-C(CH₃)- | $C_{32}H_{43}N_7O$ | 537.71 | 175–180 | |
| 74 | (S)-cyclohexyl-CH- | H | 4,5-dihydrothiazol-2-yl-piperazinyl-CH₂-C(CH₃)- | $C_{32}H_{39}N_5OS$ | 541.76 | 174–176 | |
| 75 | (S)-cyclohexyl-CH- | H | N-methylthiocarbamoyl-piperazinyl-CH₂-C(CH₃)- | $C_{31}H_{39}N_5OS$ | 529.75 | 204–206 | |

TABLE I-continued

R₃ = Ph

| Ex. | R | R₁ | R₂ | Molecular Formula | Molecular Weight | Melting Point (° C.) | [a]_D^{20} (c = 0.5, MeOH) |
|---|---|---|---|---|---|---|---|
| 76 | (S)-cyclohexyl-methyl | H | piperazine-pyrrolidine carboxamidine N-CN | $C_{35}H_{43}N_7O$ | 577.77 | 154–155 | |
| 77 | (S)-phenyl-ethyl | H | imidazolidinone-piperidine | $C_{34}H_{37}N_5O_2$ | 547.70 | 240–242 | |
| 78 | (S)-cyclohexyl-methyl | H | piperazine-pyrrolidine carboxamidine N-Me | $C_{35}H_{46}N_6O$ | 566.79 | amorphous solid | |
| 79 | (S)-phenyl-isopropyl | H | 4-piperidinopiperidine | $C_{37}H_{44}N_4O$ | 560.78 | 114–113 | |

TABLE I-continued

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 80 | (S)-CH(iPr)(Ph) | H | piperazine-N-C(O)CH₂CH₂N(Et)₂ | C₃₈H₄₇N₅O₂ | 605.82 | 120–125 | |
| 81 | (S)-CH(Cy) | H | piperazine-N-C(=CHNO₂)-pyrrolidine | C₃₅H₄₄N₆O₃ | 596.77 | 164–165 | |
| 82 | (S)-CH(Cy) | H | piperazine-N-C(=NH)NH₂ | C₃₀H₃₈N₆O | 757.00 | amorphous solid | |
| 83 | (S)-CH(Cy) | H | piperazine-N-C(O)CH₂CH₂COOH | C₃₃H₄₀N₄O₄ | 556.70 | 208–209 | |

TABLE I-continued

| Ex. | R | R₁ | R₂ | Molecular Formula | Molecular Weight | Melting Point (° C.) | $[\alpha]_D^{20}$ (c = 0.5, MeOH) |
|---|---|---|---|---|---|---|---|
| 84 | (S)-cyclohexyl-CH(CH₃)- | H | pyrrolidine-C(=N-SO₂CH₃)-N(piperazine)-CH₂-C(CH₃)₂- | C₃₅H₄₆N₆O₃S | 630.85 | 130–140 | |
| 85 | (S)-phenyl-CH(iPr)- | H | HOOC-CH₂-CH₂-C(=O)-N(piperazine)-CH₂-C(CH₃)₂- | C₃₅H₃₈N₄O₄ | 578.71 | 173–175 | |
| 86 | (S)-phenyl-CH(iPr)- | H | 2-(HOOC)-C₆H₄-C(=O)-N(piperazine)-CH₂-C(CH₃)₂- | C₃₉H₃₈N₄O₄ | 626.75 | 189–191 | |
| 87 | (S)-cyclohexyl-CH(CH₃)- | H | 2-(HOOC)-C₆H₄-C(=O)-N(piperazine)-CH₂-C(CH₃)₂- | C₃₇H₄₀N₄O₄ | 604.75 | 209–211 | |

R₃ = Ph

TABLE I-continued

Structure: quinoline-4-carboxamide with R-NH-C(=O)- at 4-position, R2 at 3-position, R3 at 2-position (R3 = Ph), R1 substituent on benzo ring.

| Ex. | R | R1 | R2 | Molecular Formula | Molecular Weight | Melting Point (° C.) | $[\alpha]_D^{20}$ (c = 0.5, MeOH) |
|---|---|---|---|---|---|---|---|
| 88 | (S)-cyclohexyl(ethyl)methyl | 7-OMe | 1-(neopentyl)piperidin-4-yl | $C_{36}H_{48}N_4O_2$ | 641.72 | 139–144 (dec) | +9.5 (c = 0.26) |
| 89 | (S)-phenyl(ethyl)methyl | 7-OH, 8-Cl | 1-(neopentyl)piperidin-4-yl | $C_{36}H_{41}ClN_4O_2$ | 670.12 | 209–216 (dec) | +13.7 (c = 0.42) |
| 90 | (S)-phenyl(ethyl)methyl | H | 4-(aminosulfonyl)-1-ethylpiperazinyl | $C_{30}H_{33}N_5O_3S$ | 543.69 | 133 (dec) | −58.4 (c = 0.22) |
| 91 | (S)-phenyl(ethyl)methyl | H | 4-(dimethylaminosulfonyl)-1-ethylpiperazinyl | $C_{32}H_{37}N_5O_3S$ | 571.74 | 107–111 (dec) | −56.6 (c = 0.37) |

TABLE I-continued

![Structure: R-NH-C(O)- attached to quinoline at 4-position with R2 at 3, R3 at 2 (R3 = Ph), R1 at 6/7; N in ring]

R3 = Ph

| Ex. | R | R1 | R2 | Molecular Formula | Molecular Weight | Melting Point (° C.) | $[\alpha]_D^{20}$ (c = 0.5, MeOH) |
|---|---|---|---|---|---|---|---|
| 92 | (S)-cyclohexyl-CH(Me)- | H | 4-ethylpiperazin-1-yl-CH2-CO2H (N-CH2CO2H on piperazine with N-Et) | $C_{31}H_{38}N_4O_3$ | 514.67 | 188–195 | |
| 93 | (S)-phenyl-CH(iPr)- | H | 4-(piperazin-1-yl)piperidin-1-yl (with NH) | $C_{36}H_{43}N_5O$ | 561.77 | amorphous solid | |
| 94 | (S)-cycloheptyl-CH(Me)- | H | 1-(piperidin-4-yl)piperidine with N-CH2- linker (gem-dimethyl) | $C_{36}H_{48}N_4O$ | 552.80 | amorphous solid | |
| 95 | (S)-phenyl-CH(Et)- | 7-OH | 1-(piperidin-4-yl)piperidine with N-CH2- linker (gem-dimethyl) | $C_{36}H_{42}N_4O_2$ | 562.75 | 158–162 | −41.88 (c = 0.22) |

TABLE 2

¹H NMR data of compounds of Examples of Table 1

| Example | ¹H NMR (Solvent) δ ppm |
|---|---|
| 1 | δ(DMSOd₆): 0.96(3H); 1.00–1.20(5H); 1.50–1.73(5H); 1.80–2.00(2H); 2.00–2.10(5H); 2.16(4H); 3.50(2H); 5.10(1H); 7.29(1H); 7.38(1H); 7.40–7.58(8H); 7.72(2H); 8.00(1H); 8.83(1H). |
| 2 | δ(DMSOd₆): 0.99(3H); 1.20–1.35(2H); 1.43–1.51(2H); 1.70–1.80(2H); 1.80–2.05(2H); 2.25(1H); 2.50(2H); 3.55(2H); 5.12(1H); 7.10(2H); 7.12(1H); 7.24(2H); 7.29(1H); 7.39(2H); 7.42–7.61(8H); 7.73(2H); 8.01(1H); 8.83(1H). |
| 3 | δ(DMSOd₆): 1.10–1.30(9H); 1.45–1.85(5H); 2.50–2.60(4H); 2.75–2.90(4H); 3.68(2H); 4.00–4.10(1H); 4.19(2H); 7.39–7.59(11H); 7.69(1H); 7.89(1H); 8.09(1H); 8.22(1H). |
| 4 | δ(DMSOd₆): 1.10–1.40(15H); 1.50–1.88(5H); 2.50–2.60(8H); 3.25–3.35(1H); 3.79(2H); 4.00–4.10(1H); 7.45–7.80(7H); 7.90(1H); 8.09(1H); 8.20(1H). |
| 5 | δ(DMSOd₆): 1.10–1.35(8H); 1.50–1.70(2H); 1.70–1.88(4H); 2.58(4H); 2.90–3.35(8H); 3.73 and 3.80(2H); 4.01–4.12(1H); 7.20–7.33(5H); 7.50–7.59(3H); 7.61–7.65(2H); 7.71(1H); 7.85(1H); 7.91(1H); 8.17(1H); 8.47(1H). |
| 6 | δ(DMSOd₆): 0.85(6H); 0.97(3H); 1.21(2H); 1.53(1H); 1.80–2.01(2H); 2.01–2.07(8H); 3.50(2H); 5.10(1H); 7.29(1H); 7.38(2H); 7.41–7.58(8H); 7.73(2H); 8.00(1H); 8.81(1H). |
| 7 | δ(DMSOd₆): 0.87(9H); 0.98(3H); 1.23(2H); 1.80–2.00(2H); 2.01–2.09(8H); 2.14(2H); 3.50(2H); 5.10(1H); 7.28(1H); 7.38(2H); 7.41–7.59(8H); 7.74(2H); 8.00(1H); 8.79(1H). |
| 8 | δ(DMSOd₆): 0.80(6H); 0.98(3H); 1.63(1H); 1.80–2.00(4H); 2.00–2.09(8H); 3.50(2H); 5.10(1H); 7.28(1H); 7.38(2H); 7.41–7.59(8H); 7.74(2H); 8.00(1H); 8.76(1H). |
| 9 | δ(DMSOd₆): 0.76–0.9(2H); 0.98(3H); 1.10–1.40(4H); 1.55–1.70(5H); 1.80–2.07(12H); 3.50(2H); 5.11(1H); 7.28(1H); 7.38(2H); 7.41–7.59(8H); 7.72(2H); 8.00(1H); 8.79(1H). |
| 10 | δ(DMSOd₆): 0.80(6H); 0.98(3H); 1.18–1.32(6H); 1.80–2.05(11H); 3.50(2H); 5.11(1H); 7.28(1H); 7.35(2H); 7.41–7.59(8H); 7.74(2H); 8.00(1H); 8.79(1H). |
| 11 | δ(DMSOd₆): 0.96(3H); 1.65–1.99(9H); 2.35–2.43(2H); 2.76(3H); –3.50(2H); 5.12(1H); 7.15–7.30(8H); 7.42–7.59(7H); 7.72(2H); 8.01(1H); 8.81(1H). |
| 12 | δ(DMSOd₆): 0.98(3H); 1.22–1.35(2H); 1.80–2.00(2H); 2.12–2.38(4H); 2.50–2.58(2H); 3.62(2H); 4.51(2H); 5.18(1H); 6.80(3H); 7.23–7.32(3H); 7.38(1H); 7.41–7.62(8H); 7.73(2H); 8.01(1H); 8.14(1H); 8.81(1H). |
| 13 | δ(DMSOd₆): 1.00–1.85(24H); 2.50(8H); 3.30(1H); 3.50(2H); 4.00(1H); 7.40–7.55(5H); 7.65(1H); 7.79(1H); 7.81(1H); 8.00(1H); 8.58(1H). |
| 14 | δ(DMSOd₆): 0.99(3H); 1.40–2.05(14H); 2.40–2.50(1H); 2.70–2.89(4H); 3.50(2H); 5.09(1H); 7.29(1H); 7.38(1H); 7.41–7.59(8H); 7.72(2H); 8.00(1H); 8.89(1H). |
| 15 | δ(CDCl₃): 1.06(3H); 1.65–2.30(10H and 1Hexch with D2O); 2.39(2H); 3.39–3.72(8H); 5.29(1H); 7.20–7.50(10Har and 1Hexch with D2O); 7.55(1Har); 7.72(1Har); 8.02(1Har); 7.13(1Har). |
| 16 | δ(CDCl₃): 1.04(3H); 1.62–2.55(10H); 2.37(2H); 3.28(3H); 3.37(2H); 3.64(2H); 5.31(1H); 7.18–7.50(10Har); 7.56(1Har); 7.72(1Har); 8.00–8.16(2Har); 8.98(1Hexch with D2O). |
| 17 | δ(CDCl₃): 1.00–1.32(5H); 1.28(3H); 1.42(1H); 1.52–1.95(5H); 2.03–2.58(10H); 3.30(3H); 3.43(2H); 3.77(2H); 4.26(1H); 7.35–7.52(5Har); 7.62(1Har); 7.73(1Har); 8.12(2Har); 8.47(1Hexch with D2O). |
| 18 | δ(CDCl₃): 1.04(3H); 0.70–1.35(2H); 1.40–2.61(14H and 1Hexch with D2O); 2.73(2H); 3.57(2H); 3.71(2H); 5.30(1H); 7.22–7.63(11Har); 7.72(1Har); 8.02(1Har); 8.12(1Har); 8.52(1Hexch with D2O). |
| 19 | δ(CDCl₃): 1.04(3H); 1.32–1.73(6H); 1.75–2.22(4H); 2.37(4H); 2.50(1H); 3.58(2H); 3.67(4H); 5.32(1H); 7.20–7.62(11Har); 7.71(1Har); 8.02(1Har); 8.11(1Har); 8.67(1Hexch with D2O). |
| 20 | δ(CDCl₃): 0.93–1.35(5H); 1.29(3H); 1.45(1H); 1.57–2.67(15H and 1Hexch with D2O); 3.43–3.71(6H); 3.76(2H); 4.25(1H); 7.32–7.50 (5Har); 7.48(1Har); 7.74(1Har); 7.60–7.90(1Hexch with D2O); 8.08(1Har); 8.13(1Har). |
| 21 | δ(CDCl3): 0.65–1.07(2H); 0.96(3H); 1.10–1.48(2H); 1.50–1.80(5H); 1.91(2H); 2.18(1H); 2.73(2H); 3.42(2H); 3.70(1H); 3.85(1H); 5.22(1H); 7.12–7.60(16Har); 7.72(1Har); 8.02(1Har); 8.12(1Har); 8.69(1Hexch with D2O). |
| 22 | δ(CDCl₃): 0.72–2.22(18H); 1.28(3H); 2.01(3H); 2.83(2H); 3.48(2H); 3.75(1H); 3.95(1H); 4.21(1H); 7.15–7.65(11Har and 1Hexch with D2O); 7.72(1Har); 8.06(1Har); 8.14(1Har). |
| 23 | δ(CDCl₃): 1.03(3H); 1.52–2.25(6H); 1.93(3H); 2.93(2H); 3.14(2H); 3.59(2H); 5.30(1H); 7.20–7.82(13Har); 7.97(1Hexch with D2O); 8.12(1Har). |
| 24 | δ(CDCl₃): 0.95–1.37(5H); 1.28(3H); 1.45(1H); 1.60–1.96(5H); 2.22(4H); 3.32(2H); 3.48(1H); 3.75(2H); 4.28(1H); 6.90(1Hexch with D2O); 7.20–7.66(11Har); 7.74(1Har); 7.00(1Har); 8.14(1Har). |
| 25 | δ(CDCl₃): 0.92–1.36(5H); 1.05(6H); 1.30(3H); 1.46(1H); 1.53–1.95(5H); 2.19(4H); 2.67(1H); 3.27(2H); 3.39(2H); 3.73(2H); 4.28(1H); 7.05(1Hexch with D2O); 3.37–7.54(5Har); 7.62(1Har); 7.78(1Har); 8.03(1Har); 8.17(1Har). |
| 26 | δ(CDCl₃): 0.95–1.37(5H); 1.31(3H); 1.62(1H); 1.56–1.98(5H); 2.26(4H); 3.61(4H); 3.80(2H); 4.29(1H); 6.46(1Har); 7.33–7.56(5Har); 7.60(1Har); 7.76(1Har); 7.83(1Hexch with D2O); 8.13(2Har); 8.25(2Har). |
| 27 | δ(CDCl₃): 1.05(3H); 1.60(2H); 1.92–2.22(4H); 3.39(4H); 3.65(2H); 5.38(1H); 6.44(1Har); 7.20–7.53(10Har); 7.58(1Har); 7.74(1Har); 8.07(1Har); 8.14(1Har); 8.28(1Har); 8.43(1Hexch with D2O). |
| 28 | δ(CDCl₃): 1.03(3H); 1.73–2.30(10H and 1Hexch with D2O); 2.41(2H); 3.54(2H); 3.63(2H); 5.29(1H); 7.25–7.50(10Har); 7.55(1Har); 7.72(1Har); 8.03(1Har); 8.11(1Har); 8.16(1Hexch with D2O). |
| 29 | δ(CDCl₃): 0.85–1.55(6H); 1.29(3H); 1.56–2.12(7H); 2.26(4H); 2.35(2H); 2.46(2H); 3.01(1Hexch with D2O); 3.55(2H); 3.76(2H); 4.26(1H); 7.35–7.52(5Har); 7.59(1Har); 7.74(1Har); 7.92(1Hexch with D2O); 8.11(2Har). |
| 30 | δ(DMSO, 353K): 1.25(2H); 1.45(2H); 1.55(3H); 1.65(6H); 2.72(4H); 3.00(5H); 3.50(2H); 5.32(1H); 7.60–7.27(11Har); 7.75(2Har); 8.01(1Har); 8.90(1Hexch with D2O). |
| 31 | δ(DMSOd₆) (80° C.): 0.98(3H); 1.92(2H); 2.23(4H); 3.23(4H); 3.80(2H); 5.03(1H); 7.15–7.90(18har); 8.08(1Har); 9.15(1Hexch with D2O). |
| 32 | δ(CDCl₃): 1.03(3H); 1.29–2.30(17H); 2.24(3H); 2.48(2H); 3.64(2H); 5.32(1H); 7.21–7.51(10Har); 7.58(1Har); 7.75(1Har); 8.13(2Har); 9.00(1Hexch with D2O). |
| 33 | δ(CDCl₃): 0.98–2.55(26H); 1.28(3H); 2.25(3H); 2.90(2H); 3.76(2H); 4.27(1H); 7.32–7.52(5Har); 7.59(1Har); 7.75(1Har); 8.13(2Har); 8.46(1Hexch with D2O). |
| 34 | δ(CDCl₃): 0.97–1.35(5H); 1.30(3H); 1.42(1H); 1.60–1.98(5H); 2.22(4H and 1Hexch with D2O); 2.70(4H); 3.72(2H); 4.27(1H); 7.35–7.52(5Har); 7.58(1Har); 7.75(1Har); 7.88(1Hexch with D2O); 8.08(1Har); 8.13(1 Har). |
| 35 | δ(CDCl₃): 0.78(12H); 1.01(3H); 1.92–2.42(18H); 3.60–3.95(2H); 5.28(1H); 7.22–7.56(11Har); 7.69(1Har); 7.82(1Har); 8.10(1Har); 8.49(1Hexch with D2O). |
| 36 | δ(CDCl₃): 0.70–2.03(20H); 1.42(3H); 3.43–3.64(3H); 7.37(1Hexch with D2O); 7.42–7.60(5Har); 7.66(1Har); 7.79(1Har); 7.94(1Har); 7.98(1Hexch with D2O); 8.03(1Har); 8.17(1Hexch with D2O). |
| 37 | δ(DMSO): 0.92(3H); 1.30–1.10(9H); 1.85–1.60(5H); 2.30–2.10(10H); 3.58(2H); 4.04(1H); 7.51–7.41(3Har); 7.57(2Har); 7.62(1Har); 7.76(1Har); 7.87(1Har); 8.01(1Har); 8.30(1Hexch with D2O). |
| 38 | δ(CDCl₃): 1.10(3H); 1.32–2.38(9H); 2.61(1H); 3.70(2H); 4.07(1H); 5.39(1H); 6.87–7.10(4Har); 7.22–7.64(11Har); 7.73(1Har); 8.04(1Har); 8.15(1Har); 8.30(1Hexch with D2O); 8.98(1Hexch with D2O). |
| 39 | δ(CDCl₃): 1.02–1.43(5H); 1.34(3H); 1.45–2.36(12H); 2.26(1H); 2.38(1H); 3.82(2H); 4.19(1H); 4.37(1H); 7.02(4Har); 7.38–7.86(7Har and 1Hexch with D2O); 8.09(1Har); 8.16(1Har); 8.91(1hexch with D2O). |
| 40 | δ(DMSOd₆) (80° C.): 0.99(3H); 1.47(2H); 1.72(2H); 1.90(2H); 2.03(3H); 2.64(3H); 2.55–3.00(3H); 3.28(2H); 4.05(2H); 5.10(1H); 7.25–7.95(13Har); 8.10(1Har); 9.49(1Hexch with D2O). |
| 41 | δ(CDCl₃): 0.95–2.95(26H); 2.64–3.32(16H); 3.95(1H); 4.11(1H); 4.38(1H); 6.82(1Hexch with D2O); 7.42–7.20(6Har); 7.61–7.87(2Har); 8.18(1Har). |

TABLE 2-continued

¹H NMR data of compounds of Examples of Table 1

| Example | ¹H NMR (Solvent) δ ppm |
|---|---|
| 42 | δ(CDCl₃): 0.92–1.94(17H); 1.29(3H); 2.04(1H); 2.43(4H); 2.53(1H); 2.79(1H); 3.52–3.82(6H); 4.28(1H); 7.34–7.55(5Har); 7.60(1Har); 7.72(1Har); 8.00–8.30(2Har and 1Hexch with D2O). |
| 43 | δ(CDCl₃): 0.95–2.07(23H and 1Hexch with D2O); 1.28(3H); 2.13–2.45(2H); 2.53(1H); 2.77(2H); 3.68(3H); 4.25(1H); 7.33–7.67(6Har); 7.75(1Har); 8.10(2Har); 7.70–8.20(1Hexch with D2O). |
| 44 | δ(CDCl₃): 0.94–2.02(27H); 2.30–2.61(2H); 2.98–3.40(4H); 3.73(2H); 4.25(1H); 7.32–7.52(5Har); 7.56(1Har); 7.72(1Har); 7.60–7.80(1Hexch with D2O); 8.06(1Har); 8.13(1Har). |
| 45 | δ(CDCl₃): 0.92–1.15(9H); 1.20–1.70(6H); 1.80–2.12(3H); 2.22(1H); 2.40(1H); 3.08(2H); 3.23(2H); 3.50(1H); 3.15(1H); 5.31(1H); 7.21–7.62(11Har); 7.20(1Har); 7.33–8.22(2Har and 1Hexch with D2O). |
| 46 | δ(CDCl₃): 1.00–1.49(5H); 1.28(3H); 1.47(1H); 1.60–1.97(5H); 2.09–2.47(4H); 2.21(6H); 3.01(2H); 3.36(4H); 3.73(2H); 4.27(1H); 7.06(1Hexch with D2O); 7.38–7.56(5Har); 7.60(1Har); 7.75(1Har); 8.02(1Har); 8.16(1Har). |
| 47 | δ(CDCl₃): 0.85–1.38(5H); 1.03(6H); 1.28(3H); 1.44(1H); 1.60–1.95(5H); 2.19(4H); 2.35–2.67(6H); 2.78(2H); 3.24(2H); 3.38(2H); 3.74(2H); 4.48(1H); 7.07(1Hexch with D2O); 7.34–7.59(5Har); 7.63(1Har); 7.78(1Har); 8.02(1Har); 8.14(1Har). |
| 48 | δ(DMSOd₆): 0.93–1.35(5H); 1.16(3H); 1.48(1H); 1.58–1.92(5H); 1.98–2.29(4H); 2.24(3H); 2.40(8H); 3.07(2H); 2.96–3.65(4H); 3.58(2H); 4.02(1H); 7.40–7.91(8Har); 8.04(1Har); 8.60(1Hexch with D2O). |
| 49 | δ(DMSO): 0.95(3H); 1.10(2H); 2.00–1.50(9H); 2.22(1H); 2.41(1H); 2.59(1H); 2.81(1H); 3.55(2H); 5.10(1H); 7.59–7.25(11Har); 7.75(2Har); 8.01(1Har); 8.83(1Hexch with D2O). |
| 50 | δ(DMSO + TFA 353 K): 1.00(3H); 1.30–1.10(6H); 1.89–1.50(17H); 2.02(2H); 3.20–2.80(7H); 4.00(1H); 4.20(2H); 7.61–7.51(3Har); 7.65(3Har); 7.88(1Har); 7.98(1Har); 8.10(1Har); 8.65(1Hexch with D2O). |
| 51 | δ(DMSOd₆): 0.90–1.35(5H); 1.14(3H); 1.46(1H); 1.55–1.90(5H); 2.03(4H); 2.22–2.52(8H); 3.15(4H); 3.42–3.70(6H); 3.99(1H); 7.32–8.12(6Har); 8.53(1Hexch with D2O). |
| 52 | δ(DMSOd₆): 0.95–1.35(5H); 1.20(3H); 1.46(1H); 1.58–1.88(5H); 2.05(2H); 2.87(4H); 3.03–3.30(4H); 3.60(2H); 4.01(1H); 6.86(1H); 7.30–8.10(10H and 1Hexch with D2O); 8.54(1Hexch with D2O). |
| 53 | δ(DMSOd₆): 0.95–1.32(5H); 1.17(3H); 1.47(1H); 1.55–1.95(5H); 2.26(4H); 2.82(12H); 3.03(4H); 3.62(2H); 4.01(1H); 7.38–7.88(8Har); 8.03(1Har); 8.54(1Hexch with D2O). |
| 54 | δ(DMSOd₆): 0.95–1.37(5H); 1.17(3H); 1.46(1H); 1.57–1.92(5H); 2.08(4H); 3.30(4H); 3.55(2H); 4.02(1H); 7.32–7.91(8Har); 8.02(1Har); 8.53(1Hexch with D2O). |
| 55 | δ(CDCl₃): 0.60–2.25(9H and 2Hexch with D2O); 1.06(3H); 2.41(2H); 3.57(2H); 5.30(1H); 7.15–7.65(10Har); 7.72(1Har); 8.02(1Har); 8.14(2Har); 8.80(1Hexch with D2O). |
| 56 | δ(CDCl₃): 1.03(3H); 1.75–2.28(6H); 3.09(4H); 3.65(2H); 5.33(1H); 6.45(1Har); 6.58(1Har); 7.18–7.65(12Har); 7.75(1Har); 8.93–8.20(3Har); 8.39(1Hexch with D2O). |
| 57 | δ(CDCl₃): 0.97(3H); 2.02(2H); 2.33(4H); 2.94(6H); 3.03(4H); 3.88(2H); 5.23(1H); 7.19–7.60(10Har and 1Hexch with D2O); 7.68(1Har); 7.86(1Har); 8.02(1har); 8.22(1Har). |
| 58 | δ(CDCl₃): 0.98–1.42(5H); 1.43–1.98(6H); 2.53(4H); 3.00(6H); 2.90–3.32(4H); 3.95(2H); 4.22(1H); 7.35–7.78(7Har and 1Hexch with D2O); 7.98(1Har); 8.10(1Har). |
| 59 | δ(CDCl₃): 1.30(3H); 0.95–2.02(11H); 2.31(4H); 3.32(4H); 3.80(2H); 4.28(1H); 6.48–6.68(2Har); 7.35–7.67(7Har); 7.73(1Har); 7.65–7.69(1Hexch with D2O); 8.02–8.22(3Har). |
| 60 | δ(CDCl₃): 0.77(3H); 0.85(3H); 1.02(3H); 1.70–2.58(8H); 3.59(2H); 2.78(1H); 7.15–7.65(11Har and 1Hexch with D2O); 7.75(1Har); 8.05(1Har); 8.14(1Har); 8.58(1Hexch with D2O). |
| 61 | δ(CDCl₃): 0.95–2.00(15H); 1.29(3H); 2.28(4H); 3.77(2H); 3.87(4H); 4.23(1H); 7.35–7.55(5Har); 7.60(1Har); 7.75(1Har); 7.95–8.25(2Har and 1Hexch with D2O). |
| 62 | δ(CDCl₃): 0.70–1.70(6H); 1.04(3H); 1.82–2.22(5H); 2.28(3H); 2.35–2.65(8H); 3.57(2H); 5.32(1H); 7.20–7.64(11Har); 7.73(1Har); 8.03(1Har); 8.13(1Har); 8.72(1Hexch with D2O). |
| 63 | δ(DMSOd₆): 0.95(3H); 0.94–1.45(4H); 1.50–2.25(6H); 2.65–3.02(4H); 3.30(2H); 5.06(1H); 7.20–8.00(13Har and 1Hexch with D2O); 8.02(1Har); 9.14(1Hexch with D2O). |
| 64 | δ(CDCl₃): 1.02(3H); 1.10–1.88(6H); 1.90–2.28(3H); 2.45(1H); 3.59(2H); 5.30(1H); 5.91(1Hexch with D2O); 7.18–7.62(11Har and 2Hexch with D2O); 7.72(1Har); 795(1har); 8.13(1Har). |
| 65 | δ(CDCl₃): 1.29–2.22(15H); 2.27(3H); 2.88(2H); 3.66(2H); 4.74(2H); 7.22–7.52(10Har); 7.59(1Har); 7.77(1Har); 8.12(1Har); 8.22(1Har); 9.64(1Hexch with D2O). |
| 66 | δ(DMSO 343 k): 0.95(3H); 1.08(2H); 1.65–1.25(11H); 1.88–1.80(2H); 2.50–2.25(6H); 3.41(2H); 3.92(3H); 5.09(1H); 7.60–7.15(12Har); 8.90(1Hexch with D2O). |
| 67 | δ(DMSO): 0.95(3H); 1.08(2H); 1.65–1.25(11H); 2.00–1.80(2H); 2.50–2.25(6H); 3.49(2H); 4.00(3H); 5.09(1H); 7.71–7.25(12Har); 8.90(1Hexch with D2O). |
| 68 | δ(DMSOd₆): 0.94(3H); 1.15–2.45(14H); 2.11(3H); 3.60(2H); 5.05(1H); 7.15–7.59(13Har); 8.02(1Har); 9.16(1Hexch with D2O) |
| 69 | δ(CDCl₃): 1.05–2.23(22H); 1.34(3H); 2.24–2.63(5H); 2.28(1H); 3.69(2H); 4.24(1H); 7.35–7.65(6Har); 7.73(1Har); 8.12(2Har); 8.47(1Hexch with D2O). |
| 70 | δ(CDCl₃): 0.80–1.44(4H); 1.04(3H); 1.53–2.29(7H); 2.50(1H); 2.89(2H); 3.20(2H); 3.63(2H); 4.02(1H); 4.49(1Hexch with D2O); 5.29(1H); 7.18–7.55(10Har); 7.56(1Har); 7.74(1Har); 8.10(2Har); 8.74(1Hexch with D2O). |
| 71 | δ(CDCl₃): 1.01(3H); 1.26(2H); 1.41–1.68(2H); 1.35–2.30(6H); 3.06(2H); 3.62(2H); 4.99(1Hexch with D2O); 5.26(1H); 7.22–7.50(10Har); 7.57(1Har); 7.73(1Har); 7.41(1Hexch with D2O); 8.02(1Har); 8.12(1Har). |
| 72 | δ(CDCl₃): 0.98–1.39(5H); 1.28(3H); 1.49(1H); 1.63–1.98(9H); 2.30(4H); 3.47(4H); 3.64(4H); 3.71(2H); 4.24(1H); 6.54(1Hexch with D2O); 7.35–7.53(5Har); 7.60(1Har); 7.73(1Har); 7.94(1Har); 8.12(1Har). |
| 73 | δ(CDCl₃): 0.99–1.37(5H); 1.27(3H); 1.48(1H); 1.63–1.90(5H); 2.23(4H); 2.93(3H); 3.19(4H); 3.70(2H); 4.24(1H); 4.84(1Hexch with D2O); 6.55(1Hexch with D2O); 7.36–7.52(5Har); 7.59(1Har); 7.73(1Har); 7.94(1Har); 8.13(1Har). |
| 74 | δ(CDCl₃): 0.98–1.37(5H); 1.26(3H); 1.42(1H); 1.54–1.93(5H); 2.20(4H); 3.21(4H); 3.25(2H); 3.75(2H); 3.95(2H); 4.26(1H); 7.32–7.67(5Har and 1Hexch with D2O); 7.58(1Har); 7.73(1Har); 8.03(1Har); 8.13(1Har). |
| 75 | δ(CDCl₃): 0.96–1.32(5H); 1.25(3H); 1.43(1H); 1.63–1.91(5H); 2.22(4H); 3.07(3H); 3.54(4H); 3.71(2H); 4.25(1H); 5.58(1Hexch with D2O); 6.90(1Hexch with D2O); 7.38–7.52(5Har); 7.58(1Har); 7.72(1Har); 8.92(1Har); 8.10(1Har). |
| 76 | δ(CDCl₃): 1.00–1.35(5H); 1.28(3H); 1.45(1H); 1.63–1.93(9H); 2.29(4H); 3.18(4H); 3.33(4H); 3.73(2H); 4.22(1H); 6.65(1Hexch with D2O); 7.42–7.15(5Har); 7.61(1Har); 7.71(1Har); 7.76(1Har); 8.13(1Har). |
| 77 | δ(DMSOd₆): 0.98(3H); 1.03–2.00(5H); 1.81(2H); 2.05–2.62(2H); 2.95–3.72(8H); 5.08(1H); 6.16(1Hexch with D2O); 7.17–7.70(12Har); 7.77(1Har); 8.02(1Har); 9.12(1Hexch with D2O). |
| 78 | δ(CDCl₃): 0.96–1.40(5H); 1.30(3H); 1.51(1H); 1.62–1.87(5H); 1.88–2.03(4H); 2.20–2.42(4H); 2.85, 2.87(3H, 2forms); 2.98–3.15(4H); 3.38–3.62(4H); 3.75(2H); 4.23(1H); 6.27(1Hexch with D2O); 7.38–7.81(7Har); 7.92(1Har); 8.15(1Har). |
| 79 | δ(CDCl₃): 0.93(3H); 1.19(3H); 1.05–1.65(8H); 1.68–1.83(4H); 1.90–2.55(8H); 3.52(2H); 5.14(1H); 7.33–7.60(11Har); 7.71(1Har); 8.00(1Har); 8.11(1Har); 8.47(1Hexch with D2O). |
| 80 | δ(CDCl₃): 0.94(3H); 1.08(6H); 1.17(3H); 1.86(4H); 2.23(1H); 2.46(2H); 2.63(4H); 2.83(2H); 3.02(2H); 3.17(2H); 3.53(2H); 5.14(1H); 7.29–7.55(11Har and 1Hexch with D2O); 7.73(1Har); 7.91(1Har); 8.13(1Har) |
| 81 | δ(CDCl₃): 0.99–1.38(5H); 1.30(3H); 1.49(1H); 1.57–1.99(9H); 2.18–2.38(4H); 2.98–3.15(4H); 3.22–3.37(4H); 3.75(2H); 4.25(1H); 6.28(1H); 6.63(1Hexch |

TABLE 2-continued

¹H NMR data of compounds of Examples of Table 1

| Example | ¹H NMR (Solvent) δ ppm |
|---|---|
|  | with D2O); 7.37–7.55(5Har); 7.60(1Har); 7.74(1Har); 7.98(1Har); 8.14(1Har). |
| 82 | δ(DMSOd₆): 0.951–1.32(8H); 1.32(1H); 1.57–1.86(5H); 2.15–2.36(4H); 2.29(3H); 2.77(2H); 3.11(2H); 3.60(2H); 4.00(1H); 7.11(2Har); 7.27(2Hexch with D2O); 7.48(2Har); 7.49–7.61(5Har); 7.62(1Har); 7.88(2Har); 8.03(1Har); 8.57(3Hexch with D2O). |
| 83 | δ(CDCl₃): 0.98–1.36(5H); 1.28(3H); 1.45(1H); 1.60–1.95(5H); 2.08–2.27(4H); 2.47–2.66(4H); 3.00(1Hexch with D2O); 3.23(2H); 3.37(2H); 3.73(2H); 4.26(1H); 6.85(1Hexch with D2O); 7.39–7.54(5Har); 7.60(1Har); 7.75(1Har); 7.99(1Har); 8.15(1Har). |
| 84 | δ(CDCl₃): 1.00–1.39(5H); 1.29(3H); 1.47(1H); 1.68–1.97(9H); 2.18–2.36(4H); 2.92(3H); 3.16–3.49(8H); 3.74(2H); 4.25(1H); 6.93(1Hexch with D2O); 7.38–7.53(5Har); 7.59(1Har); 7.74(1Har); 8.00(1Har); 8.13(1Har). |
| 85 | δ(CDCl₃): 0.93(3H); 1.17(3H); 1.71–2.03(4H); 2.21(1H); 2.40–2.66(4H); 300–3.50(1Hexch with D2O); 3.01(2H); 3.18(2H); 3.51(2H); 5.13(1H); 7.01(1Hexch with D2O); 7.25–7.52(10Har); 7.55(1Har); 7.73(1Har); 7.89(1Har); 8.14(1Har). |
| 86 | δ(CD₃COD): 0.84(3H); 1.19(3H); 1.36–2.41(5H); 2.65(2H); 2.80–3.70(2H); 3.24(1H); 3.45(1H); 4.96(1H); 7.00–8.15(18Har and 2Hexch with D2O). |
| 87 | δ(CD₃COD): 1.01–1.96(11H); 1.25(3H); 1.97–2.53(4H); 2.93(2H); 3.20–3.80(2H); 3.67(2H); 4.10(1H); 7.17(1Har); 7.37–8.14(12H and 2Hexch with D2O). |
| 88 | δ(DMSO): 1.40–1.08(5H); 1.50(2H); 1.90–1.63(21H); 3.10–2.50(5H); 4.54(2H); 3.91(3H); 4.00(1H); 7.28(1Har); 7.41(1Har); 7.57–7.42(5Har); 7.74(1Har); 8.29(1Hexch with D2O). |
| 89 | δ(DMSO): 0.95(3H); 1.08(2H); 1.60–1.30(11H); 1.96–1.75(3H); 2.50–2.25(6H); 3.30(2H); 5.00(1H); 6.80(1Har); 7.42–7.12(9Har); 7.54(2Har); 8.65(1Hexch with D2O). |
| 90 | δ(DMSO 343K): 0.97(3H); 2.10–1.80(6H); 2.69(4H); 3.51(2H); 5.09(1H); 6.40(2Hexch with D2O); 7.55–7.21(11Har); 7.72(2Har); 8.00(1Har); 8.89(1Hexch with D2O). |
| 91 | δ(DMSO 343K): 0.98(3H); 2.10–1.80(6H); 2.70(6H); 2.79(4H); 3.55(2H); 5.10(1H); 7.57–7.21(11Har); 7.75(2Har); 8.00(1Har); 8.89(1Hexch with D2O); |
| 92 | δ(DMSOd₆): 0.88–1.35(5H); 1.16(3H); 1.45(1H); 1.53–1.93(5H); 2.16(4H); 2.30(4H); 2.90(2H); 3.56(2H and 1Hexch with D2O); 4.02(1H); 7.22–7.90(8Har); 8.03(1Har); 8.55(1Hexch with D2O)ppm. |
| 93 | δ(CDCl₃): 0.94(3H); 0.98–1.34(2H); 1.19(3H); 1.36–1.67(2H); 1.70–2.56(6H and 1Hexch with D20); 2.43(4H); 2.88(4H); 2.52(2H); 5.15(1H); 7.22–7.60(11Har); 7.71(1Har); 7.99(1Har); 8.11(1Har); 8.35(1Hexch with D2O). |
| 94 | δ(CDCl3): 1.13–2.66(31H); 2.81(1H); 3.64(1H); 3.74(1H); 4.35(1H); 7.38–7.53(5Har); 7.58(1Har); 7.73(1Har); 8.13(1Har); 7.70–8.50(1Hexch with D2O) |
| 95 | δ(DMSOd₆): 0.95(3H); 1.09(2H); 1.34–1.50(8H); 1.50–1.65(2H); 1.80–1.98(3H); 2.35(4H); 2.42(2H); 3.40(2H); 5.09(1H); 7.09(1Har); 7.22(1Har); 7.25–7.55(11Har); 8.88(1Hexch with D2O); 9.98(1Hexch with D2O). |

TABLE 3

Chemical names of parent compounds of Examples of Table 1 (names generated by Beilstein's Autonom)

| Example | Chemical name |
|---|---|
| 1 | 3-(4-Cyclohexyl-piperazin-1-ylmethyl)-2-phenyl-quinoline-4-carboxylic acid ((S)-1-phenyl-propyl)-amide |
| 2 | 2-Phenyl-3-(4-phenyl-piperidin-1-ylmethyl)-quinoline-4-carboxylic acid ((S)-1-phenyl-propyl)-amide |
| 3 | 3-(4-Benzyl-piperazin-1-ylmethyl)-2-phenyl-quinoline-4-carboxylic acid ((S)-1-cyclohexyl-ethyl)-amide |
| 4 | 3-(4-Isopropyl-piperazin-1-ylmethyl)-2-phenyl-quinoline-4-carboxylic acid ((S)-1-cyclohexyl-ethyl)-amide |
| 5 | 3-(4-Phenethyl-piperazin-1-ylmethyl)-2-phenyl-quinoline-4-carboxylic acid ((S)-1-cyclohexyl-ethyl)-amide |
| 6 | 3-[4-(3-Methyl-butyl)-piperazin-1-ylmethyl]-2-phenyl-quinoline-4-carboxylic acid ((S)-1-phenyl-propyl)-amide |
| 7 | 3-[4-(3,3-Dimethyl-butyl)-piperazin-1-ylmethyl]-2-phenyl-quinoline-4-carboxylic acid ((S)-1-phenyl-propyl)-amide |
| 8 | 3-(4-Isobutyl-piperazin-1-ylmethyl)-2-phenyl-quinoline-4-carboxylic acid ((S)-1-phenyl-propyl)-amide |
| 9 | 3-(4-Cyclohexylmethyl-piperazin-1-ylmethyl)-2-phenyl-quinoline-4-carboxylic acid ((S)-1-phenyl-propyl)-amide |
| 10 | 3-[4-(2-Ethyl-butyl)-piperazin-1-ylmethyl]-2-phenyl-quinoline-4-carboxylic acid ((S)-1-phenyl-propyl)-amide |
| 11 | 3-[(Acetyl-methyl-amino)-phenyl-piperidin-1-ylmethyl]-2-phenyl-quinoline-4-carboxylic acid ((S)-1-phenyl-propyl)-amide |
| 12 | 3-(4-Oxo-1-phenyl-1,3,8-triaza-spiro[4.5]dec-8-ylmethyl)-2-phenyl-quinoline-4-carboxylic acid ((S)-1-phenyl-propyl)-amide |
| 13 | 3-[1,4']Bipiperidinyl-1'-ylmethyl-2-phenyl-quinoline-4-carboxylic acid ((S)-1-cyclohexyl-ethyl)-amide |
| 14 | 3-[1,4']Bipiperidinyl-1'-ylmethyl-2-phenyl-quinoline-4-carboxylic acid ((S)-1-phenyl-propyl)-amide |
| 15 | 3-{4-[2-(2-Hydroxy-ethoxy)-ethyl]-piperazin-1-ylmethyl}-2-phenyl-quinoline-4-carboxylic acid ((S)-1-phenyl-propyl)-amide |
| 16 | 3-[4-(2-Methoxy-ethyl)-piperazin-1-ylmehyl]-2-phenyl-quinoline-4-carboxylic acid ((S)-1-phenyl-propyl)-amide |
| 17 | 3-[4-(2-Methoxy-ethyl)-piperazin-1-ylmethyl]-2-phenyl-quinoline-4-carboxylic acid ((S)-1-cyclohexyl-ethyl)-amide |
| 18 | 3-(4-Hydroxy-[1,4']bipiperidinyl-1'-ylmethyl)-2-phenyl-quinoline-4-carboxylic acid ((S)-1-phenyl-propyl)-amide |
| 19 | 3-(4-Morpholin-4-yl-piperidin-1-ylmethyl)-2-phenyl-quinoline-4-carboxylic acid ((S)-1-phenyl-propyl)-amide |
| 20 | 3-{4-[2-(2-Hydroxy-ethoxy)-ethyl]-piperazin-1-ylmethyl}-2-phenyl-quinoline-4-carboxylic acid ((S)-1-cyclohexyl-ethyl)-amide |
| 21 | 3-{[(1-Benzyl-piperidin-4-yl)-methyl-amino]-methyl}-2-phenyl-quinoline-4-carboxylic acid ((S)-1-phenyl-propyl)-amide |
| 22 | 3-{[(1-Benzyl-piperidin-4-yl)-methyl-amino]-methyl}-2-phenyl-quinoline-4-carboxylic acid ((S)-1-cyclohexyl-ethyl)-amide |
| 23 | 3-(4-Acetyl-piperazin-1-ylmethyl)-2-phenyl-quinoline-4-carboxylic acid ((S)-1-phenyl-propyl)-amide |
| 24 | 2-Phenyl-3-[4-(1-phenyl-methanoyl)-piperazin-1-ylmethyl]-quinoline-4-carboxylic acid ((S)-1-cyclohexyl-ethyl)-amide |
| 25 | 3-[4-(2-Methyl-propanoyl)-piperazin-1-ylmethyl]-2-phenyl-quinoline-4-carboxylic acid ((S)-1-cyclohexyl-ethyl)-amide |
| 26 | 2-Phenyl-3-(4-pyrimidin-2-yl-piperazin-1-ylmethyl)-quinoline-4-carboxylic acid ((S)-1-cyclohexyl-ethyl)-amide |
| 27 | 2-Phenyl-3-(4-pyrimidin-2-yl-piperazin-1-ylmethyl)-quinoline-4-carboxylic acid ((S)-1-phenyl-propyl)-amide |
| 28 | 3-[4-(2-Hydroxy-ethyl)-piperazin-1-ylmethyl]-2-phenyl-quinoline-4-carboxylic acid ((S)-1-phenyl-propyl)-amide |
| 29 | 3-[4-(2-Hydroxy-ethyl)-piperazin-1-ylmethyl]-2-phenyl-quinoline-4-carboxylic acid ((S)-1-cyclohexyl-ethyl)-amide |
| 30 | 3-[1,4']Bipiperidinyl-1'-ylmethyl-2-phenyl-quinoline-4-carboxylic acid ((S)-1-phenyl-ethyl)-amide |
| 31 | 2-Phenyl-3-[4-(1-phenyl-methanoyl)-piperazin-1-ylmethyl]-quinoline-4-carboxylic acid ((S)-1-phenyl-propyl)-amide |
| 32 | 3-[4-(1-Methyl-piperidin-4-yl)-piperazin-1-ylmethyl]-2-phenyl-quinoline-4-carboxylic acid ((S)-1-phenyl-propyl)-amide |
| 33 | 3-[4-(1-Methyl-piperidin-4-yl)-piperazin-1-ylmethyl]-2-phenyl-quinoline-4-carboxylic acid ((S)-1-cyclohexyl-ethyl)-amide |
| 34 | 2-Phenyl-3-piperazin-1-ylmethyl-quinoline-4-carboxylic acid ((S)-1-cyclohexyl-ethyl)-amide |
| 35 | 3-{[Bis-(2-diethylamino-ethyl)-amino]-methyl}-2-phenyl-quinoline-4-carboxylic acid ((S)-1-phenyl-propyl)-amide |
| 36 | 3-(4-Carbamoyl-piperidin-1-ylmethyl)-2-phenyl-quinoline-4-carboxylic acid ((S)-1-cyclohexyl-ethyl)-amide |

TABLE 3-continued

Chemical names of parent compounds of Examples of Table 1
(names generated by Beilstein's Autonom)

| Example | Chemical name |
|---|---|
| 37 | 3-(4-Ethyl-piperazin-1-ylmethyl)-2-phenyl-quinoline-4-carboxylic acid ((S)-1-cyclohexyl-ethyl)-amide |
| 38 | 3-[4-(2-Oxo-2,3-dihydro-benzoimidazol-1-yl)-piperidin-1-ylmethyl]-2-phenyl-quinoline-4-carboxylic acid ((S)-1-phenyl-propyl)-amide |
| 39 | 3-[4-(2-Oxo-2,3-dihydro-benzoimidazol-1-yl)-piperidin-1-ylmethyl]-2-phenyl-quinoline-4-carboxylic acid ((S)-1-cyclohexyl-ethyl)-amide |
| 40 | 3-{[Methyl-(1-methyl-piperidin-4-yl)-amino]-methyl}-2-phenyl-quinoline-4-carboxylic acid ((S)-1-phenyl-propyl)-amide |
| 41 | 3-{[Bis-(2-diethylamino-ethyl)-amino]-methyl}-2-phenyl-quinoline-4-carboxylic acid ((S)-1-cyclohexyl-ethyl)-amide |
| 42 | 3-(4-Morpholin-4-yl-piperidin-1-ylmethyl)-2-phenyl-quinoline-4-carboxylic acid ((S)-1-cyclohexyl-ethyl)-amide |
| 43 | 3-(4-Hydroxy-[1,4']bipiperidinyl-1'-ylmethyl)-2-phenyl-quinoline-4-carboxylic acid ((S)-1-cyclohexyl-ethyl)-amide |
| 44 | 3-(3-Diethylcarbamoyl-piperidin-1-ylmethyl)-2-phenyl-quinoline-4-carboxylic acid ((S)-1-cyclohexyl-ethyl)-amide |
| 45 | 3-(3-Diethylcarbamoyl-piperidin-1-ylmethyl)-2-phenyl-quinoline-4-carboxylic acid ((S)-1-phenyl-propyl)-amide |
| 46 | 3-[4-(2-Dimethylamino-ethanoyl)-piperazin-1-ylmethyl]-2-phenyl-quinoline-4-carboxylic acid ((S)-1-cyclohexyl-ethyl)-amide |
| 47 | 3-[4-(3-Diethylamino-propanoyl)-piperazin-1-ylmethyl]-2-phenyl-quinoline-4-carboxylic acid ((S)-1-cyclohexyl-ethyl)-amide |
| 48 | 3-{4-[2-(4-Methyl-piperazin-1-yl)-ethanoyl]-piperazin-1-ylmethyl}-2-phenyl-quinoline-4-carboxylic acid ((S)-1-cyclohexyl-ethyl)-amide |
| 49 | 3-(Hexahydro-pyrrolo[1,2-a]pyrazin-2-ylmethyl)-2-phenyl-quinoline-4-carboxylic acid ((S)-1-phenyl-propyl)-amide |
| 50 | 3-[1,4']Bipiperidinyl-1'-ylmethyl-2-phenyl-quinoline-4-carboxylic acid |
| 51 | 3-[4-(3-Morpholin-4-yl-propanoyl)-piperazin-1-ylmethyl]-2-phenyl-quinoline-4-carboxylic acid ((S)-1-cyclohexyl-ethyl)-amide |
| 52 | 3-[4-(2-1H-Imidazol-4-yl-ethanoyl)-piperazin-1-ylmethyl]-2-phenyl-quinoline-4-carboxylic acid ((S)-1-cyclohexyl-ethyl)-amide |
| 53 | ({4-[4-((S)-1-Cyclohexyl-ethylcarbamoyl)-2-phenyl-quinolin-3-ylmethyl]-piperazin-1-yl}-dimethylamino-methylene)-dimethyl-ammonium |
| 54 | 3-Morpholin-4-ylmethyl-2-phenyl-quinoline-4-carboxylic acid ((S)-1-cyclohexyl-ethyl)-amide |
| 55 | 3-(4-Amino-piperidin-1-ylmethyl)-2-phenyl-quinoline-4-carboxylic acid ((S)-1-phenyl-propyl)-amide |
| 56 | 2-Phenyl-3-(4-pyridin-2-yl-piperazin-1-ylmethyl)-quinoline-4-carboxylic acid ((S)-1-phenyl-propyl)-amide |
| 57 | 3-{[Bis-(2-methoxy-ethyl)-amino]-methyl}-2-phenyl-quinoline-4-carboxylic acid ((S)-1-phenyl-propyl)-amide |
| 58 | 3-{[Bis-(2-methoxy-ethyl)-amino]-methyl}-2-phenyl-quinoline-4-carboxylic acid ((S)-1-cyclohexyl-ethyl)-amide |
| 59 | 2-Phenyl-3-(4-pyridin-2-yl-piperazin-1-ylmethyl)-quinoline-4-carboxylic acid ((S)-1-cyclohexyl-ethyl)-amide |
| 60 | 3-((3R,5S)-3,5-Dimethyl-piperazin-1-ylmethyl)-2-phenyl-quinoline-4-carboxylic acid ((S)-1-phenyl-propyl)-amide |
| 61 | 3-(1,4-Dioxa-8-aza-spiro[4.5]dec-8-ylmethyl)-2-phenyl-quinoline-4-carboxylic acid ((S)-1-cyclohexyl-ethyl)-amide |
| 62 | 3-[4-(4-Methyl-piperazin-1-yl)-piperidin-1-ylmethyl]-2-phenyl-quinoline-4-carboxylic acid ((S)-1-phenyl-propyl)-amide |
| 63 | 3-(3-Oxo-2,8-diaza-spiro[4.5]dec-8-ylmethyl)-2-phenyl-quinoline-4-carboxylic acid ((S)-1-phenyl-propyl)-amide |
| 64 | 3-(2,4-Dioxo-1,3,8-triaza-spiro[4.5]dec-8-ylmethyl)-2-phenyl-quinoline-4-carboxylic acid ((S)-1-phenyl-propyl)-amide |
| 65 | 3-[4-(1-Methyl-piperidin-4-yl)-piperazin-1-ylmethyl]-2-phenyl-quinoline-4-carboxylic acid benzylamide |
| 66 | 3-[1,4']Bipiperidinyl-1'-ylmethyl-8-bromo-7-methoxy-2-phenyl-quinoline-4-carboxylic acid ((S)-1-phenyl-propyl)-amide |
| 67 | 3-[1,4']Bipiperidinyl-1'-ylmethyl-7-methoxy-2-phenyl-quinoline-4-carboxylic acid ((S)-1-phenyl-propyl)-amide |
| 68 | 3-(7-Methyl-2,7-diaza-spiro[4.4]non-2-ylmethyl)-2-phenyl-quinoline-4-carboxylic acid ((S)-1-phenyl-propyl)-amide |
| 69 | 3-[1,4']Bipiperidinyl-1'-ylmethyl-2-phenyl-quinoline-4-carboxylic acid ((S)-1-cyclopentyl-ethyl)-amide |
| 70 | 3-[4-(2-Oxo-tetrahydro-pyrimidin-1-yl)-piperidin-1-ylmethyl]-2-phenyl-quinoline-4-carboxylic acid ((S)-1-phenyl-propyl)-amide |
| 71 | 3-(2-Oxo-3-oxa-1,8-diaza-spiro[4.5]dec-8-ylmethyl)-2-phenyl-quinoline-4-carboxylic acid ((S)-1-phenyl-propyl)-amide |
| 72 | 3-[4-(3,4-Dioxo-2-pyrrolidin-1-yl-cyclobut-1-enyl)-piperazin-1-ylmethyl]-2-phenyl-quinoline-4-carboxylic acid ((S)-1-cyclohexyl-ethyl)-amide |
| 73 | 3-[4-(-1-Cyanoimino-1-methylamino-methyl)-piperazin-1-ylmethyl]-2-phenyl-quinoline-4-carboxylic acid ((S)-1-cyclohexyl-ethyl)amide |
| 74 | 3-[4-(4,5-Dihydro-thiazol-2-yl)-piperazin-1-ylmethyl]-2-phenyl-quinoline-4-carboxylic acid ((S)-1-cyclohexyl-ethyl)-amide |
| 75 | 3-(4-Methylthiocarbamoyl-piperazin-1-ylmethyl)-2-phenyl-quinoline-4-carboxylic acid ((S)-1-cyclohexyl-ethyl)-amide |
| 76 | 3-[4-(1-Cyanoimino-1-pyrrolidin-1-yl-methyl)-piperazin-1-ylmethyl]-2-phenyl-quinoline-4-carboxylic acid ((S)-1-cyclohexyl-ethyl)-amide |
| 77 | 3-[4-(2-Oxo-imidazolidin-1-yl)-piperidin-1-ylmethyl]-2-phenyl-quinoline-4-carboxylic acid ((S)-1-phenyl-propyl)-amide |
| 78 | 3-[4-(1-Methylimino-1-pyrrolidin-1-yl-methyl)-piperazin-1-ylmethyl]-2-phenyl-quinoline-4-carboxylic acid ((S)-1-cyclohexyl-ethyl)-amide |
| 79 | 3-[1,4']Bipiperidinyl-1'-ylmethyl-2-phenyl-quinoline-4-carboxylic acid ((S)-2-methyl-1-phenyl-propyl)-amide |
| 80 | 3-[4-(3-Diethylamino-propanoyl)-piperazin-1-ylmethyl]-2-phenyl-quinoline-4-carboxylic acid ((S)-2-methyl-1-phenyl-propyl)-amide |
| 81 | 3-[4-(2-Nitro-1-pyrrolidin-1-yl-vinyl)-piperazin-1-ylmethyl]-2-phenyl-quinoline-4-carboxylic acid ((S)-1-cyclohexyl-ethyl)-amide |
| 82 | 3-(4-Carbamimidoyl-piperazin-1-ylmethyl)-2-phenyl-quinoline-4-carboxylic acid ((S)-1-cyclohexyl-ethyl)-amide |
| 83 | 4-{4-[4-((S)-1-Cyclohexyl-ethylcarbamoyl)-2-phenyl-quinolin-3-ylmethyl]-piperazin-1-yl}-4-oxo-butyric acid |
| 84 | 3-[4-(1-Methanesulfonylimino-1-pyrrolidin-1-yl-methyl)-piperazin-1-ylmethyl]-2-phenyl-quinoline-4-carboxylic acid ((S)-1-cyclohexyl-ethyl)-amide |
| 85 | 4-{4-[4-((S)-2-Methyl-1-phenyl-propylcarbamoyl)-2-phenyl-quinolin-3-ylmethyl]-piperazin-1-yl}-4-oxo-butyric acid |
| 86 | 2-(1-{4-[4-((S)-2-Methyl-1-phenyl-propylcarbamoyl)-2-phenyl-quinolin-3-ylmethyl]-piperazin-1-yl}-methanoyl)-benzoic acid |
| 87 | 2-(1-{4-[4-((S)-1-Cyclohexyl-ethylcarbamoyl)-2-phenyl-quinolin-3-ylmethyl]-piperazin-1-yl}-methanoyl)-benzoic acid |
| 88 | 3-[1,4']Bipiperidinyl-1'-ylmethyl-7-methoxy-2-phenyl--quinoline-4-carboxylic acid ((S)-1-cyclohexyl-ethyl)-amide |
| 89 | 3-[1,4']Bipiperidinyl-1'-ylmethyl-8-chloro-7-hydroxy-2-phenyl-quinoline-4-carboxylic acid ((S)-1-phenyl-propyl)-amide |
| 90 | 2-Phenyl-3-(4-sulfamoyl-piperazin-1-ylmethyl)-quinoline-4-carboxylic acid ((S)-1-phenyl-propyl)-amide |
| 91 | 3-(4-Dimethylsulfamoyl-piperazin-1-ylmethyl)-2-phenyl-quinoline-4-carboxylic acid ((S)-1-phenyl-propyl)-amide |
| 92 | {4-[4-((S)-1-Cyclohexyl-ethylcarbamoyl)-2-phenyl-quinolin-3-ylmethyl]-piperazin-1-yl}-acetic acid |
| 93 | 2-Phenyl-3-(4-piperazin-1-yl-piperidin-1-ylmethyl)-quinoline-4-carboxylic acid ((S)-2-methyl-1-phenyl-propyl)-amide |

TABLE 3-continued

Chemical names of parent compounds of Examples of Table 1
(names generated by Beilstein's Autonom)

| Example | Chemical name |
|---|---|
| 94 | 3-[1,4']Bipiperidinyl-1'-ylmethyl-2-phenyl-quinoline-4-carboxylic acid ((S)-1-cycloheptyl-ethyl)-amide |
| 95 | 3-[1,4']Bipiperidinyl-1'-ylmethyl-7-hydroxy-2-phenyl-quinoline-4-carboxylic acid ((S)-1-phenyl-propyl)-amide |

What is claimed is:

1. A compound selected from:

3-(4-Cyclohexyl-piperazin-1-ylmethyl)-2-phenyl-quinoline-4-carboxylic acid ((S)-1-phenyl-propyl)-amide;

2-Phenyl-3-(4-phenyl-piperidin-1-ylmethyl)-quinoline-4-carboxylic acid ((S)-1-phenyl-propyl)-amide;

3-(4-Benzyl-piperazin-1-ylmethyl)-2-phenyl-quinoline-4-carboxylic acid ((S)-1-cyclohexyl-ethyl)-amide;

3-(4-Isopropyl-piperazin-1-ylmethyl)-2-phenyl-quinoline-4-carboxylic acid ((S)-1-cyclohexyl-ethyl)-amide;

3-(4-Phenethyl-piperazin-1-ylmethyl)-2-phenyl-quinoline-4-carboxylic acid ((S)-1-cyclohexyl-ethyl)-amide;

3-[4-(3-Methyl-butyl)-piperazin-1-ylmethyl]-2-phenyl-quinoline-4-carboxylic acid ((S)-1-phenyl-propyl)-amide;

3-[4-(3,3-Dimethyl-butyl)-piperazin-1-ylmethyl]-2-phenyl-quinoline-4-carboxylic acid ((S)-1-phenyl-propyl)-amide;

3-(4-Isobutyl-piperazin-1-ylmethyl)-2-phenyl-quinoline-4-carboxylic acid ((S)-1-phenyl-propyl)-amide;

3-(4-Cyclohexylmethyl-piperazin-1-ylmethyl)-2-phenyl-quinoline-4-carboxylic acid ((S)-1-phenyl-propyl)-amide;

3-[4-(2-Ethyl-butyl)-piperazin-1-ylmethyl]-2-phenyl-quinoline-4-carboxylic acid ((S)-1-phenyl-propyl)-amide;

3-[(Acetyl-methyl-amino)-phenyl-piperidin-1-ylmethyl]-2-phenyl-quinoline-4-carboxylic acid ((S)-1-phenyl-propyl)-amide;

3-(4-Oxo-1-phenyl-1,3,8-triaza-spiro[4.5]dec-8-ylmethyl)-2-phenyl-quinoline-4-carboxylic acid ((S)-1-phenyl-propyl)-amide;

3-[1,4']Bipiperidinyl-1'-ylmethyl-2-phenyl-quinoline-4-carboxylic acid ((S)-1-cyclohexyl-ethyl)-amide;

3-[1,4']Bipiperidinyl-1'-ylmethyl-2-phenyl-quinoline-4-carboxylic acid ((S)-1-phenyl-propyl)-amide;

3-{4-[2-(2-Hydroxy-ethoxy)-ethyl]-piperazin-1-ylmethyl}-2-phenyl-quinoline-4-carboxylic acid ((S)-1-phenyl-propyl)-amide;

3-[4-(2-Methoxy-ethyl)-piperazin-1-ylmethyl]-2-phenyl-quinoline-4-carboxylic acid ((S)-1-phenyl-propyl)-amide;

3-[4-(2-Methoxy-ethyl)-piperazin-1-ylmethyl]-2-phenyl-quinoline-4-carboxylic acid ((S)-1-cyclohexyl-ethyl)-amide;

3-(4-Hydroxy-[1,4']bipiperidinyl-1'-ylmethyl)-2-phenyl-quinoline-4-carboxylic acid ((S)-1-phenyl-propyl)-amide;

3-(4-Morpholin-4-yl-piperidin-1-ylmethyl)-2-phenyl-quinoline-4-carboxylic acid ((S)-1-phenyl-propyl)-amide;

3-{4-[2-(2-Hydroxy-ethoxy)-ethyl]-piperazin-1-ylmethyl}-2-phenyl-quinoline-4carboxylic acid ((S)-1-cyclohexyl-ethyl)-amide;

3-{[(1-Benzyl-piperidin-4-yl)-methyl-amino]-methyl}-2-phenyl-quinoline-4-carboxylic acid ((S)-1-phenyl-propyl)-amide;

3-{[(1-Benzyl-piperidin-4-yl)-methyl-amino]-methyl}-2-phenyl-quinoline-4-carboxylic acid ((S)-1-cyclohexyl-ethyl)-amide;

3-(4-Acetyl-piperazin-1-ylmethyl)-2-phenyl-quinoline-4-carboxylic acid ((S)-1-phenyl-propyl)-amide;

2-Phenyl-3-[4-(1-phenyl-methanoyl)-piperazin-1-ylmethyl]-quinoline-4-carboxylic acid ((S)-1-cyclohexyl-ethyl)-amide;

3-[4-(2-Methyl-propanoyl)-piperazin-1-ylmethyl]-2-phenyl-quinoline-4-carboxylic acid ((S)-1-cyclohexyl-ethyl)-amide;

2-Phenyl-3-(4-pyrimidin-2-yl-piperazin-1-ylmethyl)-quinoline-4-carboxylic acid ((S)-1-cyclohexyl-ethyl)-amide;

2-Phenyl-3-(4-pyrimidin-2-yl-piperazin-1-ylmethyl)-quinoline-4-carboxylic acid ((S)-1-phenyl-propyl)-amide;

3-[4-(2-Hydroxy-ethyl)-piperazin-1-ylmethyl]-2-phenyl-quinoline-4-carboxylic acid ((S)-1-phenyl-propyl)-amide;

3-[4-(2-Hydroxy-ethyl)-piperazin-1-ylmethyl]-2-phenyl-quinoline-4-carboxylic acid ((S)-1-cyclohexyl-ethyl)-amide;

3-[1,4']Bipiperidinyl-1'-ylmethyl-2-phenyl-quinoline-4-carboxylic acid ((S)-1-phenyl-ethyl)-amide;

2-Phenyl-3-[4-(1-phenyl-methanoyl)-piperazin-1-ylmethyl]-quinoline-4-carboxylic acid ((S)-1-phenyl-propyl)-amide;

3-[4-(1-Methyl-piperidin-4-yl)-piperazin-1-ylmethyl]-2-phenyl-quinoline-4-carboxylic acid ((S)-1-phenyl-propyl)-amide;

3-[4-(1-Methyl-piperidin-4-yl)-piperazin-1-ylmethyl]-2-phenyl-quinoline-4-carboxylic acid ((S)-1-cyclohexyl-ethyl)-amide;

2-Phenyl-3-piperazin-1-ylmethyl-quinoline-4-carboxylic acid ((S)-1-cyclohexyl-ethyl)-amide;

3-{[Bis-(2-diethylamino-ethyl)-amino]-methyl}-2-phenyl-quinoline-4-carboxylic acid ((S)-1-phenyl-propyl)-amide;

3-(4-Carbamoyl-piperidin-1-ylmethyl)-2-phenyl-quinoline-4-carboxylic acid ((S)-1-cyclohexyl-ethyl)-amide;

3-(4-Ethyl-piperazin-1-ylmethyl)-2-phenyl-quinoline-4-carboxylic acid ((S)-1-cyclohexyl-ethyl)-amide;

3-[4-(2-Oxo-2,3-dihydro-benzoimidazol-1-yl)-piperidin-1-ylmethyl]-2-phenyl-quinoline-4-carboxylic acid ((S)-1-phenyl-propyl)-amide;

3-[4-(2-Oxo-2,3-dihydro-benzoimidazol-1-yl)-piperidin-1-ylmethyl]-2-phenyl-quinoline-4-carboxylic acid ((S)-1-cyclohexyl-ethyl)-amide;

3-{[Methyl-(1-methyl-piperidin-4-yl)-amino]-methyl}-2-phenyl-quinoline-4-carboxylic acid ((S)-1-phenyl-propyl)-amide;

3-{[Bis-(2-diethylamino-ethyl)-amino]-methyl}-2-phenyl-quinoline-4-carboxylic acid ((S)-1-cyclohexyl-ethyl)-amide;

3-(4-Morpholin-4-yl-piperidin-1-ylmethyl)-2-phenyl-quinoline-4-carboxylic acid ((S)-1-cyclohexyl-ethyl)-amide;

3-(4-Hydroxy-[1,4']bipiperidinyl-1'-ylmethyl)-2-phenyl-quinoline-4-carboxylic acid ((S)-1-cyclohexyl-ethyl)-amide;

3-(3-Diethylcarbamoyl-piperidin-1-ylmethyl)-2-phenyl-quinoline-4-carboxylic acid ((S)-1-cyclohexyl-ethyl)-amide;

3-(3-Diethylcarbamoyl-piperidin-1-ylmethyl)-2-phenyl-quinoline-4-carboxylic acid ((S)-1-phenyl-propyl)-amide;

3-[4-(2-Dimethylamino-ethanoyl)-piperazin-1-ylmethyl]-2-phenyl-quinoline-4-carboxylic acid ((S)-1-cyclohexyl-ethyl)-amide;

3-[4-(3-Diethylamino-propanoyl)-piperazin-1-ylmethyl]-2-phenyl-quinoline-4-carboxylic acid ((S)-1-cyclohexyl-ethyl)-amide;

3-{4-[2-(4-Methyl-piperazin-1-yl)-ethanoyl]-piperazin-1-ylmethyl}-2-phenyl-quinoline-4-carboxylic acid ((S)-1-cyclohexyl-ethyl)-amide;

3-(Hexahydro-pyrrolo[1,2-a]pyrazin-2-ylmethyl)-2-phenyl-quinoline-4-carboxylic acid ((S)-1-phenyl-propyl)-amide;

3-[1,4']Bipiperidinyl-1'-ylmethyl-2-phenyl-quinoline-4-carboxylic acid;

3-[4-(3-Morpholin-4-yl-propanoyl)-piperazin-1-ylmethyl]-2-phenyl-quinoline-4-carboxylic acid ((S)-1-cyclohexyl-ethyl)-amide;

3-[4-(2-1H-Imidazol-4-yl-ethanoyl)-piperazin-1-ylmethyl]-2-phenyl-quinoline-4-carboxylic acid ((S)-1-cyclohexyl-ethyl)-amide;

({4-[4-((S)-1-Cyclohexyl-ethylcarbamoyl)-2-phenyl-quinolin-3-ylmethyl]-piperazin-1-yl}-dimethylamino-methylene)-dimethyl-ammonium;

3-Morpholin-4-ylmethyl-2-phenyl-quinoline-4-carboxylic acid ((S)-1-cyclohexyl-ethyl)-amide;

3-(4-Amino-piperidin-1-ylmethyl)-2-phenyl-quinoline-4-carboxylic acid ((S)-1-phenyl-propyl)-amide;

2-Phenyl-3-(4-pyridin-2-yl-piperazin-1-ylmethyl)-quinoline-4-carboxylic acid ((S)-1-phenyl-propyl)-amide;

3-{[Bis-(2-methoxy-ethyl)-amino]-methyl}-2-phenyl-quinoline-4-carboxylic acid ((S)-1-phenyl-propyl)-amide;

3-{[Bis-(2-methoxy-ethyl)-amino]-methyl}-2-phenyl-quinoline-4-carboxylic acid ((S)-1-cyclohexyl-ethyl)-amide;

2-Phenyl-3-(4-pyridin-2-yl-piperazin-1-ylmethyl)-quinoline-4-carboxylic acid ((S)-1-cyclohexyl-ethyl)-amide;

3-((3R,5S)-3,5-Dimethyl-piperazin-1-ylmethyl)-2-phenyl-quinoline-4-carboxylic acid ((S)-1-phenyl-propyl)-amide;

3-(1,4-Dioxa-8-aza-spiro[4.5]dec-8-ylmethyl)-2-phenyl-quinoline-4-carboxylic acid ((S)-1-cyclohexyl-ethyl)-amide;

3-[4-(4-Methyl-piperazin-1-yl)-piperidin-1-ylmethyl]-2-phenylquinoline-4-carboxylic acid ((S)-1-phenyl-propyl)-amide;

3-(3-Oxo-2,8-diaza-spiro[4.5]dec-8-ylmethyl)-2-phenyl-quinoline-4-carboxylic acid ((S)-1-phenyl-propyl)-amide;

3-(2,4-Dioxo-1,3,8-triaza-spiro[4.5]dec-8-ylmethyl)-2-phenyl-quinoline-4-carboxylic acid ((S)-1-phenyl-propyl)-amide;

3-[4-(1-Methyl-piperidin-4-yl)-piperazin-1-ylmethyl]-2-phenyl-quinoline-4-carboxylic acid benzylamide;

3-[1,4']Bipiperidinyl-1'-ylmethyl-8-bromo-7-methoxy-2-phenyl-quinoline-4-carboxylic acid ((S)-1-phenyl-propyl)-amide;

3-[1,4']Bipiperidinyl-1'-ylmethyl-7-methoxy-2-phenyl-quinoline-4-carboxylic acid ((S)-1-phenyl-propyl)-amide;

3-(7-Methyl-2,7-diaza-spiro[4.4]non-2-ylmethyl)-2-phenyl-quinoline-4-carboxylic acid ((S)-1-phenyl-propyl)-amide;

3-[1,4']Bipiperidinyl-1'-ylmethyl-2-phenyl-quinoline-4carboxylic acid ((S)-1-cyclopentyl-ethyl)-amide;

3-[4-(2-Oxo-tetrahydro-pyrimidin-1-yl)-piperidin-1-ylmethyl]-2-phenyl-quinoline-4-carboxylic acid ((S)-1-phenyl-propyl)-amide;

3-(2-Oxo-3-oxa-1,8-diaza-spiro[4.5]dec-8-ylmethyl)-2-phenyl-quinoline-4-carboxylic acid ((S)-1-phenyl-propyl)-amide;

3-[4-(3,4-Dioxo-2-pyrrolidin-1-yl-cyclobut-1-enyl)-piperazin-1-ylmethyl]-2-phenyl-quinoline-4-carboxylic acid ((S)-1-cyclohexyl-ethyl)-amide;

3-[4-(-1-Cyanoimino-1-methylamino-methyl)-piperazin-1-ylmethyl]-2-phenyl-quinoline-4-carboxylic acid ((S)-1-cyclohexyl-ethyl)amide;

3-[4-(4,5-Dihydro-thiazol-2-yl)-piperazin-1-ylmethyl]-2-phenyl-quinoline-4-carboxylic acid ((S)-1-cyclohexyl-ethyl)-amide;

3-(4-Methylthiocarbamoyl-piperazin-1-ylmethyl)-2-phenyl-quinoline-4-carboxylic acid ((S)-1-cyclohexyl-ethyl)-amide;

3-[4-(1-Cyanoimino-1-pyrrolidin-1-yl-methyl)-piperazin-1-ylmethyl]-2-phenyl-quinoline-4-carboxylic acid ((S)-1-cyclohexyl-ethyl)-amide;

3-[4-(2-Oxo-imidazolidin-1-yl)-piperidin-1-ylmethyl]-2-phenyl-quinoline-4-carboxylic acid ((S)-1-phenyl-propyl)-amide;

3-[4-(1-Methylimino-1-pyrrolidin-1-yl-methyl)-piperazin-1-ylmethyl]-2-phenyl-quinoline-4-carboxylic acid ((S)-1-cyclohexyl-ethyl)-amide;

3-[1,4']Bipiperidinyl-1'-ylmethyl-2-phenyl-quinoline-4-carboxylic acid ((S)-2-methyl-1-phenyl-propyl)-amide;

3-[4-(3-Diethylamino-propanoyl)-piperazin-1-ylmethyl]-2-phenyl-quinoline-4-carboxylic acid ((S)-2-methyl-1-phenyl-propyl)-amide;

3-[4-(2-Nitro-1-pyrrolidin-1-yl-vinyl)-piperazin-1-ylmethyl]-2-phenyl-quinoline-4-carboxylic acid ((S)-1-cyclohexyl-ethyl)-amide;

3-(4-Carbamimidoyl-piperazin-1-ylmethyl)-2-phenyl-quinoline-4-carboxylic acid ((S)-1-cyclohexyl-ethyl)-amide;

4-{4-[4-((S)-1-Cyclohexyl-ethylcarbamoyl)-2-phenyl-quinolin-3-ylmethyl]-piperazin-1-yl}-4-oxo-butyric acid;

3-[4-(1-Methanesulfonylimino-1-pyrrolidin-1-yl-methyl)-piperazin-1-ylmethyl]-2-phenyl-quinoline-4-carboxylic acid ((S)-1-cyclohexyl-ethyl)-amide;

4-{4-[4-((S)-2-Methyl-1-phenyl-propylcarbamoyl)-2-phenyl-quinolin-3-ylmethyl]-piperazin-1-yl}-4-oxo-butyric acid;

2-(1-{4-[4-((S)-2-Methyl-1-phenyl-propylcarbamoyl)-2-phenyl-quinolin-3-ylmethyl]-piperazin-1-yl}-methanoyl)-benzoic acid;

2-(1-{4-[4-((S)-1-Cyclohexyl-ethylcarbamoyl)-2-phenyl-quinolin-3-ylmethyl]-piperazin-1-yl}-methanoyl)-benzoic acid;

3-[1,4']Bipiperidinyl-1'-ylmethyl-7-methoxy-2-phenyl-quinoline-4-carboxylic acid ((S)-1-cyclohexyl-ethyl)-amide;

3-[1,4']Bipiperidinyl-1'-ylmethyl-8-chloro-7-hydroxy-2-phenyl-quinoline-4-carboxylic acid ((S)-1-phenyl-propyl)-amide;

2-Phenyl-3-(4-sulfamoyl-piperazin-1-ylmethyl)-quinoline-4-carboxylic acid ((S)-1-phenyl-propyl)-amide;

3-(4-Dimethylsulfamoyl-piperazin-1-ylmethyl)-2-phenyl-quinoline-4-carboxylic acid ((S)-1-phenyl-propyl)-amide;

{4-[4-((S)-1-Cyclohexyl-ethylcarbamoyl)-2-phenyl-quinolin-3-ylmethyl]-piperazin-1-yl}-acetic acid;

2-Phenyl-3-(4-piperazin-1-yl-piperidin-1-ylmethyl)-quinoline-4-carboxylic acid ((S)-2-methyl-1-phenyl-propyl)-amide;

3-[1,4']Bipiperidinyl-1'-ylmethyl-2-phenylquinoline-4-carboxylic acid ((S)-1-cycloheptyl-ethyl)-amide; and 3-[1,4']Bipiperidinyl-1'-ylmethyl-7-hydroxy-2-phenyl-quinoline-4-carboxylic acid ((S)-1-phenyl-propyl)-amide.

2. A compound selected from:

3-{4-[2-(2-Hydroxy-ethoxy)-ethyl]-piperazin-1-ylmethyl}-2-phenyl-quinoline-4-carboxylic acid ((S)-1-cyclohexyl-ethyl)-amide;

3-[4-(2-Hydroxy-ethyl)-piperazin-1-ylmethyl]-2-phenyl-quinoline-4-carboxylic acid ((S)-1-cyclohexyl-ethyl)-amide;

3-[4-(1-Methyl-piperidin-4-yl)-piperazin-1-ylmethyl]-2-phenyl-quinoline-4-carboxylic acid ((S)-1-phenyl-propyl)-amide;

3-[4-(1-Methyl-piperidin-4-yl)-piperazin-1-ylmethyl]-2-phenyl-quinoline-4-carboxylic acid ((S)-1-cyclohexyl-ethyl)-amide;

2-Phenyl-3-piperazin-1-ylmethyl-quinoline-4-carboxylic acid ((S)-1-cyclohexyl-ethyl)-amide;

3-[4-(2-Dimethylamino-ethanoyl)-piperazin-1-ylmethyl]-2-phenyl-quinoline-4-carboxylic acid ((S)-1-cyclohexyl-ethyl)-amide;

3-[4-(3-Diethylamino-propanoyl)-piperazin-1-ylmethyl]-2-phenyl-quinoline-4-carboxylic acid ((S)-1-cyclohexyl-ethyl)-amide;

3-{4-[2-(4-Methyl-piperazin-1-yl)-ethanoyl]-piperazin-1-ylmethyl}-2-phenyl-quinoline-4-carboxylic acid ((S)-1-cyclohexyl-ethyl)-amide;

({4-[4-((S)-1-Cyclohexyl-ethylcarbamoyl)-2-phenyl-quinolin-3-ylmethyl]-piperazin-1-yl}-dimethylamino-methylene)-dimethyl-ammonium;

3-(4-Amino-piperidin-1-ylmethyl)-2-phenyl-quinoline-4-carboxylic acid ((S)-1-phenyl-propyl)-amide;

3-[4-(4-Methyl-piperazin-1-yl)-piperidin-1-ylmethyl]-2-phenyl-quinoline-4-carboxylic acid ((S)-1-phenyl-propyl)-amide;

3-[1,4']Bipiperidinyl-1'-ylmethyl-7-methoxy-2-phenyl-quinoline-4-carboxylic acid ((S)-1-phenyl-propyl)-amide;

3-[4-(1-Methylimino-1-pyrrolidin-1-yl-methyl)-piperazin-1-ylmethyl]-2-phenyl-quinoline-4-carboxylic acid ((S)-1-cyclohexyl-ethyl)-amide;

3-[1,4']Bipiperidinyl-1'-ylmethyl-2-phenyl-quinoline-4-carboxylic acid ((S)-2-methyl-1-phenyl-propyl)-amide;

3-[4-(3-Diethylamino-propanoyl)-piperazin-1-ylmethyl]-2-phenyl-quinoline-4-carboxylic acid ((S)-2-methyl-1-phenyl-propyl)-amide;

3-[4-(2-Nitro-1-pyrrolidin-1-yl-vinyl)-piperazin-1-ylmethyl]-2-phenyl-quinoline-4-carboxylic acid ((S)-1-cyclohexyl-ethyl)-amide; and 3-[1,4']Bipiperidinyl-1'-ylmethyl-7-hydroxy-2-phenyl-quinoline-4-carboxylic acid ((S)-1-phenyl-propyl)-amide.

3. A pharmaceutical composition comprising a compound according to claim 1 or a pharmaceutically acceptable salt or solvate thereof, and a pharmaceutically acceptable carrier.

4. A pharmaceutical composition comprising a compound according to claim 2 or a pharmaceutically acceptable salt or solvate thereof, and a pharmaceutically acceptable carrier.

5. A compound which is 3-[1,4']Bipiperidinyl-1'-ylmethyl-2-phenyl-quinoline-4-carboxylic acid ((S)-1-cyclohexyl-ethyl)-amide dihydrochloride.

6. A pharmaceutical composition comprising a compound according to claim 5 or a pharmaceutically acceptable solvate thereof, and a pharmaceutically acceptable carrier.

\* \* \* \* \*